(12) United States Patent
Walsh et al.

(10) Patent No.: US 11,278,426 B2
(45) Date of Patent: *Mar. 22, 2022

(54) SPINAL SURGERY ASSEMBLIES, SYSTEMS, AND METHODS

(71) Applicant: GetSet Surgical SA, Epalinges (CH)

(72) Inventors: David Walsh, Reading, MA (US); Ole Stoklund, Lausanne (CH); John Kapitan, Leicester, NC (US)

(73) Assignee: GetSet Surgical SA, Epalinges (CH)

( * ) Notice: Subject to any disclaimer, the term of this patent is extended or adjusted under 35 U.S.C. 154(b) by 300 days.

This patent is subject to a terminal disclaimer.

(21) Appl. No.: 16/696,525

(22) Filed: Nov. 26, 2019

(65) Prior Publication Data
US 2021/0153879 A1    May 27, 2021

Related U.S. Application Data

(63) Continuation-in-part of application No. 16/695,952, filed on Nov. 26, 2019, now Pat. No. 11,173,042.

(51) Int. Cl.
*A61F 2/44* (2006.01)
*A61F 2/46* (2006.01)
(Continued)

(52) U.S. Cl.
CPC .......... *A61F 2/447* (2013.01); *A61B 17/1757* (2013.01); *A61B 17/7062* (2013.01);
(Continued)

(58) Field of Classification Search
CPC .......... A61F 2/44; A61F 2/442; A61F 2/4455; A61F 2/446; A61F 2/4465; A61F 2/447; A61F 2/46; A61F 2/4603; A61F 2/4611
See application file for complete search history.

(56) References Cited

U.S. PATENT DOCUMENTS 2,796,101 A    6/1957  Hasemann
5,364,399 A   11/1994  Lowery et al.
(Continued)

FOREIGN PATENT DOCUMENTS

EP    2391308 B1   12/2015
EP    2688520 B1    9/2017
(Continued)

OTHER PUBLICATIONS

International Search Report and Written Opinion dated Mar. 1, 2021 for corresponding International Application No. PCT/US2020/062421.
(Continued)

*Primary Examiner* — Eric S Gibson
(74) *Attorney, Agent, or Firm* — David Meibos; Maywood IP Law

(57) ABSTRACT

An insertion assembly may include a DTS guide and an inserter tool configured to couple an intervertebral spacer having a fastener channel configured to receive a fastener and a locking member channel with a first engagement feature. The inserter tool may include a second engagement feature configured to engage the first engagement feature and removably couple the inserter tool with the intervertebral spacer. The DTS guide may include a shaft lumen configured to receive the inserter tool and slidably couple with the inserter tool. The DTS guide may also include a DTS guide channel configured to receive the fastener and a DTS guide wing. The DTS guide wing may abut against a surface of the intervertebral spacer to align the DTS guide channel with the fastener channel and guide the fastener through the DTS guide channel and into the fastener channel.

20 Claims, 42 Drawing Sheets

(51) Int. Cl.
*A61B 17/17* (2006.01)
*A61B 17/70* (2006.01)
*A61B 17/88* (2006.01)
A61B 17/68 (2006.01)
A61B 17/90 (2006.01)

(52) U.S. Cl.
CPC ........ *A61B 17/8897* (2013.01); *A61F 2/4611* (2013.01); *A61B 17/686* (2013.01); *A61B 17/90* (2021.08)

(56) References Cited

U.S. PATENT DOCUMENTS

| | | |
|---|---|---|
| 5,423,826 A | 6/1995 | Coates et al. |
| 5,549,612 A | 8/1996 | Yapp et al. |
| 5,951,558 A | 9/1999 | Fiz |
| 6,152,927 A | 11/2000 | Farris et al. |
| 6,193,721 B1 | 2/2001 | Michelson |
| 6,306,139 B1 | 10/2001 | Fuentes |
| 6,383,186 B1 | 5/2002 | Michelson |
| 6,428,542 B1 | 8/2002 | Michelson |
| 6,558,432 B2 | 5/2003 | Schulte et al. |
| 6,730,127 B2 | 5/2004 | Michelson |
| 6,884,242 B2 | 4/2005 | LeHuec et al. |
| 6,890,335 B2 | 5/2005 | Grabowski et al. |
| 7,288,094 B2 | 10/2007 | Lindemann et al. |
| 7,651,497 B2 | 1/2010 | Michelson |
| 7,674,279 B2* | 3/2010 | Johnson ............. A61B 17/8042 606/295 |
| 7,833,226 B2 | 11/2010 | Grabowski et al. |
| 7,875,062 B2* | 1/2011 | Lindemann ........ A61B 17/8042 606/295 |
| 7,901,413 B1 | 3/2011 | Lewis |
| 7,998,180 B2 | 8/2011 | Erickson et al. |
| 8,048,075 B2 | 11/2011 | Michelson |
| 8,066,750 B2 | 11/2011 | Oi et al. |
| 8,211,148 B2 | 7/2012 | Zhang et al. |
| 8,216,285 B2 | 7/2012 | Markworth |
| 8,246,660 B2 | 8/2012 | Boris et al. |
| 8,262,705 B2 | 9/2012 | Bray |
| 8,277,493 B2 | 10/2012 | Farris et al. |
| 8,328,872 B2* | 12/2012 | Duffield ................. A61F 2/44 623/17.16 |
| 8,348,982 B2 | 1/2013 | Baynham et al. |
| 8,419,795 B2 | 4/2013 | Sweeney |
| 8,439,593 B2 | 5/2013 | Slater et al. |
| 8,480,717 B2 | 7/2013 | Michelson |
| 8,523,920 B2 | 9/2013 | Gause et al. |
| 8,562,655 B2 | 10/2013 | Butler |
| 8,591,556 B2 | 11/2013 | Hansell et al. |
| 8,613,761 B2 | 12/2013 | Lindemann et al. |
| 8,617,222 B2 | 12/2013 | Shipp et al. |
| 8,672,984 B2 | 3/2014 | Lindemann et al. |
| 8,696,721 B2 | 4/2014 | Blain |
| 8,795,341 B2 | 8/2014 | Walker et al. |
| 8,795,373 B2* | 8/2014 | Jones ................. A61B 17/8042 623/17.16 |
| 8,858,603 B1 | 10/2014 | Zufelt |
| 8,858,604 B2 | 10/2014 | Biyani et al. |
| 8,882,843 B2 | 11/2014 | Michelson |
| 8,932,335 B2 | 1/2015 | Humphreys |
| 8,940,030 B1 | 1/2015 | Stein et al. |
| 8,979,910 B2 | 3/2015 | Stanaford et al. |
| 9,005,288 B2 | 4/2015 | McCormack et al. |
| 9,005,293 B2 | 4/2015 | Moskowitz et al. |
| 9,017,412 B2* | 4/2015 | Wolters .................. A61F 2/442 623/17.16 |
| 9,028,498 B2 | 5/2015 | Hershgold et al. |
| 9,107,710 B1 | 8/2015 | Swann |
| 9,114,023 B2 | 8/2015 | Kana et al. |
| 9,119,682 B2 | 9/2015 | Stoll et al. |
| 9,155,572 B2 | 10/2015 | Altarac et al. |
| 9,179,952 B2 | 11/2015 | Biedermann et al. |
| 9,180,020 B2 | 11/2015 | Gause et al. |
| 9,186,189 B2 | 11/2015 | Campbell et al. |
| 9,220,548 B2 | 12/2015 | Duong et al. |
| 9,241,749 B2 | 1/2016 | Lombardo et al. |
| 9,265,546 B2 | 2/2016 | Blain |
| 9,277,943 B2 | 3/2016 | Holly et al. |
| 9,326,803 B2 | 5/2016 | Humphreys |
| 9,351,768 B2 | 5/2016 | Rinner et al. |
| 9,364,340 B2* | 6/2016 | Lawson ................ A61F 2/4455 |
| 9,381,093 B1 | 7/2016 | Morris et al. |
| 9,402,735 B2 | 8/2016 | McDonough et al. |
| 9,414,935 B2 | 8/2016 | McDonough et al. |
| 9,421,055 B2 | 8/2016 | Suh |
| 9,445,851 B2 | 9/2016 | Walker et al. |
| 9,451,951 B2 | 9/2016 | Sullivan et al. |
| 9,468,534 B2 | 10/2016 | Garber et al. |
| 9,622,875 B2 | 4/2017 | Moskowitz et al. |
| 9,744,052 B2 | 8/2017 | Moskowitz et al. |
| 9,814,601 B2 | 11/2017 | Moskowitz et al. |
| 9,826,973 B2 | 11/2017 | Graul et al. |
| 9,867,719 B2 | 1/2018 | Moskowitz et al. |
| 9,889,022 B2 | 2/2018 | Moskowitz et al. |
| 9,937,060 B2 | 4/2018 | Fuhrer et al. |
| 9,980,826 B2* | 5/2018 | Martynova ............. A61F 2/442 |
| 2004/0133280 A1 | 7/2004 | Trieu |
| 2006/0293668 A1 | 12/2006 | May et al. |
| 2007/0123995 A1 | 5/2007 | Thelen et al. |
| 2008/0033440 A1 | 2/2008 | Moskowitz et al. |
| 2010/0016901 A1 | 1/2010 | Robinson |
| 2010/0057206 A1* | 3/2010 | Duffield .............. A61F 2/30771 623/17.16 |
| 2010/0292696 A1 | 11/2010 | Chantelot et al. |
| 2012/0071933 A1 | 3/2012 | DeRidder |
| 2012/0150301 A1* | 6/2012 | Gamache ............... A61F 2/447 623/17.16 |
| 2012/0158068 A1 | 6/2012 | Humphreys |
| 2012/0277803 A1 | 11/2012 | Remesh et al. |
| 2013/0197588 A1 | 8/2013 | Abdou |
| 2014/0012384 A1 | 1/2014 | Kana et al. |
| 2014/0046377 A1 | 2/2014 | Hansell et al. |
| 2014/0180422 A1* | 6/2014 | Klimek ............... A61F 2/30744 623/17.16 |
| 2014/0214081 A1 | 7/2014 | Schwab et al. |
| 2014/0257487 A1* | 9/2014 | Lawson ............. A61B 17/8042 623/17.16 |
| 2014/0288655 A1 | 9/2014 | Parry et al. |
| 2014/0336770 A1* | 11/2014 | Petersheim ............. A61F 2/447 623/17.16 |
| 2014/0371859 A1* | 12/2014 | Petersheim ............. A61F 2/447 623/17.16 |
| 2015/0025635 A1 | 1/2015 | Laubert |
| 2015/0066096 A1 | 3/2015 | Bush, Jr. et al. |
| 2015/0201982 A1 | 7/2015 | Altarac et al. |
| 2016/0022335 A1 | 1/2016 | Humphreys |
| 2016/0038309 A1 | 2/2016 | Doyle |
| 2016/0128737 A1 | 5/2016 | Coric et al. |
| 2016/0128746 A1 | 5/2016 | Dunaway |
| 2016/0151171 A1* | 6/2016 | Mozeleski ......... A61B 17/7059 623/17.16 |
| 2016/0166396 A1 | 6/2016 | McClintock |
| 2016/0213410 A1 | 7/2016 | Humphreys |
| 2016/0220388 A1* | 8/2016 | Flores ................... A61F 2/4611 |
| 2016/0228156 A1 | 8/2016 | Morris et al. |
| 2016/0228165 A1 | 8/2016 | Walker et al. |
| 2016/0235448 A1* | 8/2016 | Seex .................... A61F 2/4611 |
| 2016/0250037 A1* | 9/2016 | Duffield ............ A61B 17/8042 623/17.16 |
| 2016/0270832 A1 | 9/2016 | Bush, Jr. et al. |
| 2016/0310295 A1* | 10/2016 | Reed ..................... A61F 2/4611 |
| 2016/0324554 A1 | 11/2016 | Suh |
| 2017/0049579 A1 | 2/2017 | Quinlan et al. |
| 2017/0189204 A1* | 7/2017 | Riemhofer ........... A61F 2/4611 |
| 2018/0049756 A1* | 2/2018 | Livorsi ................. A61F 2/4611 |
| 2018/0055651 A1 | 3/2018 | Moskowitz et al. |
| 2018/0318099 A1* | 11/2018 | Altarac ............... A61B 17/8042 |
| 2018/0318100 A1 | 11/2018 | Altarac et al. |
| 2019/0133778 A1 | 5/2019 | Johnston |

(56) References Cited

U.S. PATENT DOCUMENTS

| | | | |
|---|---|---|---|
| 2021/0153879 A1* | 5/2021 | Walsh | A61B 17/1631 |
| 2021/0153913 A1* | 5/2021 | Walsh | A61F 2/447 |
| 2021/0154022 A1* | 5/2021 | Walsh | A61F 2/4611 |

FOREIGN PATENT DOCUMENTS

| | | | |
|---|---|---|---|
| JP | 2016524988 A | | 8/2016 |
| WO | WO2007136452 A3 | | 7/2008 |
| WO | WO2010054181 | | 5/2010 |
| WO | WO2010078488 A2 | | 7/2010 |
| WO | WO2013098828 A1 | | 7/2013 |
| WO | WO2014094551 A1 | | 6/2014 |
| WO | WO2015025108 A1 | | 2/2015 |
| WO | WO2015051119 A1 | | 4/2015 |

OTHER PUBLICATIONS

International Search Report and Written Opinion dated Apr. 6, 2021 for corresponding International Application No. PCT/US2020/062422.

International Search Report and Written Opinion dated Mar. 3, 2021 for corresponding International Application No. PCT/US2020/062424.

\* cited by examiner

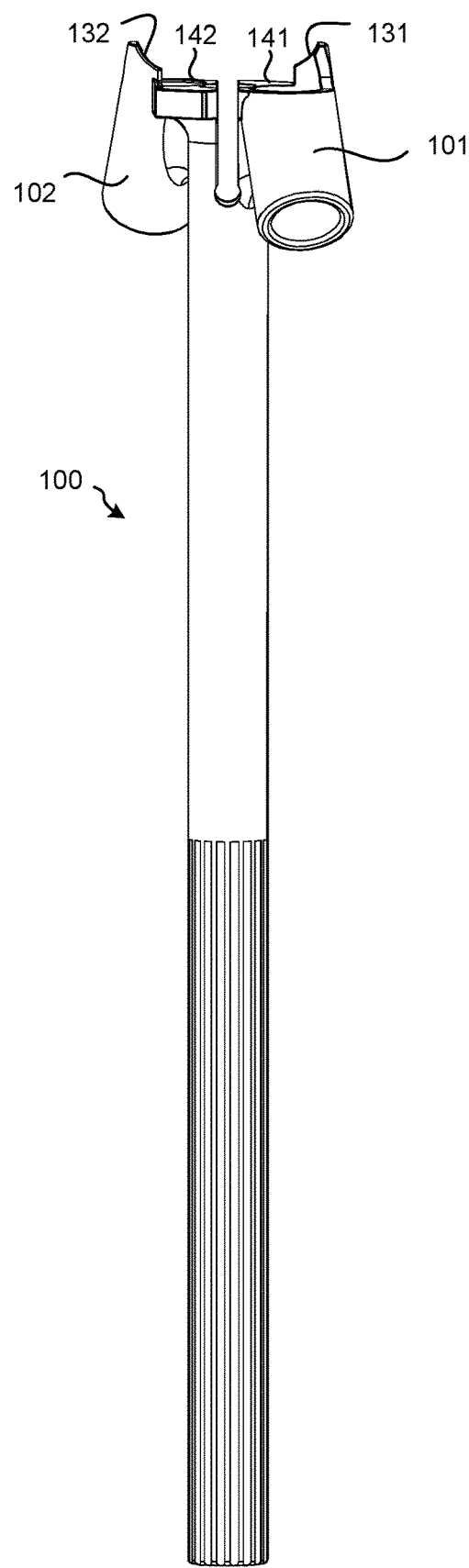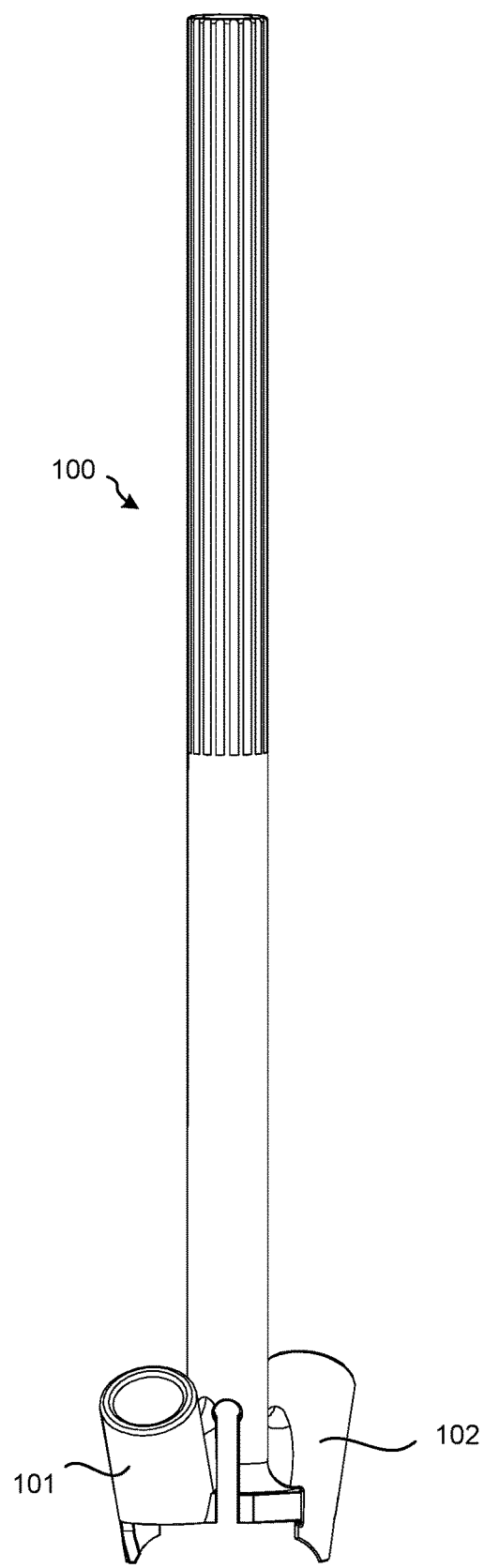
FIG. 1C  FIG. 1D

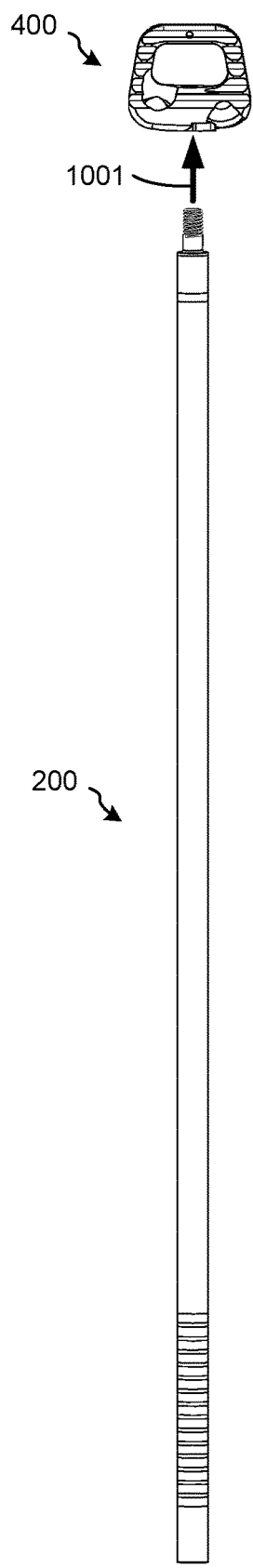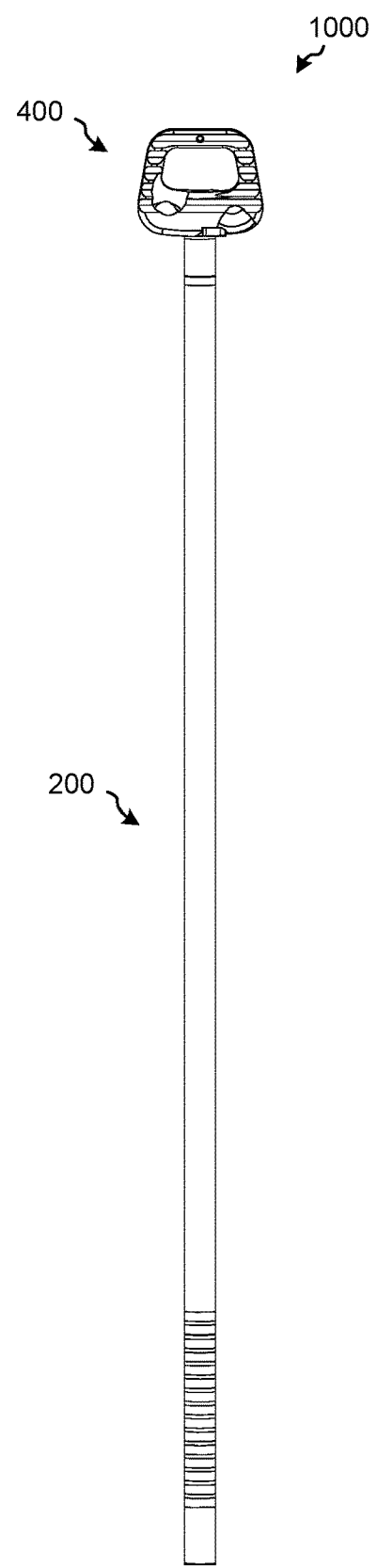
FIG. 10A  FIG. 10B

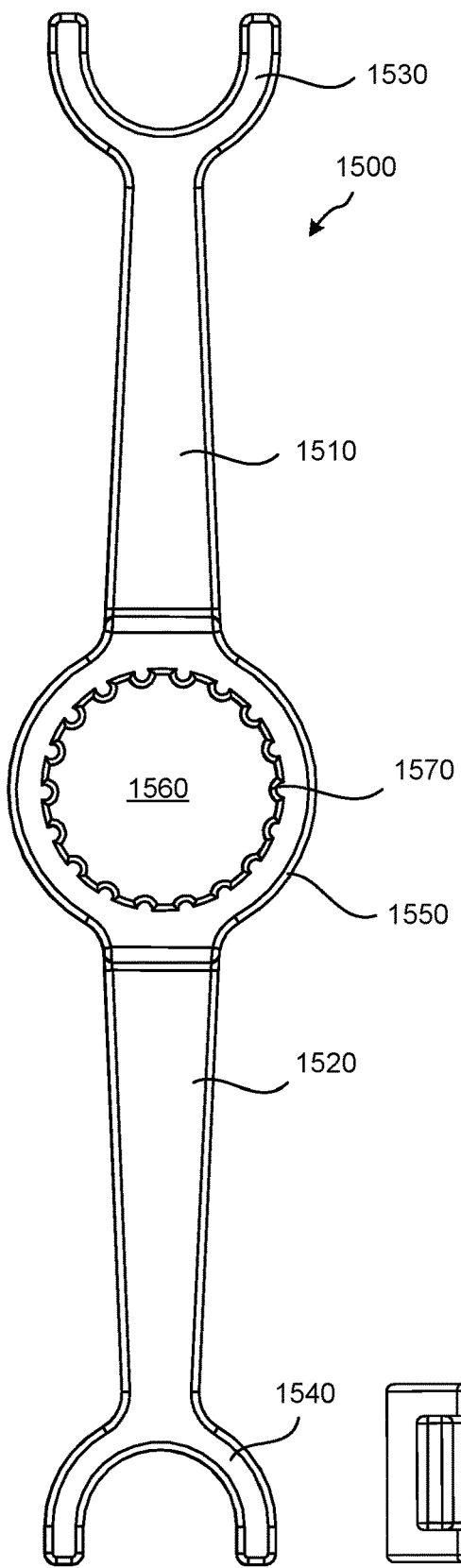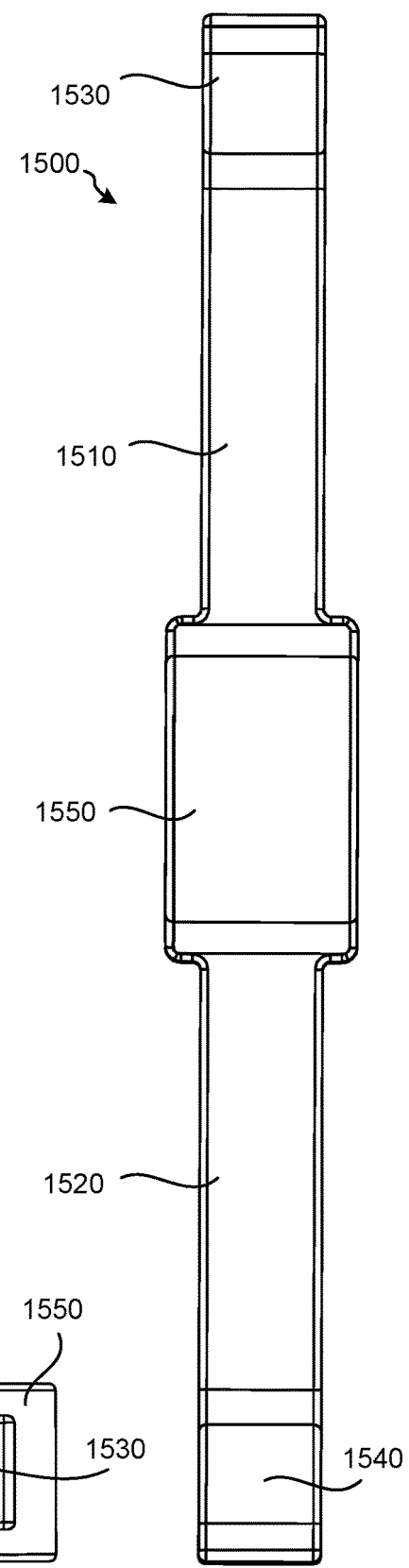
FIG. 15B    FIG. 15C    FIG. 15D

SPINAL SURGERY ASSEMBLIES, SYSTEMS, AND METHODS

CROSS-REFERENCE TO RELATED APPLICATIONS

This application is a continuation-in-part of U.S. patent application Ser. No. 16/695,952 entitled "SPINAL SURGERY DEVICES, SYSTEMS, AND METHODS," which was filed on Nov. 26, 2019, the disclosure of which is incorporated herein by reference in its entirety.

TECHNICAL FIELD

The present disclosure relates to surgical devices, instruments, assemblies, systems, and methods. More specifically, the present disclosure relates to improved surgical devices, instruments, assemblies, systems, and methods for implanting intervertebral spacers between adjacent vertebral bodies in a patient.

BACKGROUND

Spinal fixation procedures utilizing intervertebral spacers can be used to correct spinal conditions such as degenerative disc disease, spondylolisthesis, spinal deformities, or other spinal conditions through minimally invasive or invasive spinal surgery. For example, intervertebral discs can degenerate or otherwise become damaged over time. In some instances, an intervertebral spacer can be positioned within a space previously occupied by a disc between adjacent vertebral bodies. Such intervertebral spacers can help maintain a desired spacing between adjacent vertebrae and/or promote fusion between adjacent vertebrae. The use of bone graft and/or other materials within an intervertebral spacer can facilitate the fusion of adjacent vertebral bodies. One or more bone screws may also be utilized to help stabilize the intervertebral spacer during the fusion process.

During implantation, an intervertebral spacer may be provisionally placed between two vertebral bodies and then one or more bone tunnels may be formed within the vertebral bodies via an awl tool that projects through fastener channels formed in the intervertebral spacer. Bone screws may then be placed through the fastener channels and driven into the bone tunnels with a driver tool in order to secure the intervertebral spacer between the vertebral bodies.

However, the awl tool, the driver tool, and/or the bone screws may require guidance for proper insertion into the fastener channels of the intervertebral spacer. Accordingly, a need exists for improved surgical instrumentation, assemblies, systems, and methods.

SUMMARY

The various systems and methods of the present disclosure have been developed in response to the present state of the art, and in particular, in response to the problems and needs in the art that have not yet been fully solved by currently available surgical devices, instruments, assemblies, systems, and methods for implanting intervertebral spacers between two vertebral bodies of a patient.

According to some embodiments, an intervertebral spacer insertion system may include an intervertebral spacer and an insertion assembly comprising an inserter tool and a Drill, Tap, and Screw guide (hereinafter, "DTS guide"). The intervertebral spacer may include a superior surface configured to engage a superior vertebral body, an inferior surface configured to engage an inferior vertebral body, and a proximal surface. The proximal surface may include a first fastener channel configured to receive a first fastener, the first fastener channel oriented to pass through the proximal and superior surfaces of the intervertebral spacer at a first angle, a second fastener channel configured to receive a second fastener, the second fastener channel oriented to pass through the proximal and inferior surfaces of the intervertebral spacer at a second angle, and a locking member channel intermediate the first and second fastener channels. The locking member channel may include a first engagement feature formed therein. The inserter tool may include an inserter tool shaft and a second engagement feature formed on a distal end of the inserter tool shaft. The second engagement feature may be configured to engage the first engagement feature in order to removably couple the intervertebral spacer with the inserter tool. The DTS guide may include a DTS guide shaft and a DTS guide shaft lumen passing through the DTS guide shaft, the DTS guide shaft lumen configured to receive the inserter tool shaft therein to slidably couple the DTS guide with the inserter tool. The DTS guide may also include a first DTS guide member having a first DTS guide channel configured to receive the first fastener at the first angle to guide the first fastener into the first fastener channel of the intervertebral spacer. The DTS guide may further include a second DTS guide member having a second DTS guide channel configured to receive the second fastener at the second angle to guide the second fastener into the second fastener channel of the intervertebral spacer. The DTS guide may additionally include a first DTS guide wing proximate the first DTS guide member, the first DTS guide wing configured to abut against a first surface of the intervertebral spacer, and a second DTS guide wing proximate the second DTS guide member, the second DTS guide wing configured to abut against a second surface of the intervertebral spacer. The first and second DTS guide wings may be configured to align the first and second DTS guide channels with respect to the first and second fastener channels, independently of any additional apertures or recesses formed in the intervertebral spacer, in order to respectively guide the first and second fasteners through the first and second DTS guide channels and into the first and second fastener channels of the intervertebral spacer.

In some embodiments of the intervertebral spacer insertion system, the first engagement feature may comprise first threading and the second engagement feature may comprise second threading.

In some embodiments of the intervertebral spacer insertion system, the inserter tool shaft may comprise at least one engagement surface configured to engage at least one complementarily shaped lumen engagement surface formed in the DTS guide shaft lumen in order to orient the DTS guide relative to the inserter tool.

In some embodiments of the intervertebral spacer insertion system, the insertion assembly may further comprise a handle that is removably couplable with the inserter tool, the handle comprising at least one handle engagement surface configured to engage the at least one engagement surface of the inserter tool shaft to stabilize the handle relative to the inserter tool.

In some embodiments of the intervertebral spacer insertion system, the inserter tool shaft may comprise a ridge configured to couple with a recess formed within the DTS guide shaft lumen to prevent the DTS guide from slidably translating relative to the inserter tool.

In some embodiments of the intervertebral spacer insertion system, the inserter tool may comprise at least one guide fin and the DTS guide shaft may comprise a DTS guide fin slot configured to receive the at least one guide fin to orient the DTS guide relative to the inserter tool.

In some embodiments of the intervertebral spacer insertion system, the DTS guide may comprise at least one depth stop surface configured to prevent over-insertion of the intervertebral spacer between two vertebral bodies of a patient.

In other embodiments, an insertion assembly may include an inserter tool and a DTS guide. The insertion assembly may be configured to couple with an intervertebral spacer. The intervertebral spacer may include a superior surface configured to engage a superior vertebral body, an inferior surface configured to engage an inferior vertebral body, and a peripheral wall extending from the superior surface to the inferior surface. The peripheral wall may include a fastener channel configured to receive a fastener, the fastener channel oriented to pass through the peripheral wall and the superior or inferior surface of the intervertebral spacer, as well as a locking member channel adjacent the fastener channel comprising a first engagement feature. The inserter tool may include an inserter tool shaft and a second engagement feature formed on a distal end of the inserter tool shaft. The second engagement feature may be configured to engage the first engagement feature of the locking member channel to removably couple the inserter tool with the intervertebral spacer. The DTS guide may include a DTS guide shaft and a DTS guide shaft lumen passing through the DTS guide shaft and configured to receive the inserter tool shaft therein in order to slidably couple the DTS guide to the inserter tool. The DTS guide may also include a DTS guide member coupled to a distal end of the DTS guide shaft, the DTS guide member comprising a DTS guide channel formed through the DTS guide member and configured to receive the fastener. The DTS guide may further include a DTS guide wing proximate the DTS guide member. The DTS guide wing may be configured to abut against a surface of the peripheral wall to align the DTS guide channel with respect to the fastener channel in order to guide the fastener through the DTS guide channel and into the fastener channel of the intervertebral spacer.

In some embodiments of the insertion assembly, the first engagement feature may comprise first threading and the second engagement feature may comprise second threading.

In some embodiments of the insertion assembly, the inserter tool shaft may comprise at least one engagement surface configured to engage at least one complementarily shaped lumen engagement surface formed in the DTS guide shaft lumen in order to orient the DTS guide relative to the inserter tool.

In some embodiments of the insertion assembly, the insertion assembly may further comprise a handle that is removably couplable with the inserter tool, the handle comprising at least one handle engagement surface configured to engage the at least one engagement surface of the inserter tool shaft to stabilize the handle relative to the inserter tool.

In some embodiments of the insertion assembly, the inserter tool shaft may comprise a ridge configured to couple with a recess formed within the DTS guide shaft lumen to prevent the DTS guide from slidably translating relative to the inserter tool.

In some embodiments of the insertion assembly, the inserter tool may comprise at least one guide fin and the DTS guide shaft may comprise a DTS guide fin slot configured to receive the at least one guide fin to orient the DTS guide relative to the inserter tool.

In some embodiments of the insertion assembly, the DTS guide wing may align the DTS guide channel with respect to the fastener channel, independently of any additional apertures or recesses formed in the intervertebral spacer.

In yet other embodiments, a method of assembling an insertion assembly and an intervertebral spacer may include coupling the intervertebral spacer to the insertion assembly. The intervertebral spacer may include a superior surface configured to engage a superior vertebral body, an inferior surface configured to engage an inferior vertebral body, and a peripheral wall extending from the superior surface to the inferior surface. The peripheral wall may include a fastener channel configured to receive a fastener, the fastener channel oriented to pass through the peripheral wall and the superior or inferior surface of the intervertebral spacer, and a locking member channel adjacent the fastener channel and comprising a first engagement feature formed therein. The method may include engaging a second engagement feature of an inserter tool with the first engagement feature of the locking member channel to couple the inserter tool to the intervertebral spacer. The method may also include inserting a proximal end of an inserter tool shaft into a distal opening of a DTS guide shaft lumen of a DTS guide to slidably couple the DTS guide to the inserter tool. The method may further include aligning a DTS guide channel of the DTS guide with respect to the fastener channel of the intervertebral spacer via a DTS guide wing coupled to the DTS guide, the DTS guide wing configured to abut against a surface of the peripheral wall to align the DTS guide channel with respect to the fastener channel in order to guide the fastener through the DTS guide channel and into the fastener channel of the intervertebral spacer.

In some embodiments, the method may further comprise inserting a proximal end of the inserter tool shaft into a distal opening of a handle to couple the handle to the inserter tool.

In some embodiments, the method may further comprise manipulating the handle coupled to the inserter tool to insert the intervertebral spacer between two vertebral bodies of a patient.

In some embodiments, the method may further comprise drilling a bone tunnel in a vertebral body of the patient with an awl tool guided through the DTS guide channel and into the fastener channel of the intervertebral spacer.

In some embodiments, the method may further comprise driving a bone screw into the vertebral body of the patient with a driver tool guided through the DTS guide channel and into the fastener channel of the intervertebral spacer.

In some embodiments, the method may further comprise disengaging the second engagement feature of the inserter tool from the first engagement feature of the locking member channel to uncouple the inserter tool from the intervertebral spacer and removing the inserter tool from the patient.

These and other features and advantages of the present disclosure will become more fully apparent from the following description and appended claims, or may be learned by the practice of the systems and methods set forth hereinafter.

BRIEF DESCRIPTION OF THE DRAWINGS

Exemplary embodiments of the disclosure will become more fully apparent from the following description and appended claims, taken in conjunction with the accompanying drawings. Understanding that these drawings depict only exemplary embodiments and are, therefore, not to be considered limiting of the scope of the appended claims, the exemplary embodiments of the present disclosure will be described with additional specificity and detail through use of the accompanying drawings in which:

FIG. 1C is a top view of the DTS guide of FIG. 1A;

FIG. 1D is a bottom view of the DTS guide of FIG. 1A;

FIG. 10A illustrates an insertion assembly, including the inserter tool and the intervertebral spacer, prior to assembly;

FIG. 10B illustrates the insertion assembly after assembly;

FIG. 15B is a front side view of the U-support tool of FIG. 15A;

FIG. 15C is a top view of the U-support tool of FIG. 15A;

FIG. 15D is a left side view of the U-support tool of FIG. 15A;

Figure 1A:
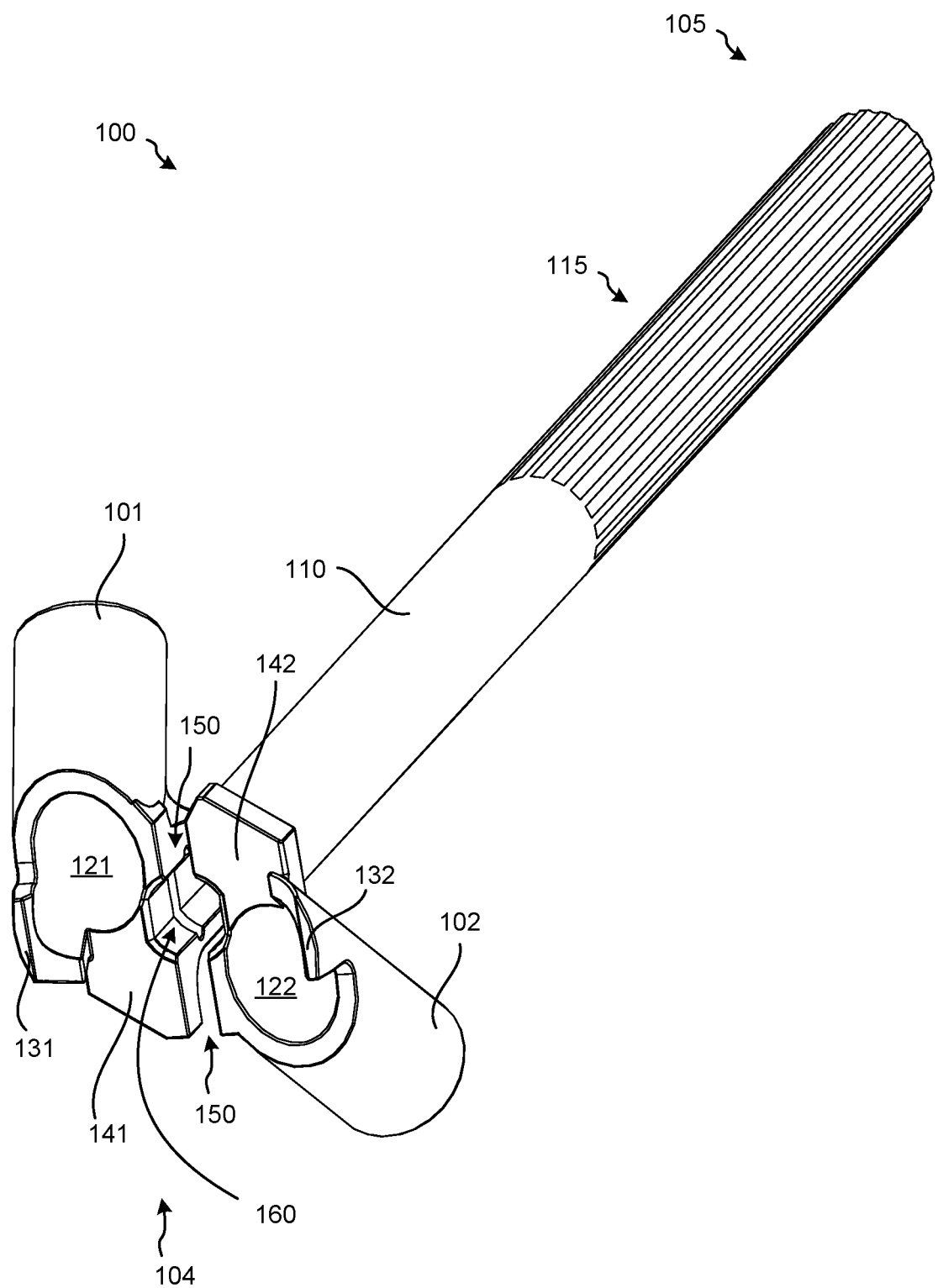
FIG. 1A is a perspective top view of a DTS guide, according to an embodiment of the present disclosure.

It is to be understood that the drawings are for purposes of illustrating the concepts of the disclosure and may not be drawn to scale. Furthermore, the drawings illustrate exemplary embodiments and do not represent limitations to the scope of the present disclosure.

DETAILED DESCRIPTION

Exemplary embodiments of the present disclosure will be best understood by reference to the drawings, wherein like parts are designated by like numerals throughout. It will be readily understood that the components of the present disclosure, as generally described and illustrated in the Figures herein, could be arranged and designed in a wide variety of different configurations. Thus, the following more detailed description of the embodiments of the apparatus and method, as represented in the Figures, is not intended to limit the scope of the present disclosure, as claimed in this or any other application claiming priority to this application, but is merely representative of exemplary embodiments of the present disclosure.

Standard medical directions, planes of reference, and descriptive terminology are employed in this specification. For example, anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body. Ipsilateral means on the same side of the body. Contralateral means on the opposite side of the body. A sagittal plane divides a body into right and left portions. A midsagittal plane divides the body into bilaterally symmetric right and left halves. A coronal plane divides a body into anterior and posterior portions. A transverse plane divides a body into superior and inferior portions. These descriptive terms may be applied to an animate or inanimate body.

The phrases "connected to," "coupled to," "engaged with," and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Figure 1B:
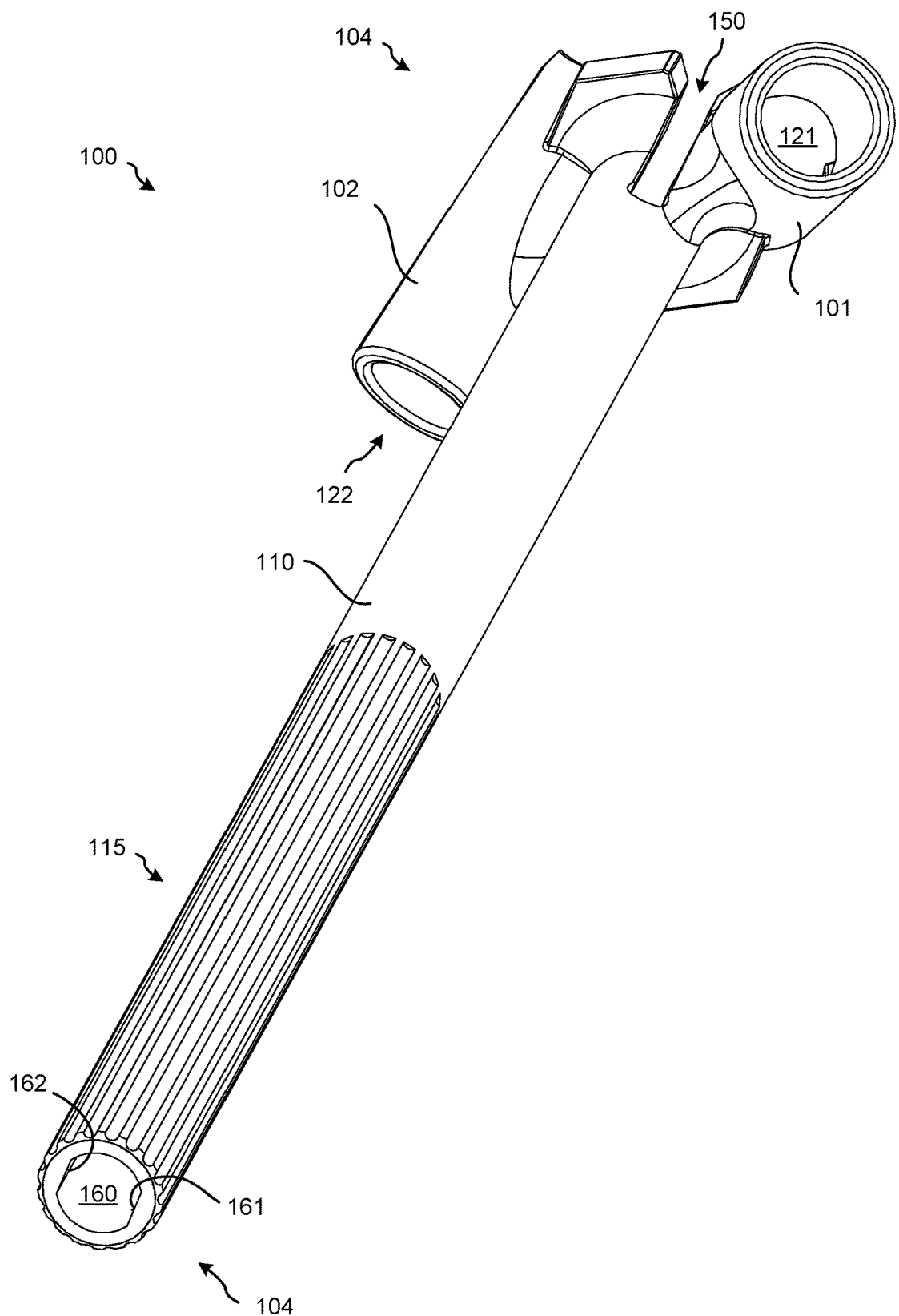
FIG. 1B is a perspective bottom view of the DTS guide of FIG. 1A.
Figure 1E:
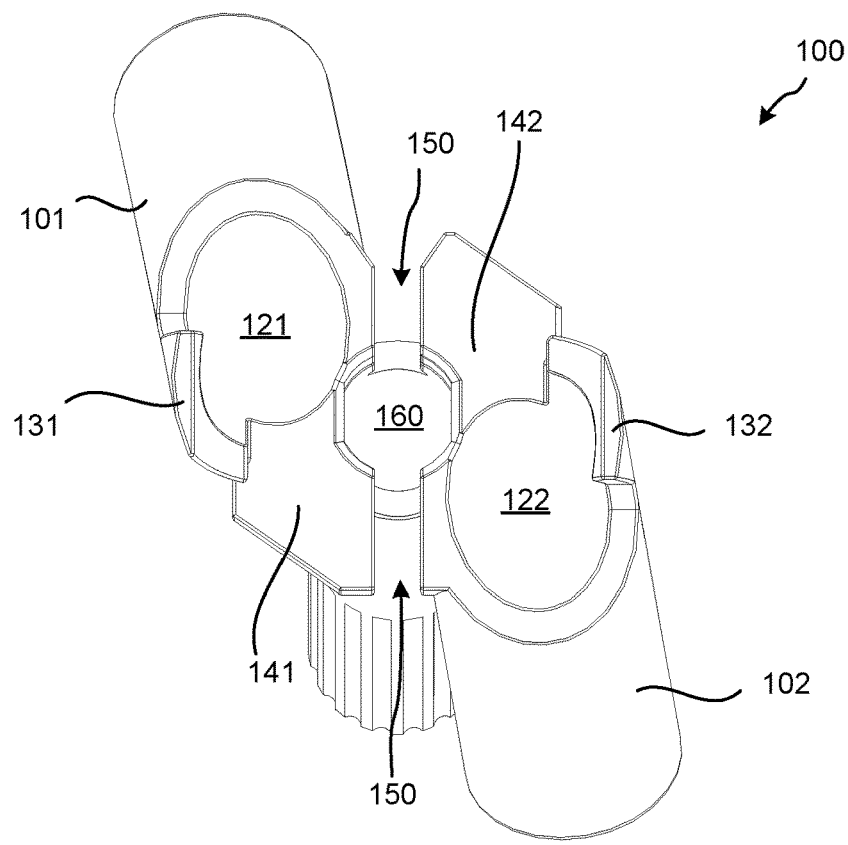
FIG. 1E is a proximal end view of the DTS guide of FIG. 1A.
Figure 1F:
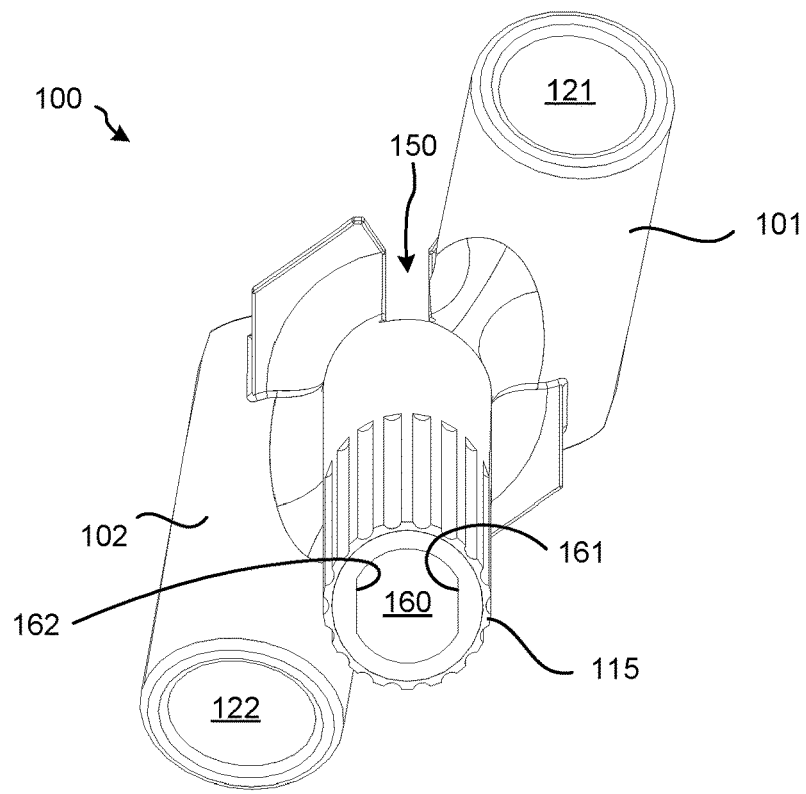
FIG. 1F is a distal end view of the DTS guide of FIG. 1A.

FIGS. 1A-1F illustrate various views of a DTS guide 100, according to an embodiment of the present disclosure. Specifically, FIG. 1A is a perspective top view of the DTS guide 100; FIG. 1B is a perspective bottom view of the DTS guide 100; FIG. 1C is a top view of the DTS guide 100; FIG. 1D is a bottom view of the DTS guide 100; FIG. 1E is a proximal end view of the DTS guide 100; and FIG. 1F is a distal end view of the DTS guide 100. The DTS guide 100 may generally include a proximal end 105, a distal end 104, a shaft 110, a first DTS guide member 101 having a first DTS guide channel 121 oriented at a first angle, a second DTS guide member 102 having a second DTS guide channel 122 oriented at a second angle, a DTS guide fin slot 150 intermediate the first and second DTS guide members 101, 102, a first DTS guide wing 131, a second DTS guide wing 132, a first depth stop surface 141, a second depth stop surface 142, and one or more shaft splines 115, which will be discussed in more detail below with respect to FIGS. 16A and 16B.

In at least one embodiment, the shaft 110 of the DTS guide 100 may be hollow and have a "double D" shaped DTS guide shaft lumen 160 with a first lumen engagement surface 161 and a second lumen engagement surface 162 configured to receive a correspondingly shaped inserter tool (e.g., see FIGS. 2A-2E). However, in other embodiments, the DTS guide shaft lumen 160 may have a circular shape configured to receive an inserter tool shaft having a complementary circular shape (e.g., see FIGS. 3A-3E). In yet other embodiments (not shown), the DTS guide shaft lumen 160 may have any shape configured to receive an inserter tool with a complementarily shaped shaft. Operation of the DTS guide 100 with respect to other assembly/system components will be described in more detail below with respect to FIGS. 10A-12B.

Figure 2A:
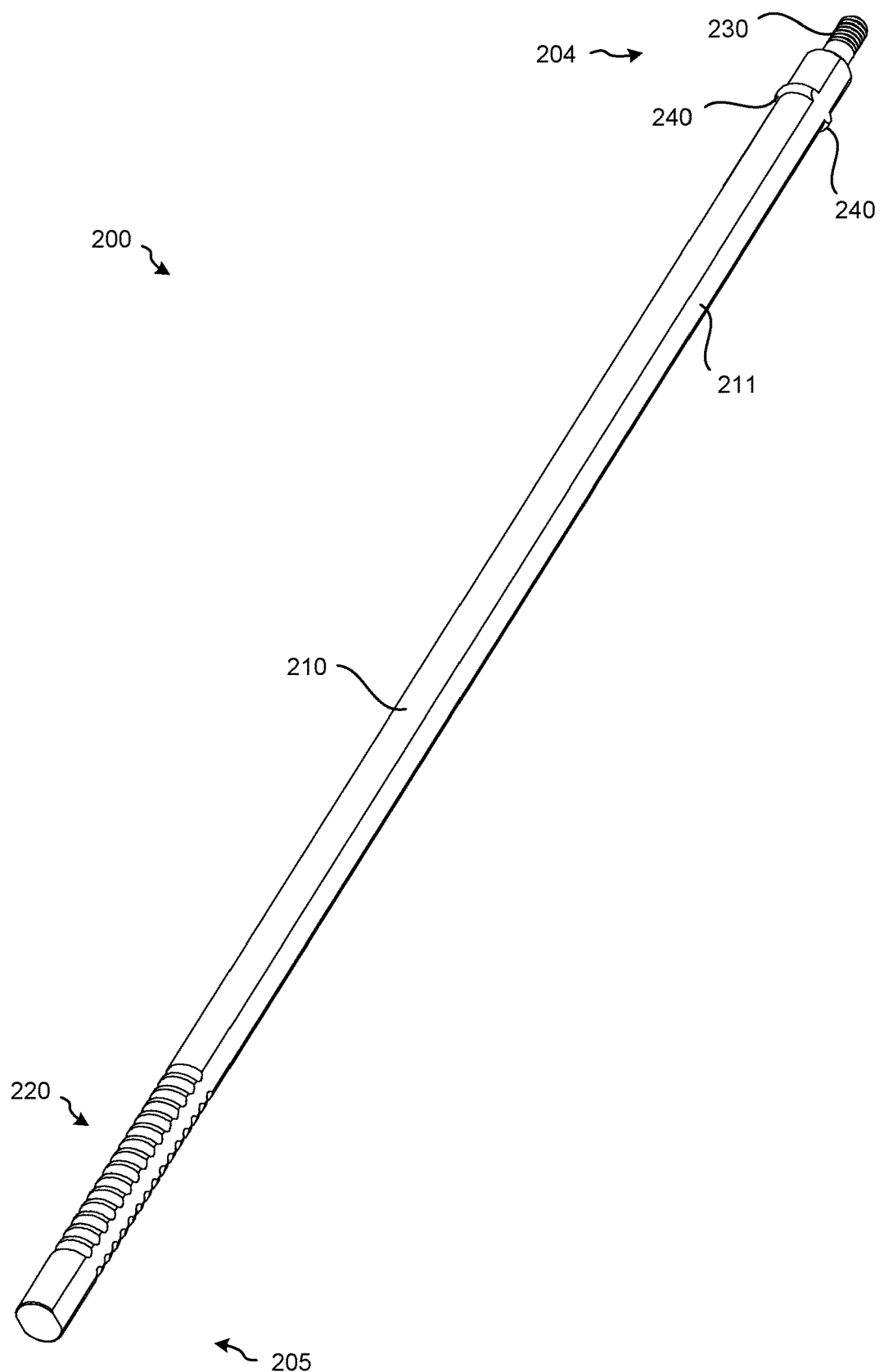
FIG. 2A is a perspective top view of an inserter tool, according to an embodiment of the present disclosure.
Figure 2B:
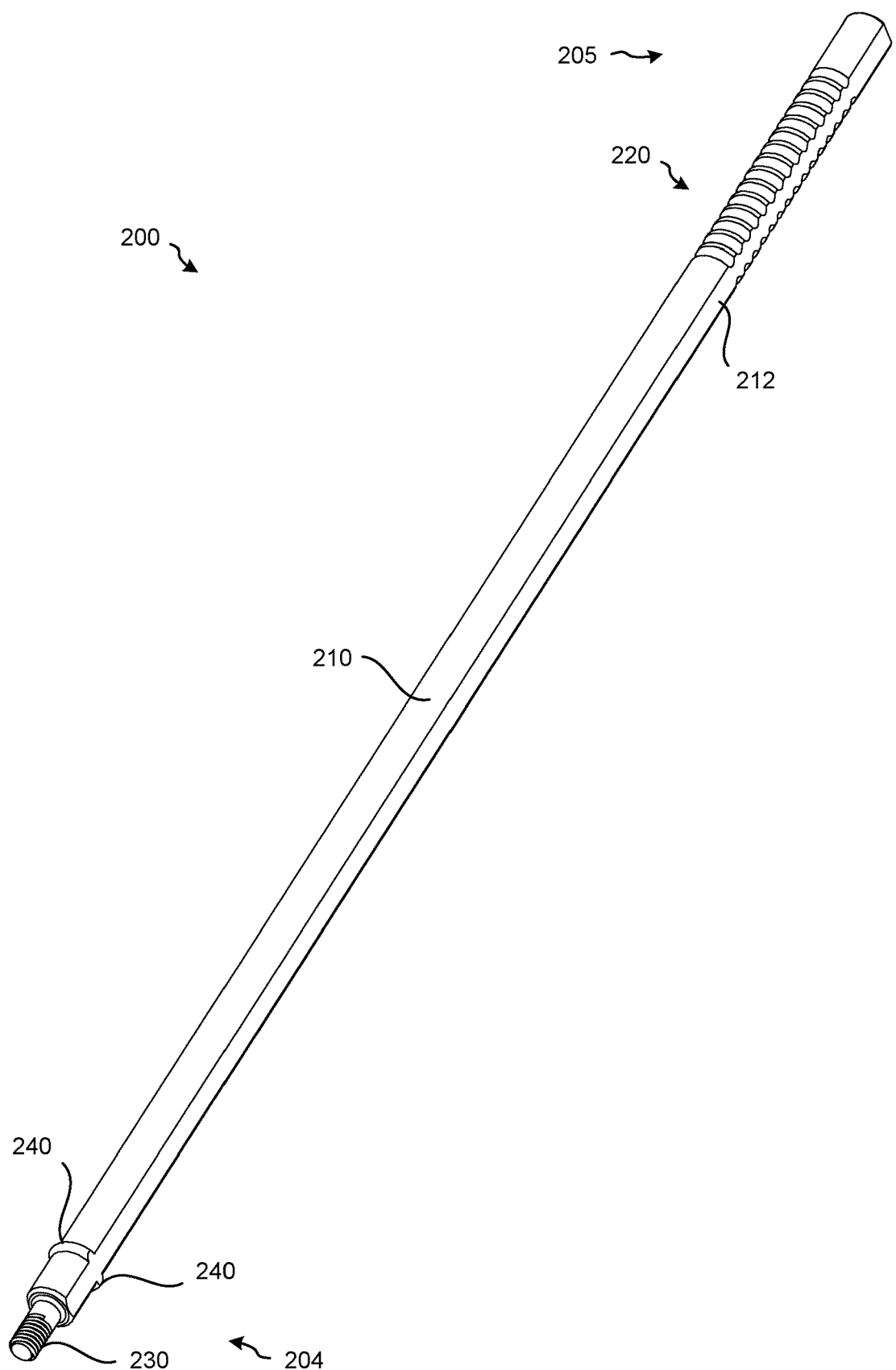
FIG. 2B is a perspective bottom view of the inserter tool of FIG. 2A.
Figures 2C, 2D, 2E:
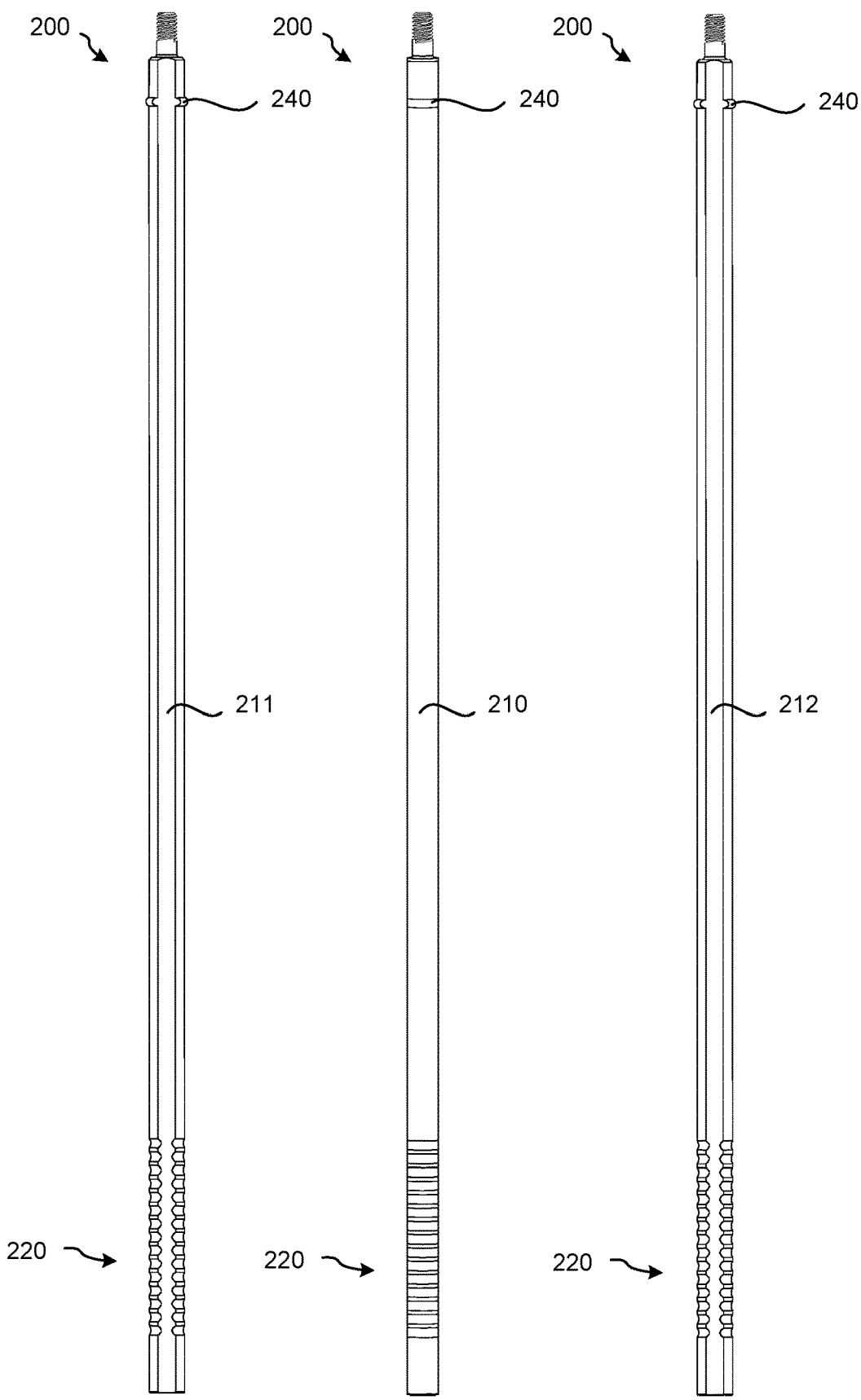
FIG. 2C is a top view of the inserter tool of FIG. 2A.
FIG. 2D is a side view of the inserter tool of FIG. 2A.
FIG. 2E is a bottom view of the inserter tool of FIG. 2A.

FIGS. 2A-2E illustrate various views of an inserter tool 200, according to an embodiment of the present disclosure. Specifically, FIG. 2A is a perspective top view of the inserter tool 200; FIG. 2B is a perspective bottom view of the inserter tool 200; FIG. 2C is a top view of the inserter tool 200; FIG. 2D is a side view of the inserter tool 200; and FIG. 2E is a bottom view of the inserter tool 200. The inserter tool 200 may generally include a shaft 210 having a proximal end 205, a distal end 204, a first engagement surface 211, a second engagement surface 212, recesses 220, ridges 240, and second threading 230 disposed at the distal end 204 of the shaft 210. Operation of the inserter tool 200 with respect to other assembly/system components will be described in more detail below with respect to FIGS. 10A-11C and 13A-21.

Figure 3A:
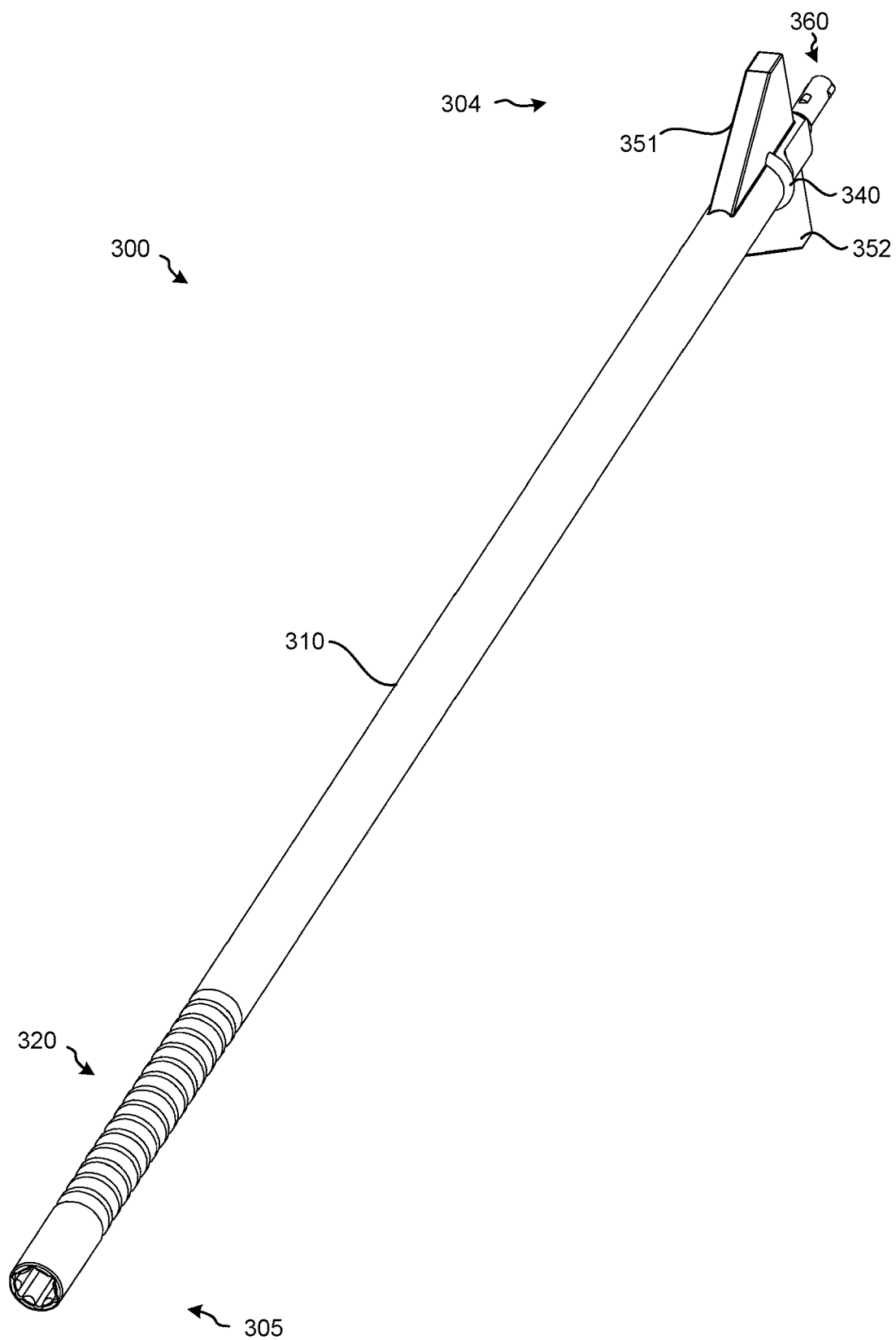
FIG. 3A is a perspective top view of an inserter tool, according to another embodiment of the present disclosure.
Figure 3B:
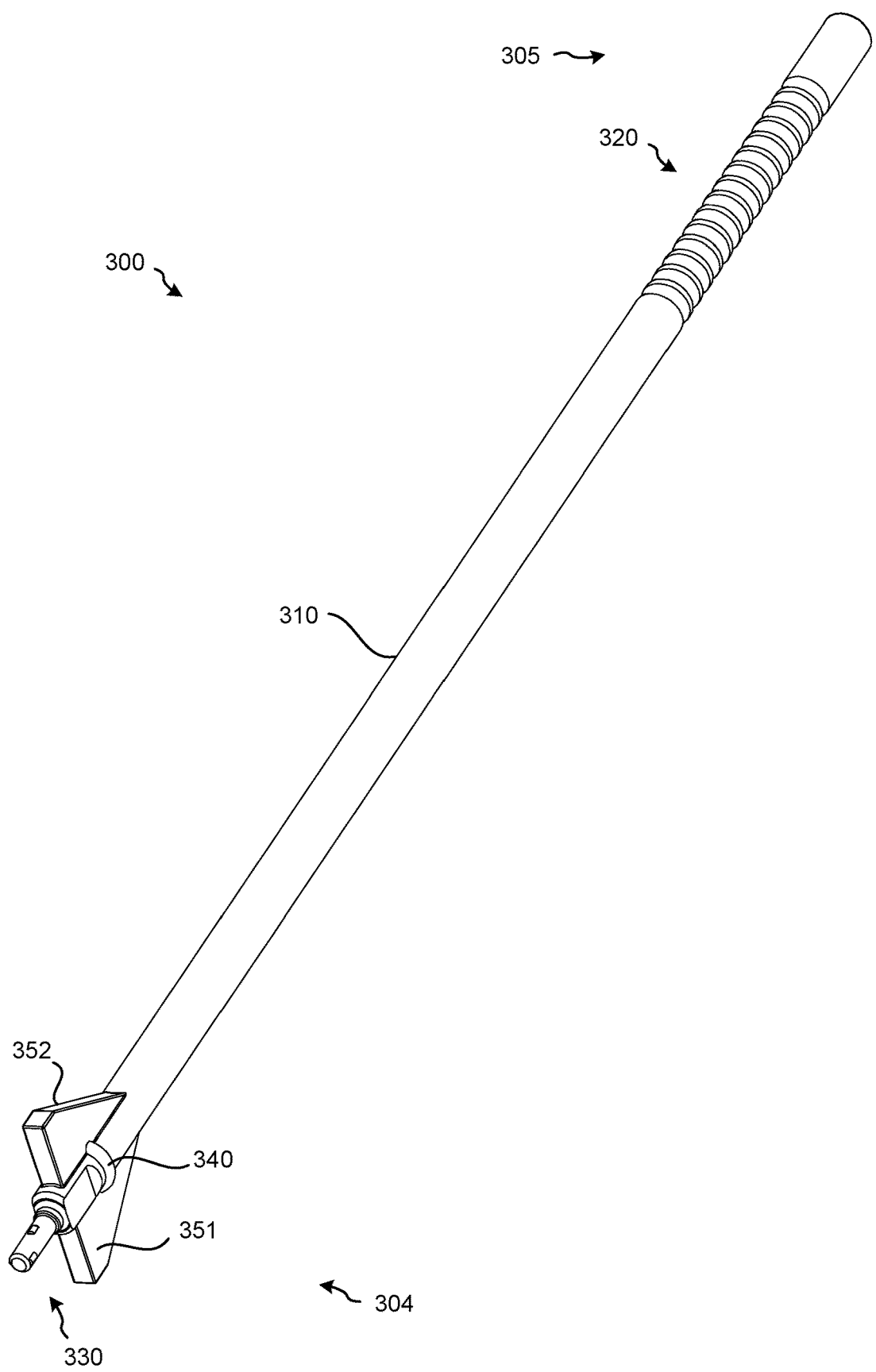
FIG. 3B is a perspective bottom view of the inserter tool of FIG. 3A.
Figures 3C, 3D, 3E:
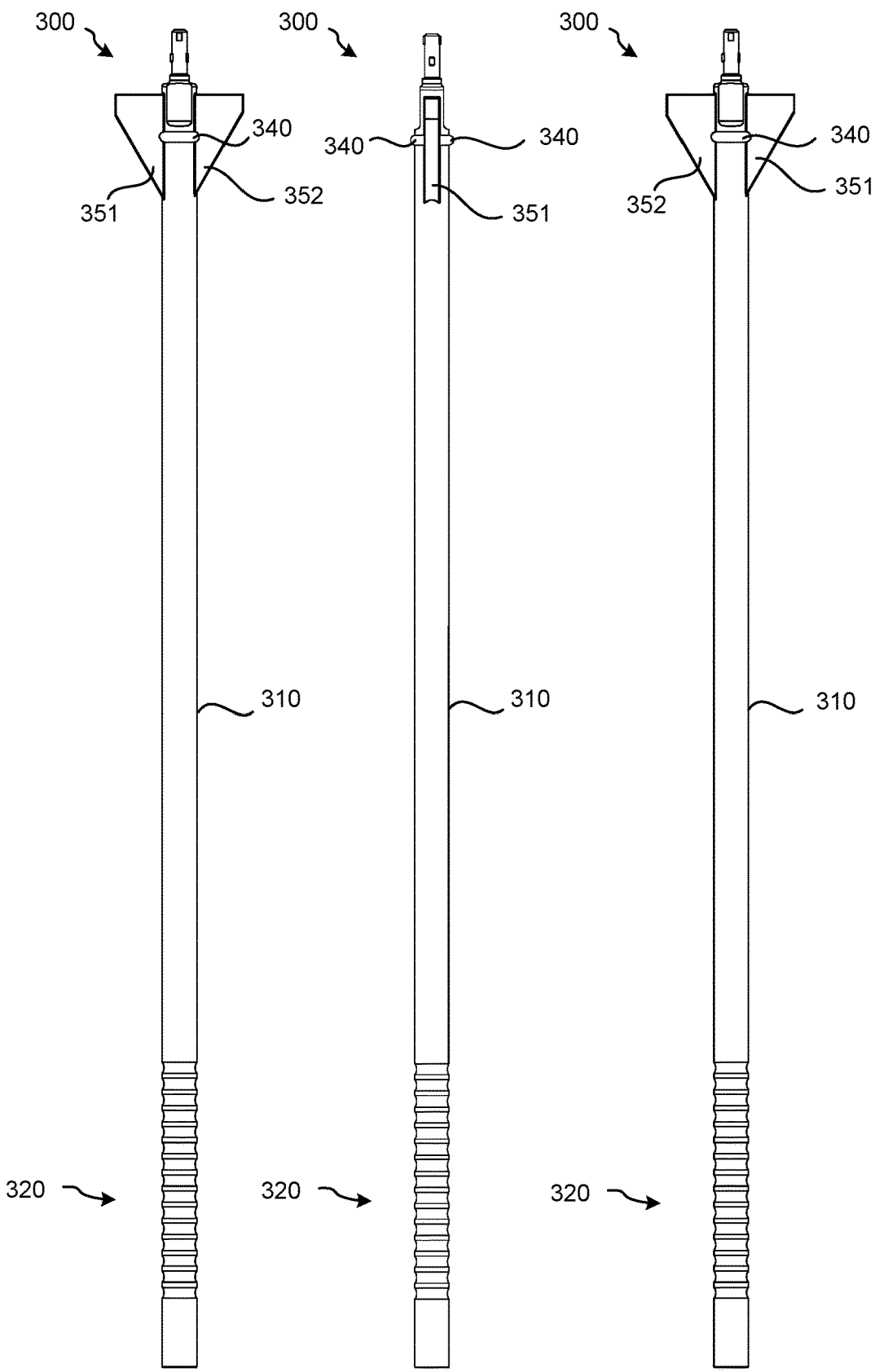
FIG. 3C is a right side view of the inserter tool of FIG. 3A.
FIG. 3D is a top view of the inserter tool of FIG. 3A.
FIG. 3E is a left side view of the inserter tool of FIG. 3A.

FIGS. 3A-3E illustrate various views of an inserter tool 300, according to an embodiment of the present disclosure. Specifically, FIG. 3A is a perspective top view of the inserter tool 300; FIG. 3B is a perspective bottom view of the inserter tool 300; FIG. 3C is a right side view of the inserter tool 300; FIG. 3D is a top view of the inserter tool 300; and FIG. 3E is a left side view of the inserter tool 300. The inserter tool 300 may generally include a shaft 310 having a proximal end 305, a distal end 304, recesses 320, ridges 340, a first guide fin 351, a second guide fin 352, and an engagement feature 360 disposed at the distal end 304 of the shaft 310. Operation of the inserter tool 300 with respect to other assembly/system components will be described in more detail below with respect to FIGS. 12A and 12B.

Figure 4A:
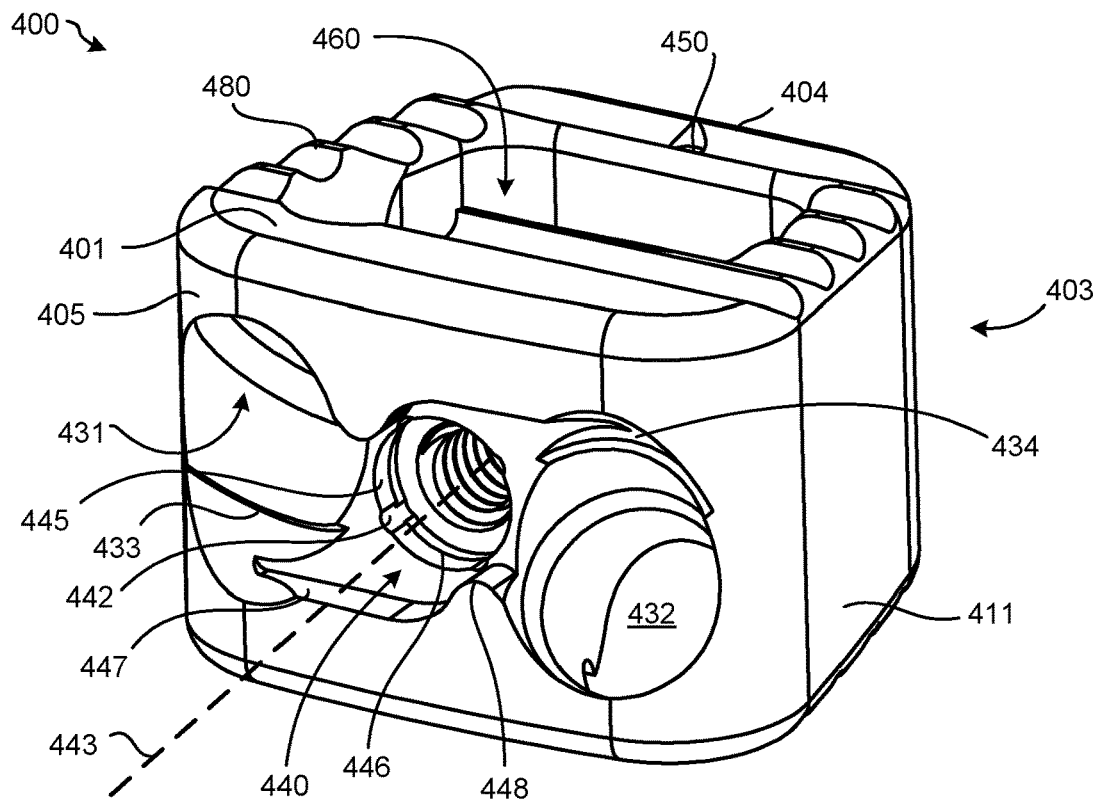
FIG. 4A is a perspective top view of a proximal end of an intervertebral spacer, according to an embodiment of the present disclosure.
Figure 4B:
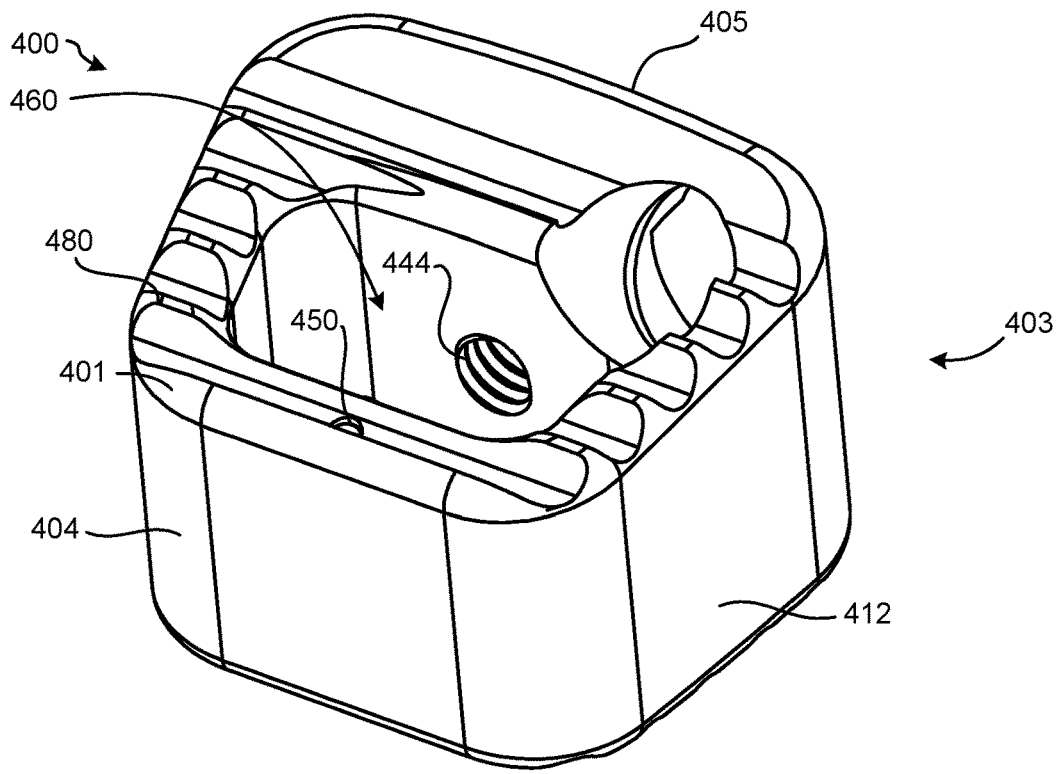
FIG. 4B is a perspective top view of a distal end of the intervertebral spacer of FIG. 4A.
Figure 4C:
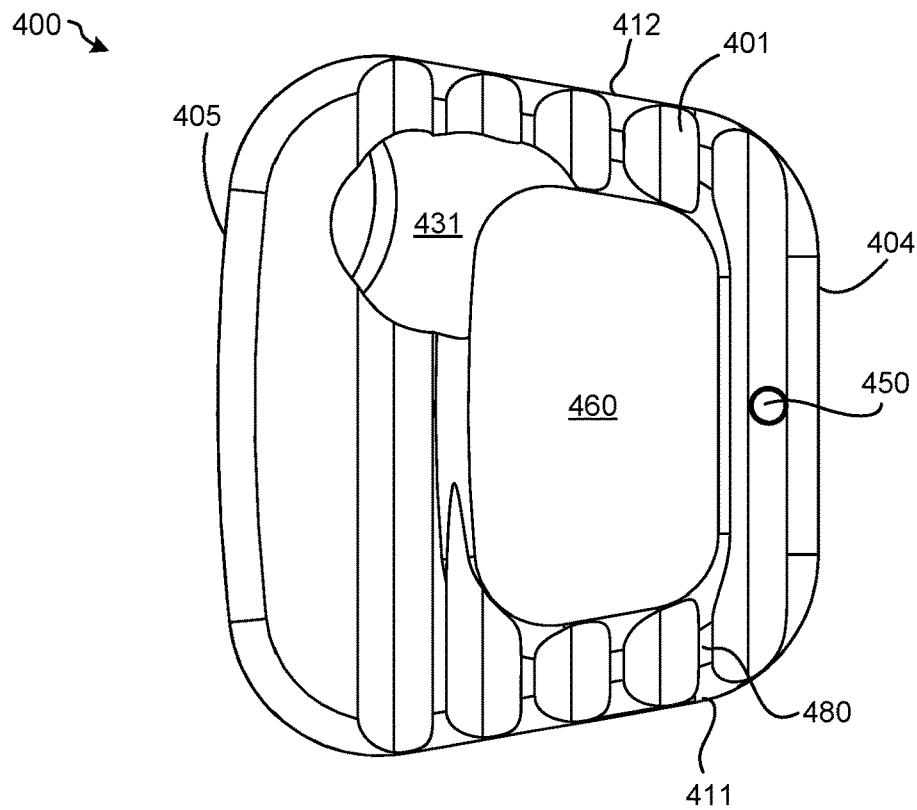
FIG. 4C is a top view of the intervertebral spacer of FIG. 4A.
Figure 4D:
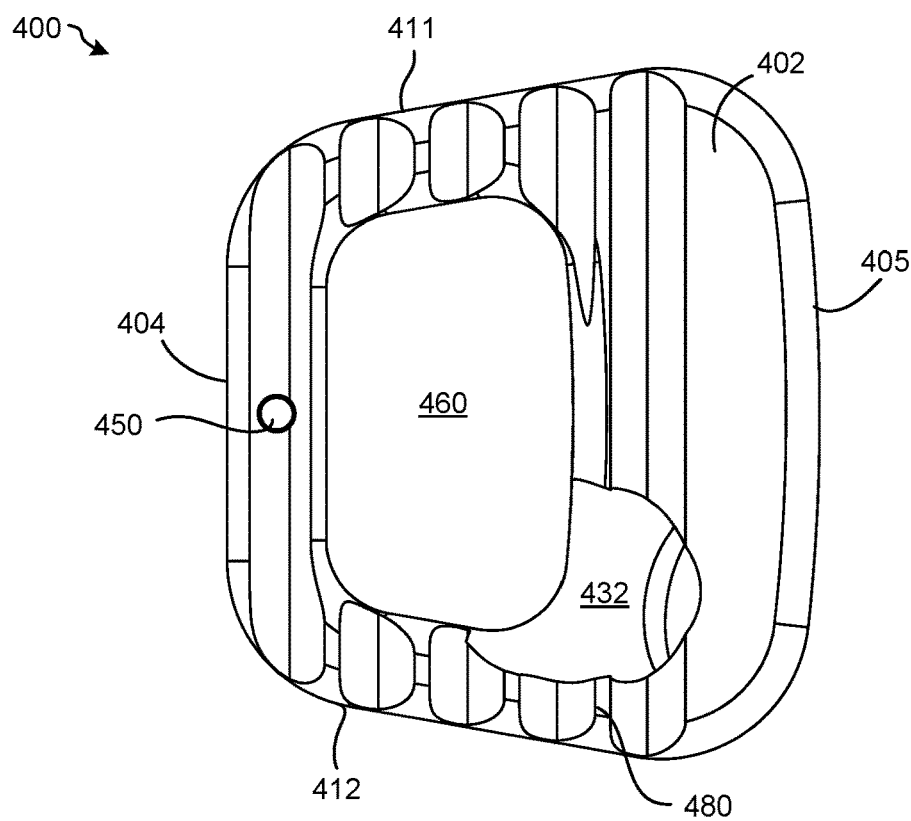
FIG. 4D is a bottom view of the intervertebral spacer of FIG. 4A.
Figure 4E:
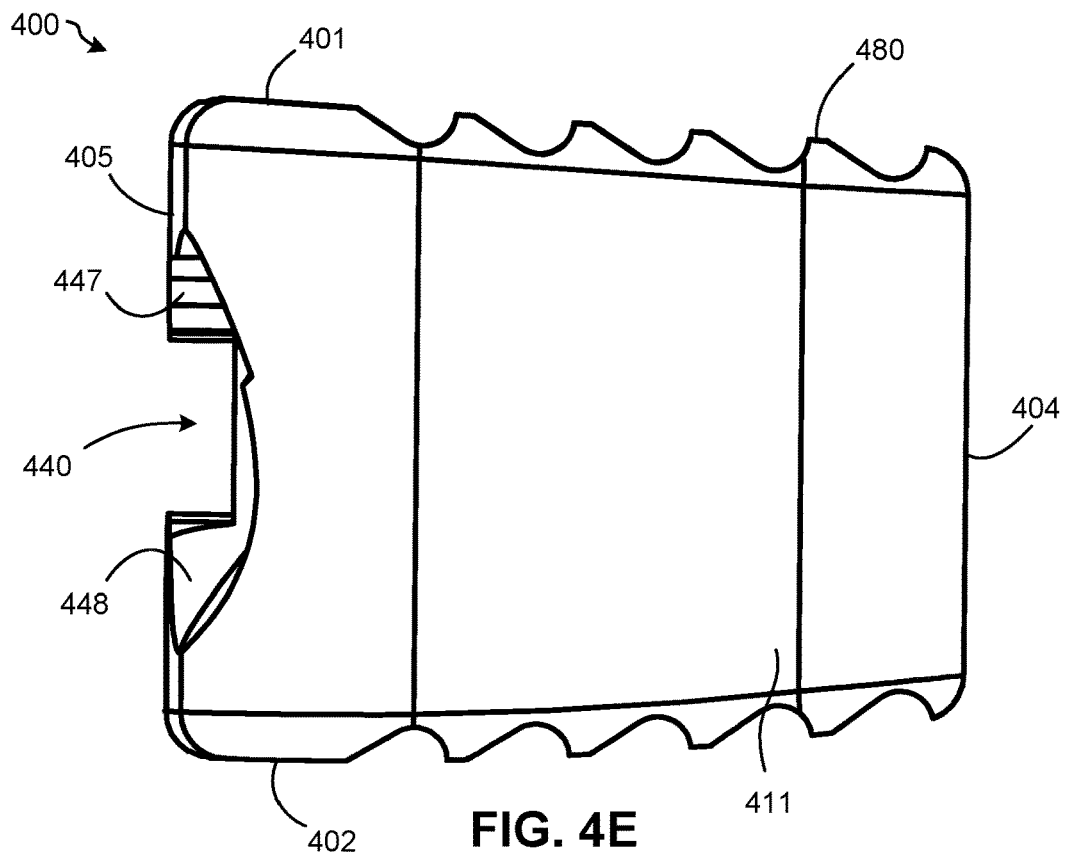
FIG. 4E illustrates a first side of the intervertebral spacer of FIG. 4A.
Figure 4F:
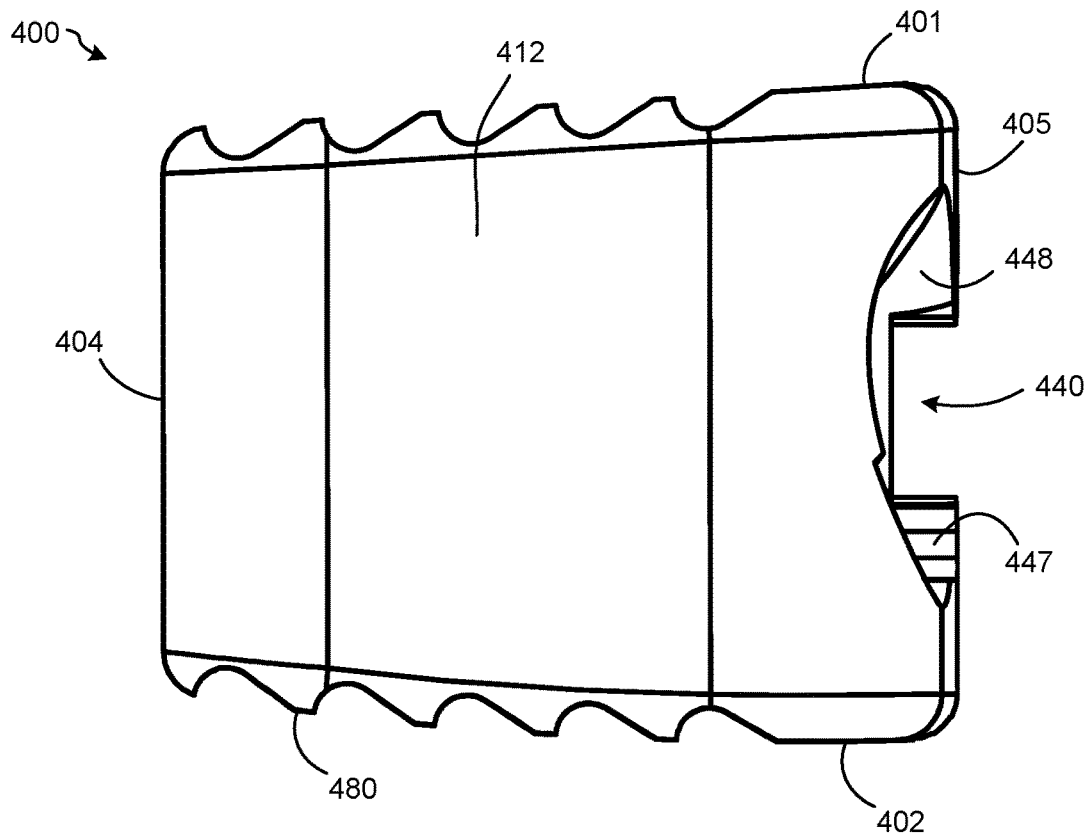
FIG. 4F illustrates a second side of the intervertebral spacer of FIG. 4A.
Figure 4G:
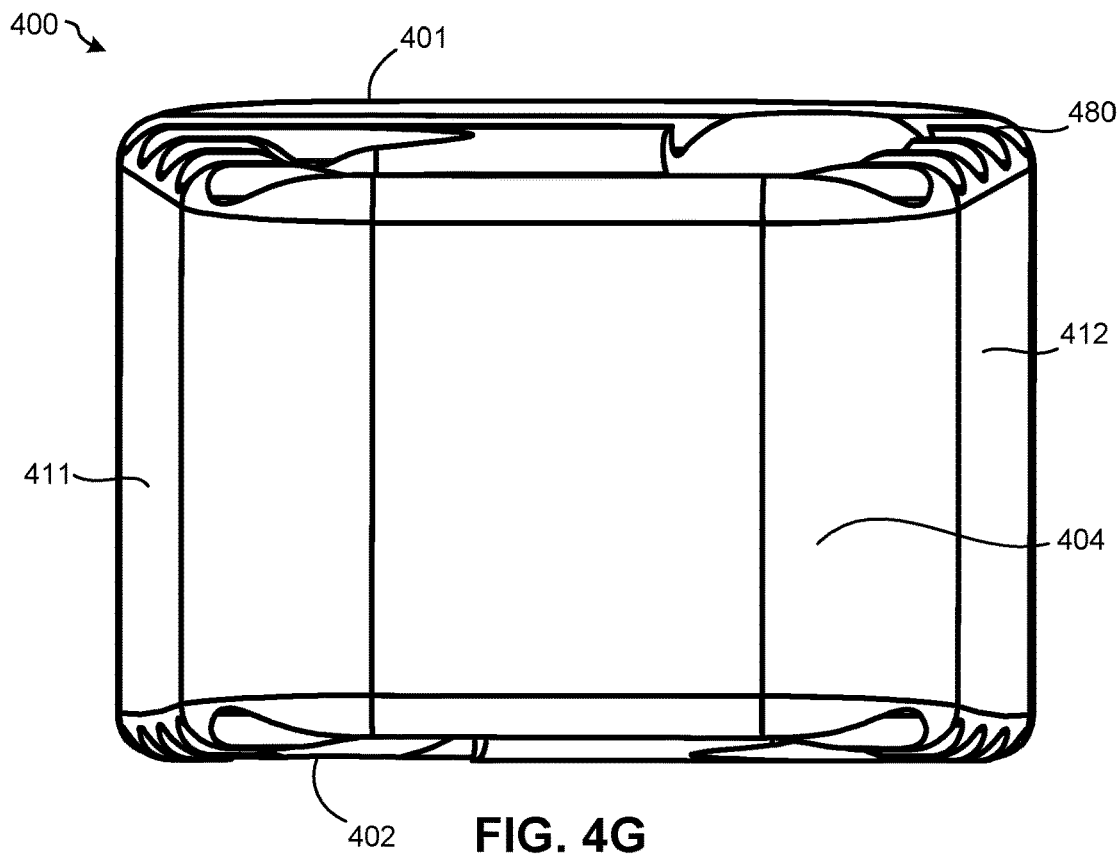
FIG. 4G illustrates a distal end view of the intervertebral spacer of FIG. 4A.
Figure 4H:
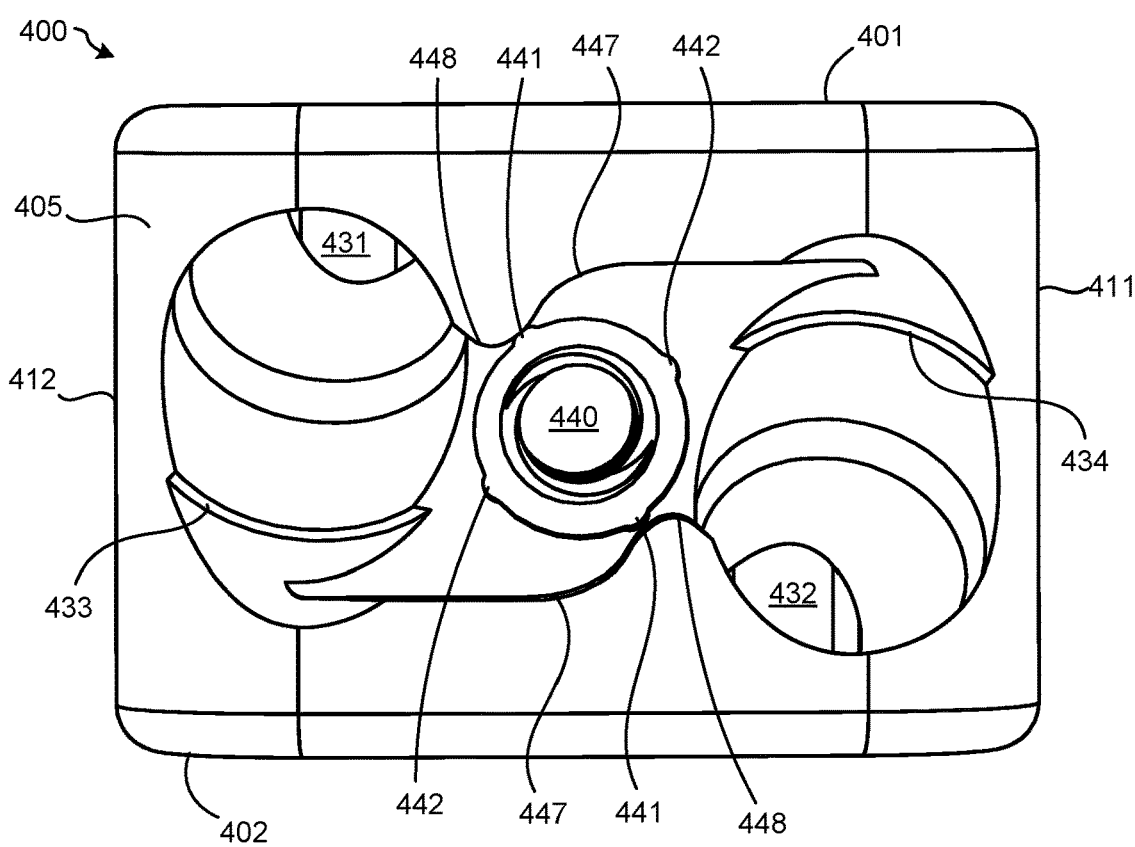
FIG. 4H illustrates a proximal end view of the intervertebral spacer of FIG. 4A.

FIGS. 4A-4H illustrate various views of an intervertebral spacer 400, according to an embodiment of the present disclosure. Specifically, FIG. 4A is a perspective top view of a proximal end 405 or a proximal surface of the intervertebral spacer 400; FIG. 4B is a perspective top view of a distal end 404 of the intervertebral spacer 400; FIG. 4C is a top view of the intervertebral spacer 400; FIG. 4D is a bottom view of the intervertebral spacer 400; FIG. 4E illustrates a first side 411 of the intervertebral spacer 400; FIG. 4F illustrates a second side 412 of the intervertebral spacer 400; FIG. 4G illustrates a distal end view of the intervertebral spacer 400; and FIG. 4H illustrates a proximal end view of the intervertebral spacer 400.

The intervertebral spacer 400 may generally include a superior surface 401 configured to engage a superior vertebral body (not shown), an inferior surface 402 configured to engage an inferior vertebral body (not shown), and a peripheral wall 403 extending from the superior surface 401 to the inferior surface 402. The peripheral wall 403 may generally comprise the distal end 404, the proximal end 405, the first side 411, and the second side 412 of the intervertebral spacer 400.

The intervertebral spacer 400 may include one or more bone graft channels 460 oriented to pass through opposing ends of the intervertebral spacer 400. For example, the one or more bone graft channels 460 may be formed through the superior and inferior surfaces 401, 402 of the intervertebral spacer 400. The intervertebral spacer 400 may also include one or more side bone graft channels (not shown) that may be formed in the first and second sides 411, 412 of the intervertebral spacer 400. The bone graft channel(s) may be configured to receive bone graft material (not shown) and/or other suitable materials that are known in the art. The intervertebral spacer 400 may also include one or more serrated teeth 480 formed in the superior and inferior surfaces 401, 402 of the intervertebral spacer 400. The one or more serrated teeth 480 may be configured to help stabilize the intervertebral spacer 400 between adjacent vertebral bodies during the fusion process. Moreover, bone graft and/or other suitable materials may also be placed between adjacent serrated teeth 480 of the intervertebral spacer 400 in order to enhance the fusion process and/or help stabilize the intervertebral spacer 400 between adjacent vertebral bodies during the fusion process.

Figure 6A:
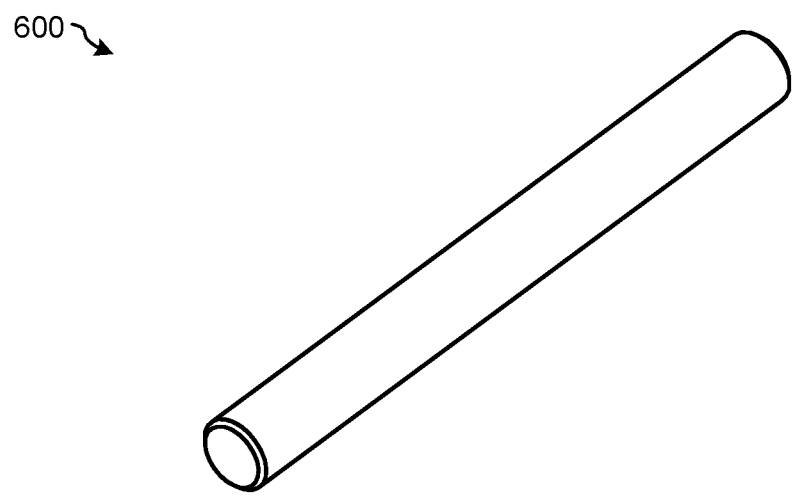
FIG. 6A is a perspective view of a radiopaque marker, according to an embodiment of the present disclosure.
Figure 6B:
FIG. 6B is a side view of the radiopaque marker of FIG. 6A.
Figure 6C:
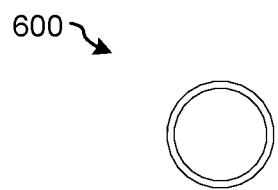
FIG. 6C is an end view of the radiopaque marker of FIG. 6A.
Figure 7A:
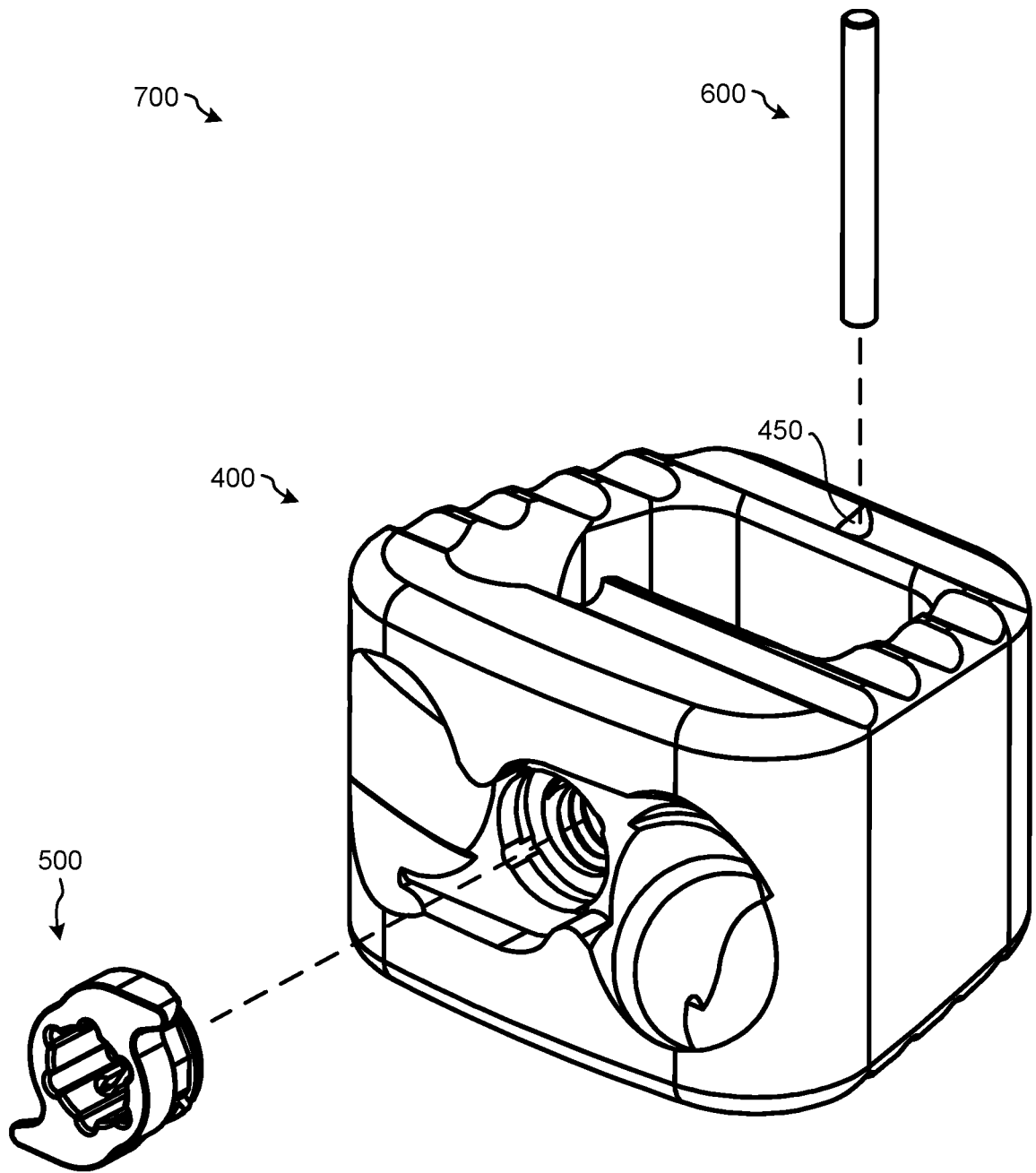
FIG. 7A is an exploded view of an intervertebral spacer assembly including the intervertebral spacer of FIGS. 4A-4H, the locking member of FIGS. 5A-5F, and the radiopaque marker of FIGS. 6A-6C.
Figure 7B:
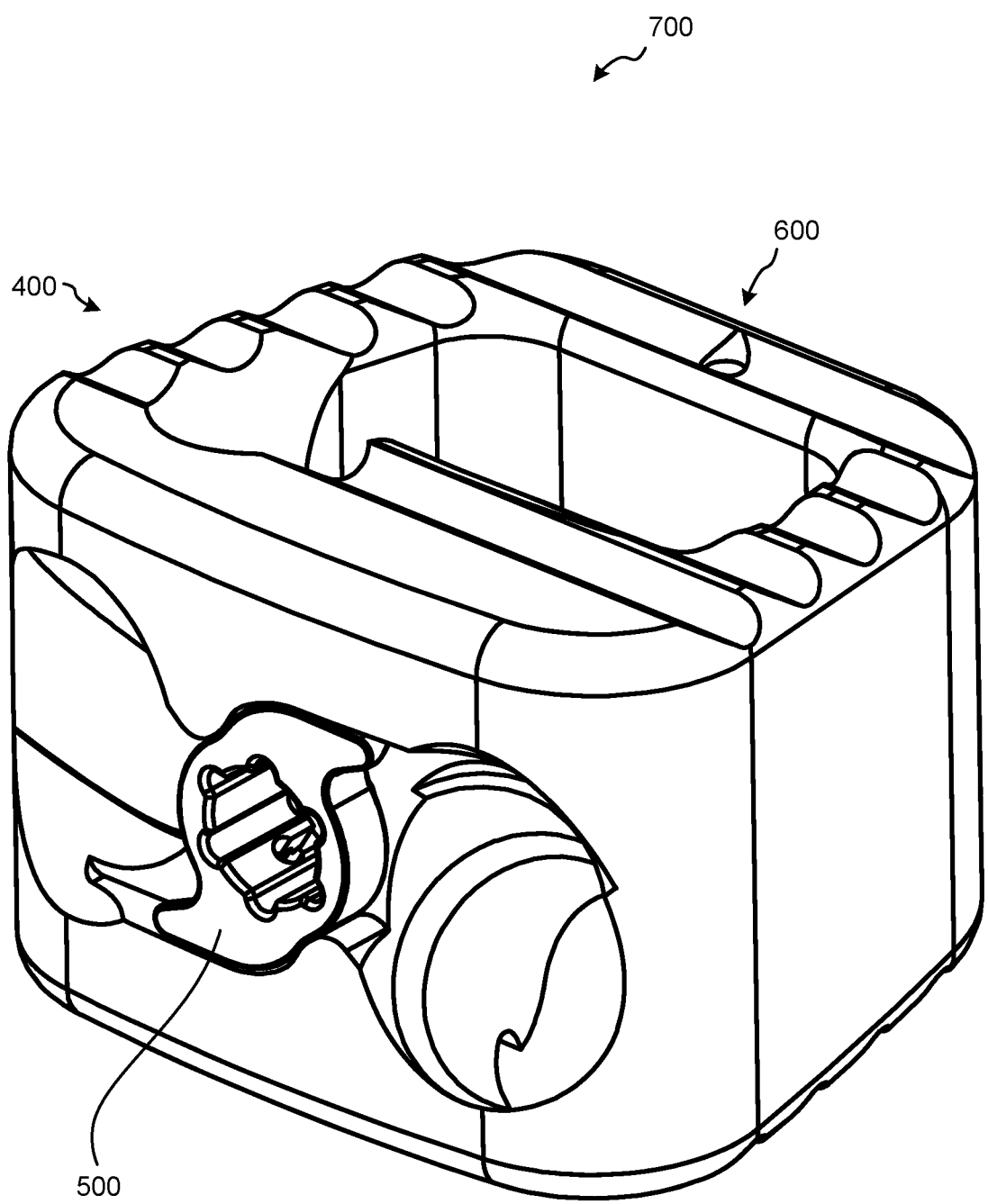
FIG. 7B is a perspective view of the intervertebral spacer assembly of FIG. 7A, after assembly.

The intervertebral spacer 400 may also include one or more marker apertures 450. The one or more marker apertures 450 may be configured to receive one or more radiopaque makers 600, as can be seen in FIGS. 6A-6C. The radiopaque makers 600 may be made from any suitable radiopaque material, such as tantalum (as one non-limiting example). The one or more radiopaque makers 600 may be respectively inserted into the one or more marker apertures 450 in order to couple the one or more radiopaque makers 600 to the intervertebral spacer 400, as can be seen in the exploded view of FIG. 4A, and in the assembled view of FIG. 4B. In this manner, the one or more radiopaque makers 600 may be utilized to verify whether or not the intervertebral spacer 400 has been correctly placed between adjacent vertebral bodies via a suitable x-ray imaging process, which may be performed intraoperatively and/or postoperatively.

Figure 8A:
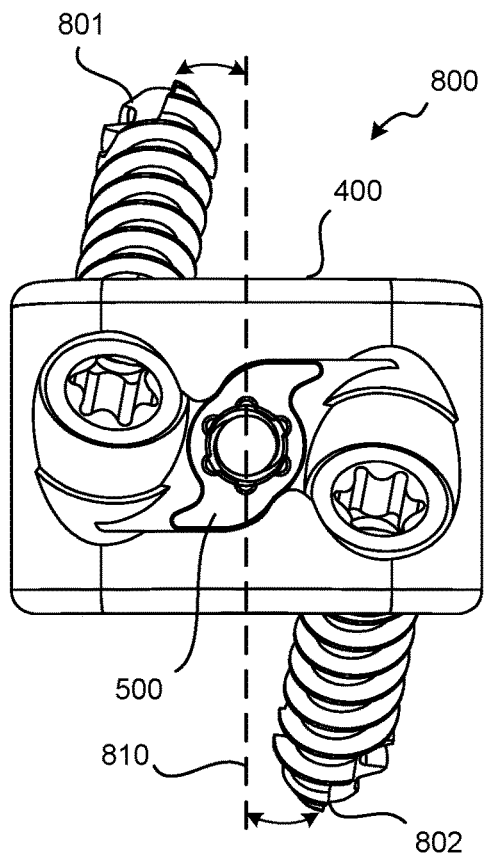
FIG. 8A is a proximal end view of an intervertebral spacer assembly including bone screws and a locking member positioned in an unlocked position, according to an embodiment of the present disclosure.
Figure 8B:
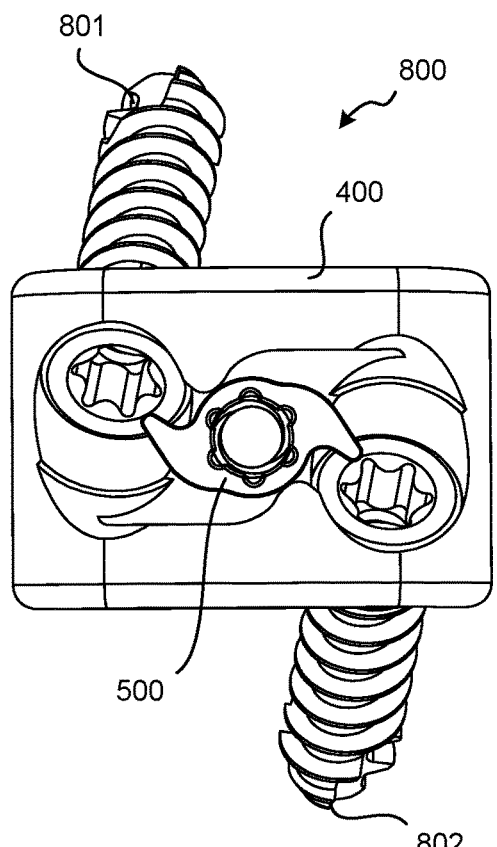
FIG. 8B is a proximal end view of the intervertebral spacer assembly of FIG. 8A with the locking member positioned in a locked position.
Figure 8C:
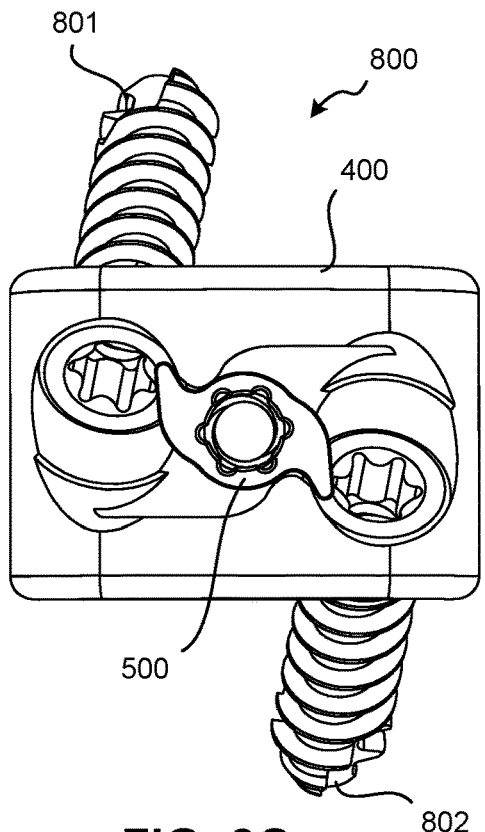
FIG. 8C is a proximal end view of the intervertebral spacer assembly of FIG. 8A with the locking member positioned in an alternative locked position.
Figure 8D:
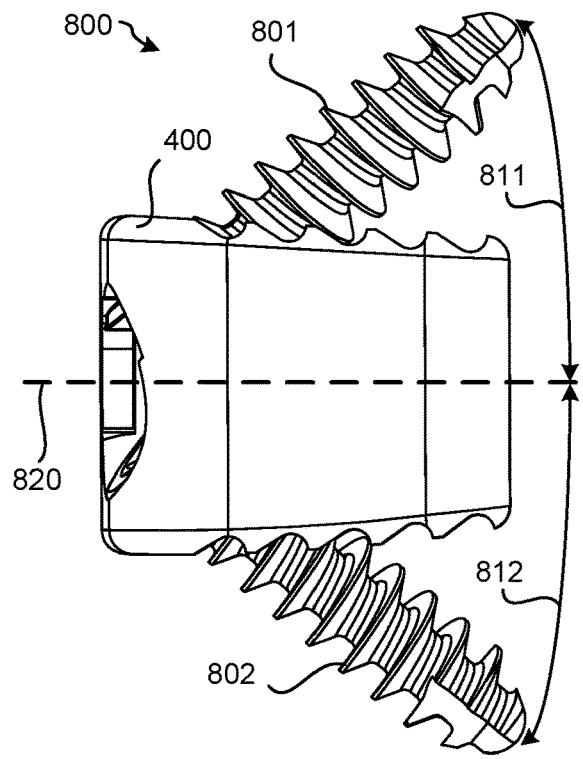
FIG. 8D is a side view of the intervertebral spacer assembly of FIG. 8A.

The proximal end 405 of the intervertebral spacer 400 may include a first fastener channel 431 configured to receive a first fastener or bone screw 801 (e.g., see FIGS. 8A-8D). The first fastener channel 431 may be oriented to pass through the proximal and superior surfaces of the intervertebral spacer 400 at a first angle 811 with respect to a mid-line 820, as shown in FIG. 8D. The proximal end 405 of the intervertebral spacer 400 may also include a second fastener channel 432 configured to receive a second fastener or bone screw 802. The second fastener channel 432 may be oriented to pass through the proximal and inferior surfaces of the intervertebral spacer 400 at a second angle 812 with respect to the mid-line 820, as shown in FIG. 8D.

In some embodiments, the first and second angles 811, 812 may be substantially equal to each other and may be between 10 and 50 degrees. In a particular embodiment, the first and second angles 811, 812 may be about 30 degrees. However, it will be understood that the first and second angles 811, 812 may utilize any angle between 0 degrees and 90 degrees.

Moreover, the first and second fastener channels 431, 432 (and thus bone screws 801, 802) may also be angled inward with respect to a mid-line 810, as shown in FIG. 8A. In at least one embodiment, the bone screws 801, 802 may be angled inward toward the mid-line 810 by about 5 degrees. However, it will be understood that the bone screws 801, 802 may be angled inward toward the mid-line 810, or outward away from the mid-line 810, according to any angle.

The first and second fastener channels 431, 432 may also comprise a first depth stop 433 and a second depth stop 434. The first and second depth stops 433, 434 may prevent an awl tool, a drill tool, and/or the bone screws 801, 802 from penetrating too far within the first and second fastener channels 431, 432, as will be discussed in more detail with respect to FIGS. 17A-20.

The proximal end 405 of the intervertebral spacer 400 may also include a locking member channel 440 intermediate the first and second fastener channels 431, 432. The locking member channel 440 may include an inner wall 445, an annular ridge 446 formed in the inner wall 445, a first pair of recesses 441 formed in the inner wall 445, and a second pair of recesses 442 formed in the inner wall 445. The second pair of recesses 442 may be angularly offset from the first pair of recesses 441 about a longitudinal axis 443 of the locking member channel 440 (see FIGS. 4A and 4H). In some embodiments, the second pair of recesses 442 may be angularly offset from the first pair of recesses 441 by about 30 degrees. In some embodiments, the second pair of recesses 442 may be angularly offset from the first pair of recesses 441 by about 90 degrees. In some embodiments, the second pair of recesses 442 may be angularly offset from the first pair of recesses 441 at any angle between 10 and 170 degrees. However, it will be understood that the second pair of recesses 442 may be angularly offset from the first pair of recesses 441 at any angle between 0 and 360 degrees. The locking member channel 440 may also include first threading 444 configured to engage second threading formed on an inserter tool (e.g., see FIGS. 2A-2E).

The proximal end 405 of the intervertebral spacer 400 may also include a first pair of stop surfaces 447 configured to prevent a locking member 500 from rotating in a first direction (e.g., counter clockwise) past an unlocked position (see FIG. 8A), and a second pair of stop surfaces 448 configured to prevent the locking member from rotating in a second direction (e.g., clockwise) past a locked position (see FIG. 8C).

Figure 5A:
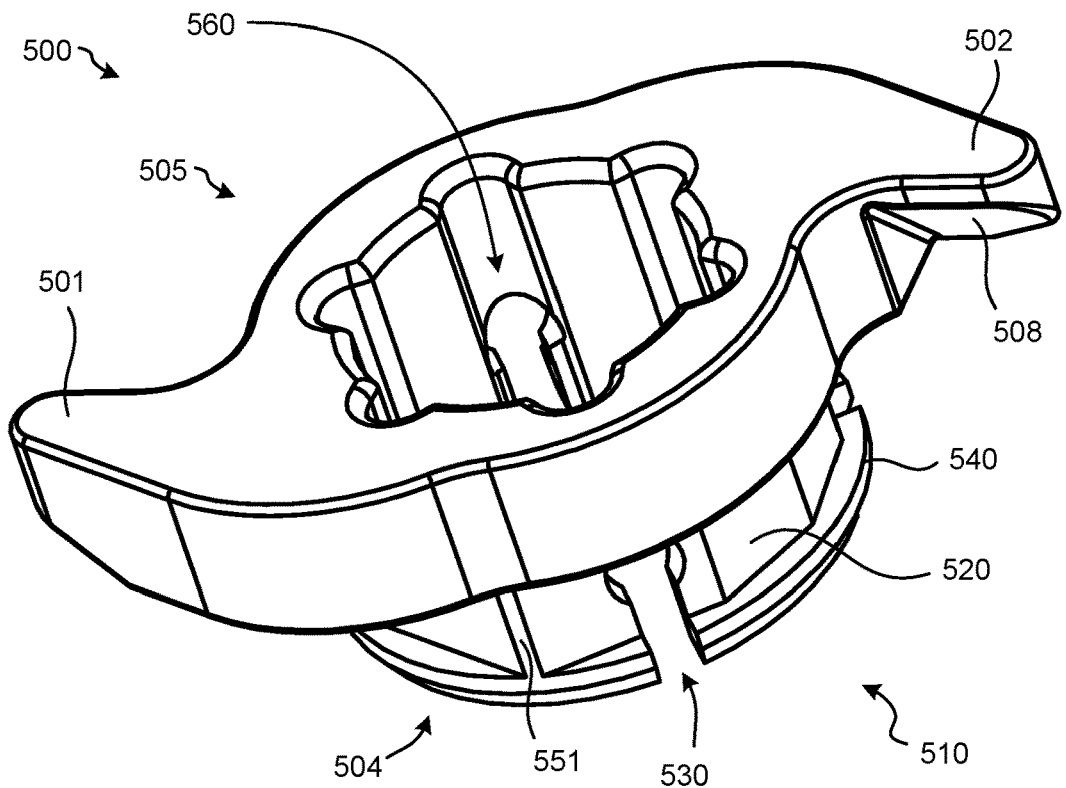
FIG. 5A is a perspective top view of a locking member, according to an embodiment of the present disclosure.
Figure 5B:
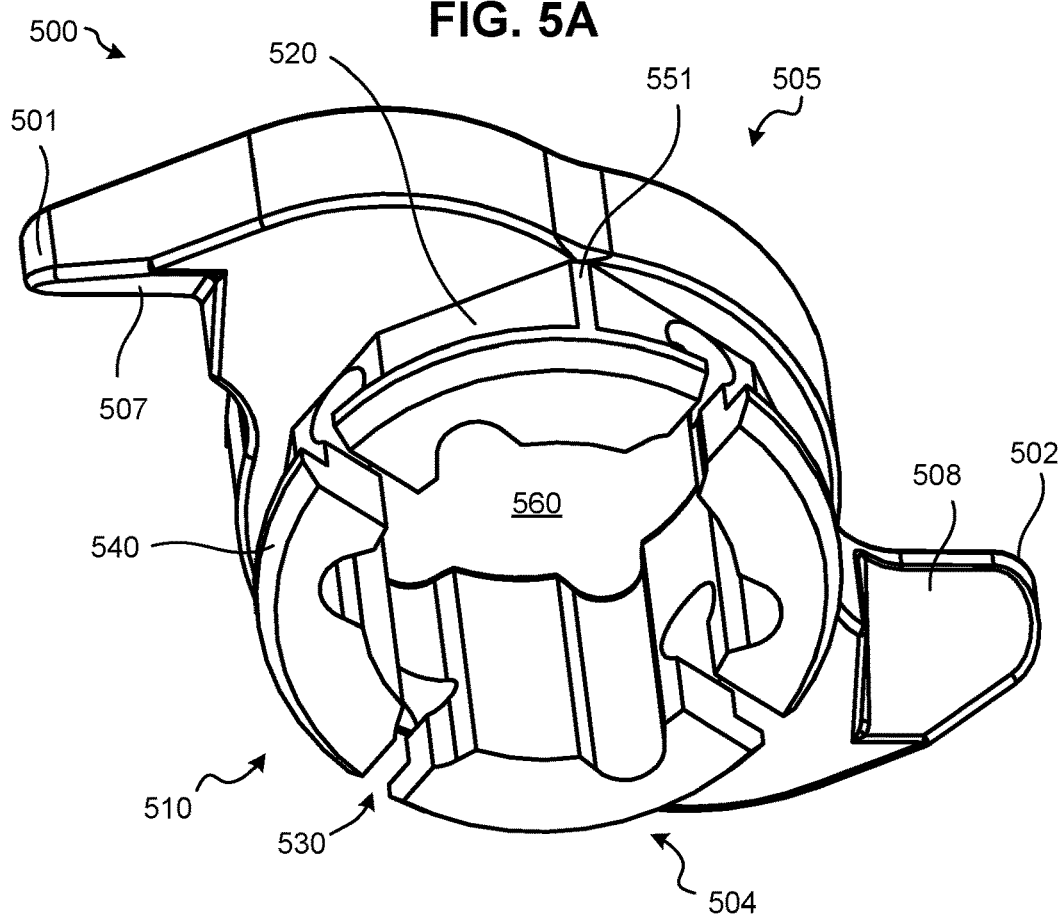
FIG. 5B is a perspective bottom view of the locking member of FIG. 5A.
Figure 5C:
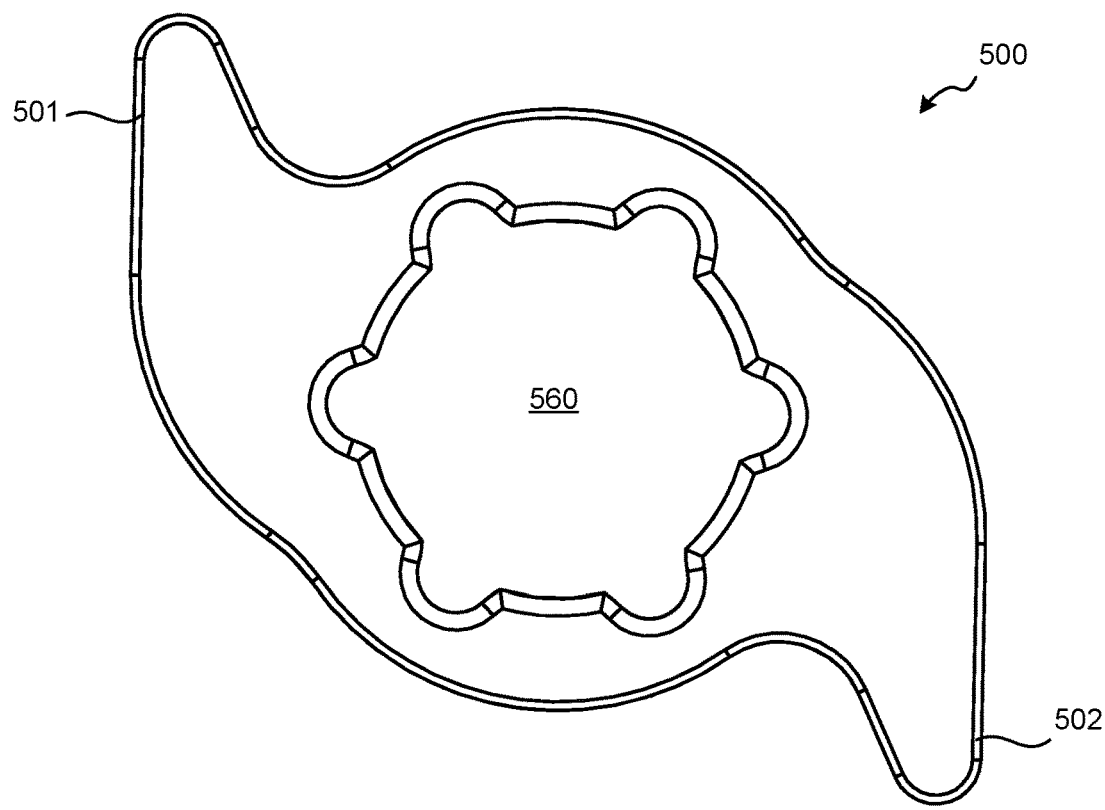
FIG. 5C is a top view of the locking member of FIG. 5A.
Figure 5D:
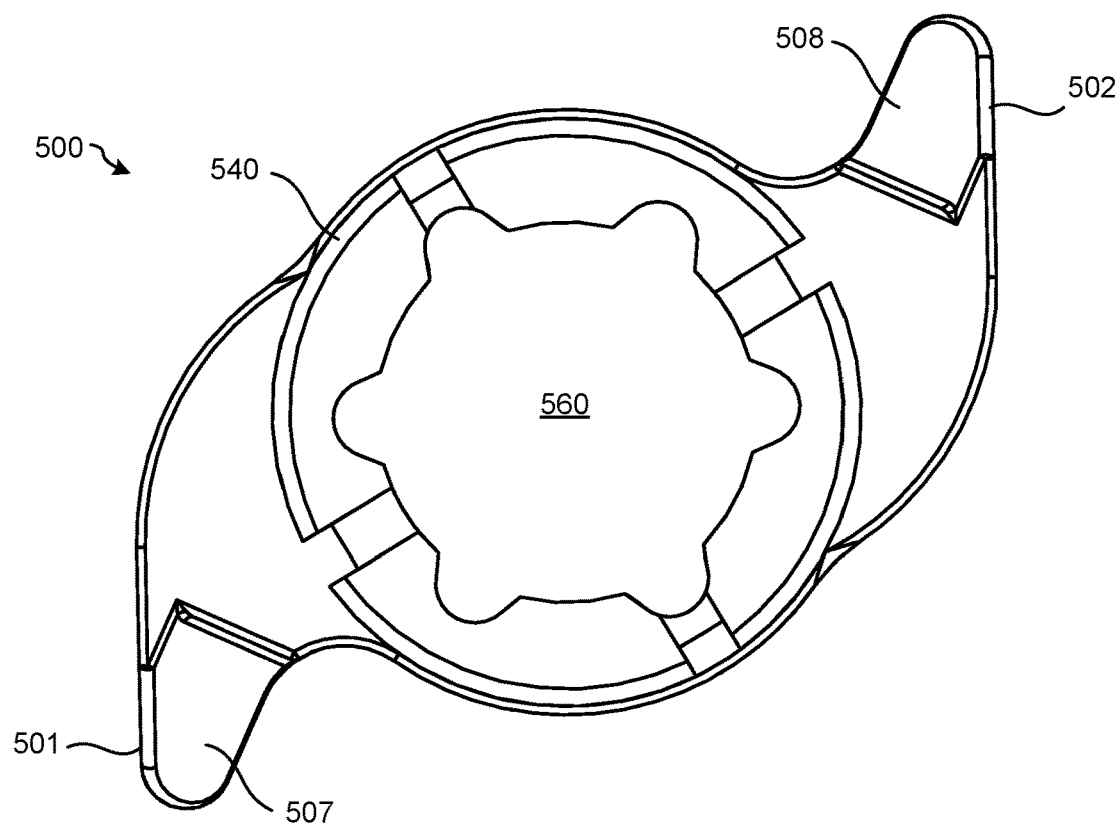
FIG. 5D is a bottom view of the locking member of FIG. 5A.
Figure 5E:
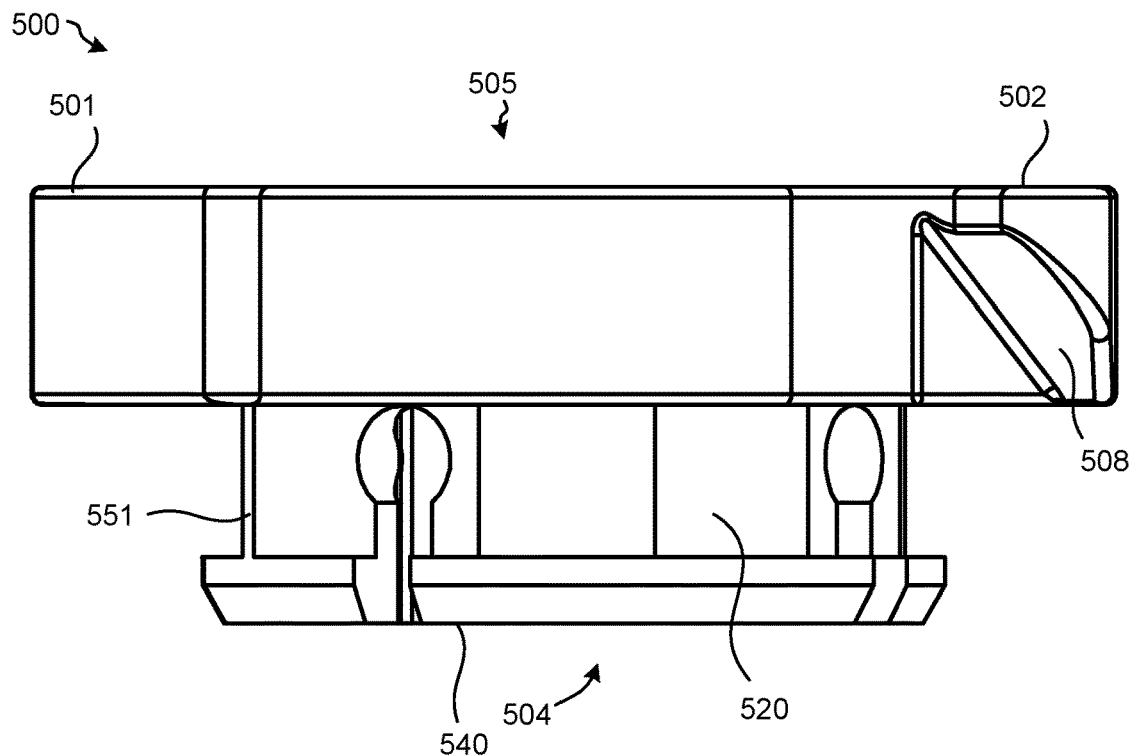
FIG. 5E illustrates a first side of the locking member of FIG. 5A.
Figure 5F:
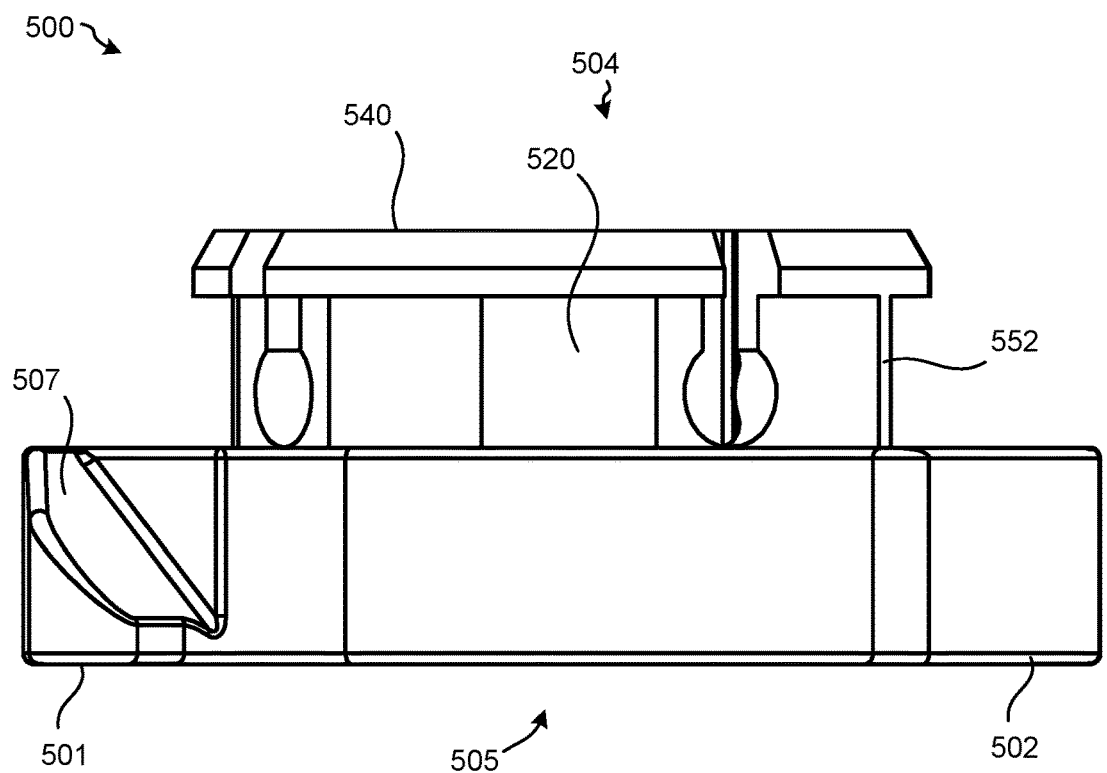
FIG. 5F illustrates a second side of the locking member of FIG. 5A.

FIGS. 5A-5F illustrate various views of a locking member 500, according to an embodiment of the present disclosure. Specifically, FIG. 5A is a perspective top view of the locking member 500; FIG. 5B is a perspective bottom view of the locking member 500; FIG. 5C is a top view of the locking member 500; FIG. 5D is a bottom view of the locking member 500; FIG. 5E illustrates a first side of the locking member 500; and FIG. 5F illustrates a second side of the locking member 500 of FIG. 5A.

The locking member 500 may generally include a proximal end 505 with a first anti-backout member 501 and a second anti-backout member 502, a distal end 504 including a collet 510, and a driver engagement channel 560 extending through the proximal and distal ends 505, 504 of the locking member 500.

The first and second anti-backout members 501, 502 may protrude radially away from the locking member 500. The first and second anti-backout members 501, 502 may also include angled engagement surfaces 507, 508 configured to engage the second pair of stop surfaces 448 formed in the intervertebral spacer 400. The second pair of stop surfaces 448 may also include complementarily shaped angled surfaces configured to receive the angled engagement surfaces 507, 508 of the first and second anti-backout members 501, 502.

The collet 510 may include a peripheral wall 520 with one or more slits 530 formed therein. In the example shown in FIGS. 5A-5F, the peripheral wall 520 of the collet 510 includes four slits 530 which are regularly spaced apart from each other. However, it will be understood that any number of slits 530 spaced apart from each other at any distance, arrangement, or pattern may also be utilized. The collet 510 may also include an annular flange 540 at its distal end which may be configured to be retained by the annular ridge 446 of the locking member channel 440 in order to rotatably couple the locking member 500 to the intervertebral spacer 400. For example, as the collet 510 of the locking member 500 is inserted into the locking member channel 440 of the intervertebral spacer 400 (e.g., see FIG. 4A), the slits 530 of the collet 510 will permit the collet 510 to compress inwardly to allow the annular flange 540 of the collet 510 to pass distally, beyond the annular ridge 446 that is formed in the inner wall 445 of the locking member channel 440. Once the annular flange 540 of the collet 510 has moved distal to the annular ridge 446, the collet 510 will expand outwardly again and the annular ridge 446 will retain the annular flange 540 of the collet 510 in order to rotatably couple the locking member 500 to the intervertebral spacer 400.

However, other embodiments for rotatably coupling the locking member 500 to the intervertebral spacer 400 are also contemplated herein. For example, in one embodiment contemplated herein (not shown), the locking member channel 440 may include an integral collet member configured to couple a shaft protruding from a locking member. The shaft protruding from the locking member may further include a ridge that may interact with the integral collet member within the intervertebral spacer in order to rotatably couple the locking member to the intervertebral spacer. In another example embodiment contemplated herein (not shown), a shaft protruding from a locking member may be rotatably coupled to an intervertebral spacer via a fastening member that can couple the locking member to the intervertebral spacer while allowing for rotation of the locking member (e.g., a rivet, a nut, a bolt, a screw, etc.).

Returning to FIGS. 5A-5F, the peripheral wall 520 of the collet 510 may include a first stop protrusion 551 projecting from a first side of the peripheral wall 520, and a second stop protrusion 552 projecting from a second side of the peripheral wall 520, opposite the first stop protrusion 551. Once the locking member 500 is rotatably coupled to the intervertebral spacer 400, as discussed above, the locking member 500 can be rotated within the locking member channel 440 between at least two stable positions comprising an unlocked position and a locked position. In the unlocked position, the first and second stop protrusions 551, 552 may protrude into the first pair of recesses 441 in order to retain the locking member 500 in the unlocked position, such that the first and second anti-backout members 501, 502 do not obstruct the first and second fastener channels 431, 432 (e.g., see FIG. 8A). In the locked position, the first and second stop protrusions 551, 552 may protrude into the second pair of recesses 442 in order to retain the locking member 500 in the locked position, such that the first and second anti-backout members 501, 502 obstruct the first and second fastener channels 431, 432 and prevent the first and second fasteners or bone screws 801, 802 from backing out of the first and second fastener channels 431, 432 (e.g., see FIGS. 8B and 8C for two example locked positions).

However, it will also be understood that other embodiments are contemplated herein in order to position and maintain the locking member 500 in either the unlocked or locked positions. For example, the inner wall 445 of the locking member channel 440 may comprise one or more inner wall engagement features that may engage with one or more collet engagement features formed on the collet 510 in order to retain the locking member 500 in either the unlocked or locked position, independently of any additional component besides the locking member 500 and the intervertebral spacer 400, such that one or more anti-backout members 501, 501 may selectively obstruct one or more fastener channels. In this example, the one or more inner wall engagement features may comprise one or more recesses or one or more protrusions. Likewise, the one or more collet engagement features may comprise one or more recesses or one or more protrusions that are complementarily shaped to the one or more inner wall engagement features. In this manner, in the unlocked position, the one or more collet engagement features may engage with the one or more inner wall engagement features in order to retain the locking member 500 in the unlocked position, independently of any additional component besides the locking member 500 and the intervertebral spacer 400, and the one or more anti-backout members 501, 502 may not obstruct the one or more fastener channels 431, 432. Likewise, in the locked position, the one or more collet engagement features may engage with the one or more inner wall engagement features to retain the locking member 500 in the locked position, independently of any additional component besides the locking member 500 and the intervertebral spacer 400, and the one or more anti-backout members 501, 502 may obstruct the one or more fastener channels in order to prevent one or more fasteners or bone screws 801, 802 from backing out of the one or more fastener channels.

FIGS. 9A-21 illustrate various views of surgical instruments, tools, and assemblies that may be utilized to implant an intervertebral spacer 400 of the present disclosure.

Figure 9A:
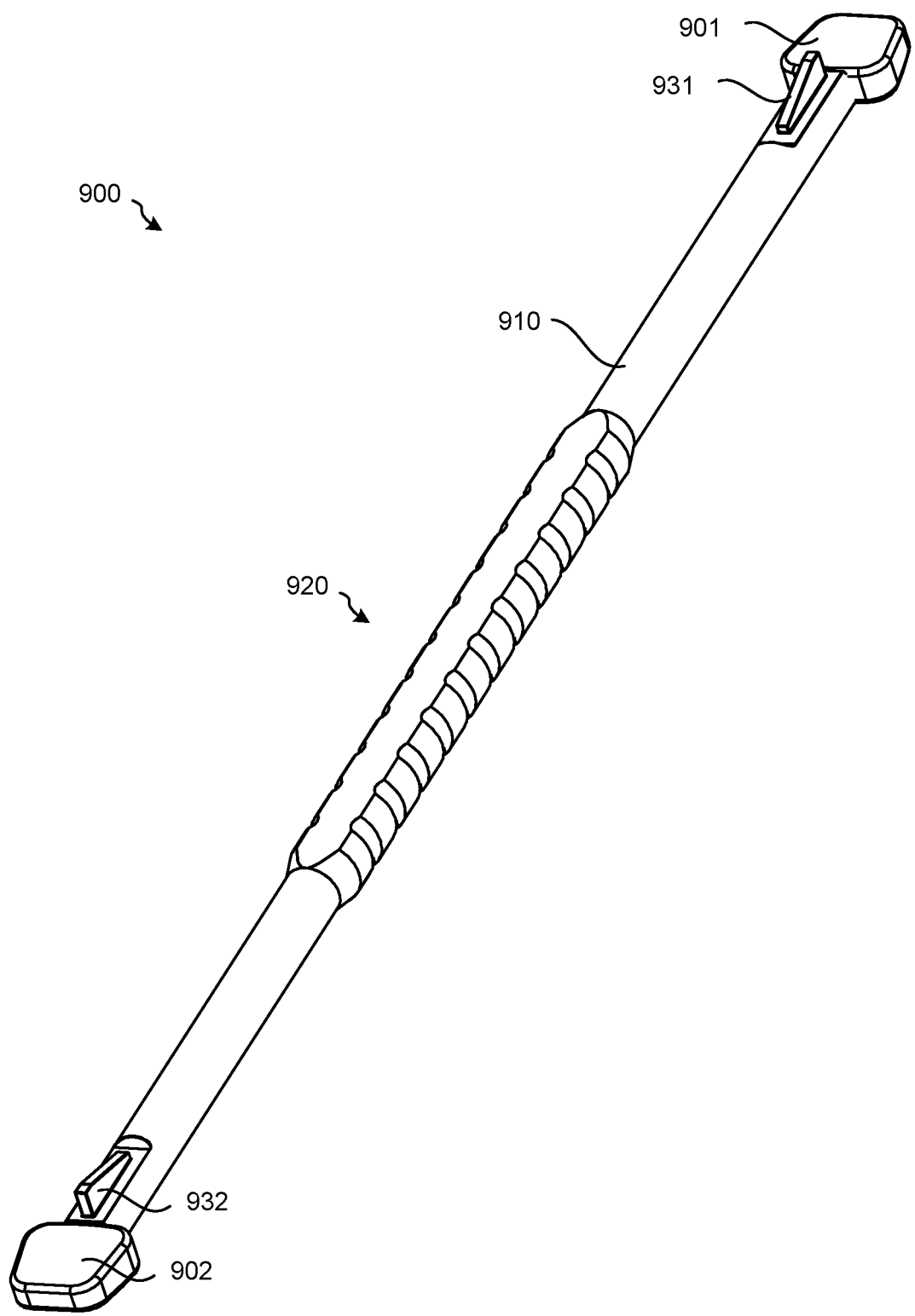
FIG. 9A is a perspective top view of a trial tool, according to an embodiment of the present disclosure.
Figure 9B:
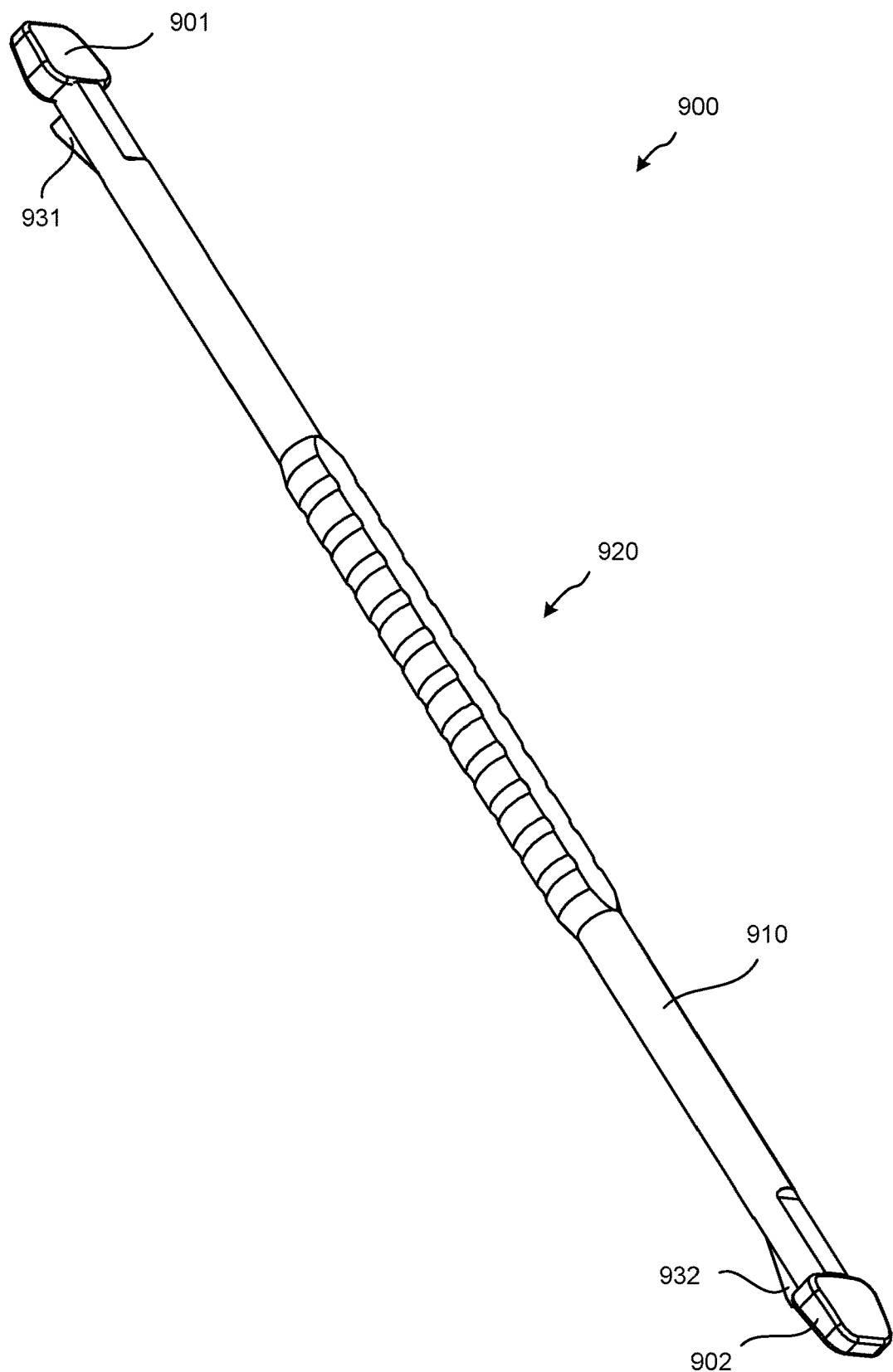
FIG. 9B is a perspective bottom view of the trial tool of FIG. 9A.

FIGS. 9A and 9B are perspective top and bottom views of an example trial tool 900 which may be utilized during a surgical procedure to implant an intervertebral spacer 400. For example, once a surgeon has created a space between two vertebral bodies for the intervertebral spacer 400 (e.g., by removing at least a portion of an intervertebral disc), the surgeon may utilize the trial tool 900 (or another trial tool from a set of trial tools having different sizes) in order to ascertain which size of intervertebral spacer 400 should be implanted in the disc space between the two vertebral bodies.

As shown in FIGS. 9A and 9B, the trial tool 900 may generally comprise a shaft 910, a handle portion 920, a first trial component 901 having a first size, a first depth stop 931 adjacent the first trial component 901, a second trial component 902 having a second size, and a second depth stop 932 adjacent the second trial component 902. The first and second depth stops 931, 932 may contact at least one of the vertebral bodies in order to prevent the first and second trial components 901, 902 from being inserted too far into the prepared disc space.

FIGS. 10A and 10B illustrate how the inserter tool 200 and the intervertebral spacer 400 may be coupled together to form an insertion assembly 1000. Specifically, the distal end 204 of the inserter tool 200 comprising the second threading 230 may be moved distally (e.g., in the direction of arrow 1001), such that the distal end 204 of the inserter tool 200 may pass through the driver engagement channel 560 formed through the locking member 500. The second threading 230 may then be engaged with the first threading 444 within the locking member channel 440 of the intervertebral spacer 400 in order to couple the intervertebral spacer 400 to the inserter tool 200. In at least one embodiment, the insertion assembly 1000 comprises the intervertebral spacer 400 preassembled onto the inserter tool 200, which may be packaged within a sterile container.

Figure 11A:
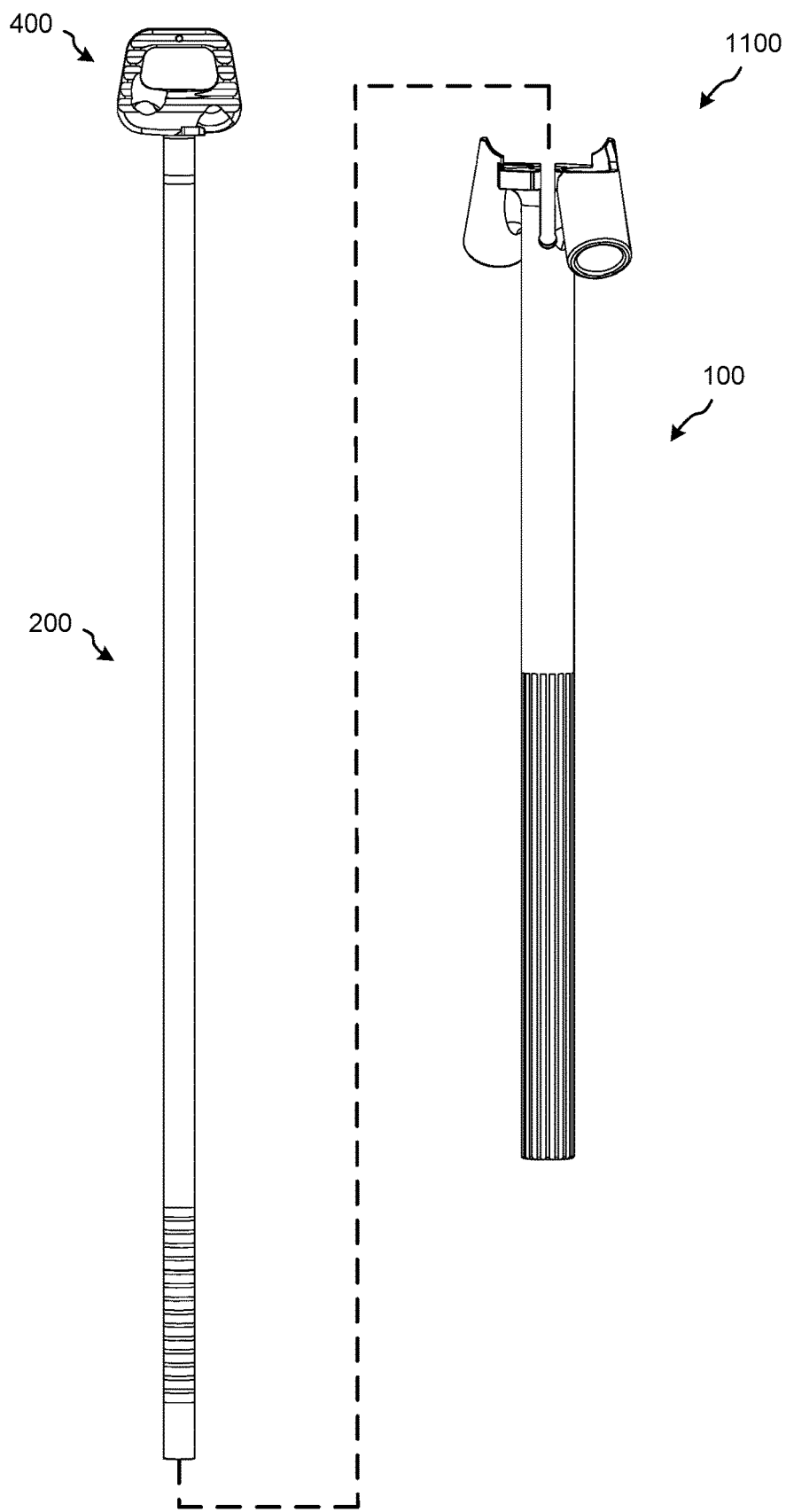
FIG. 11A is an exploded view of an insertion assembly including the inserter tool, the intervertebral spacer, and the DTS guide, prior to assembly.
Figure 11B:
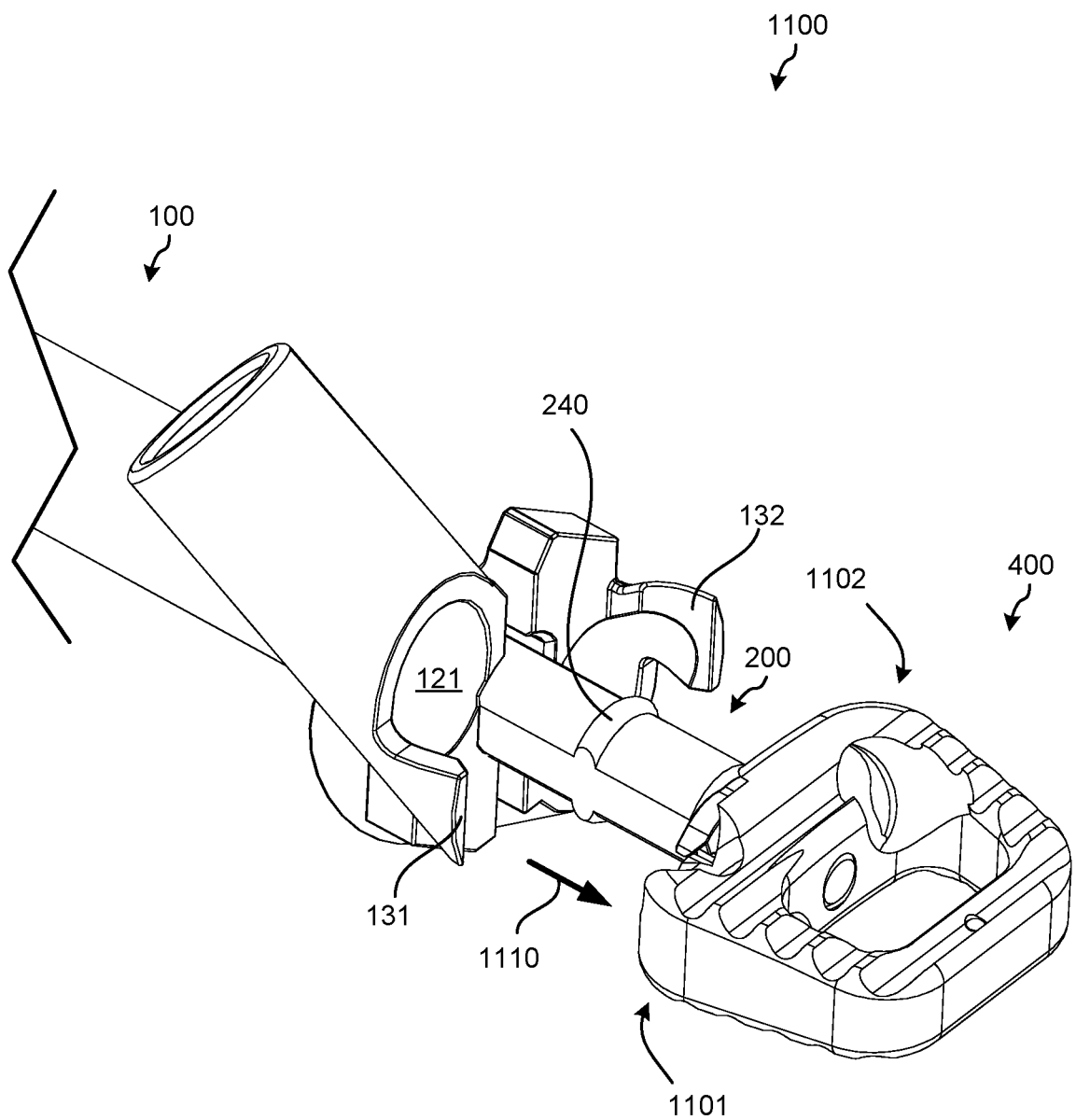
FIG. 11B is a close up view of the distal end of the insertion assembly illustrating the DTS guide engaging with the intervertebral spacer.
Figure 11C:
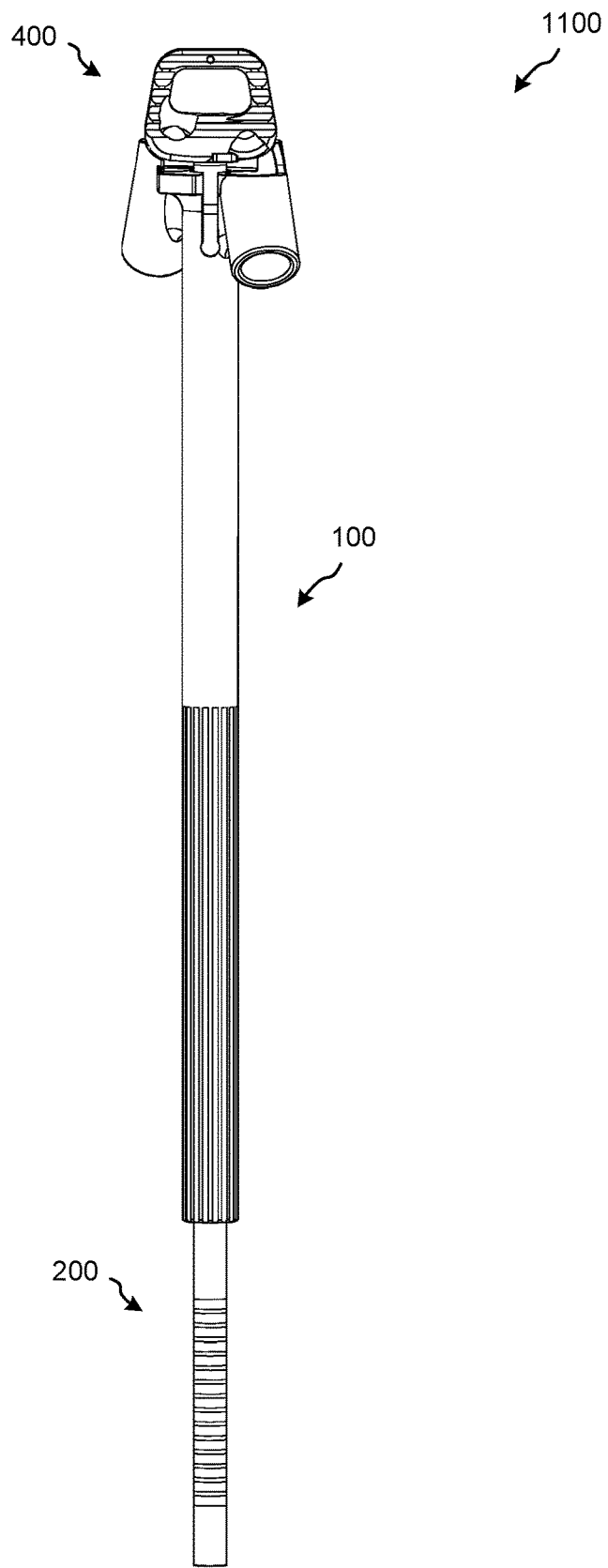
FIG. 11C is a top view of the insertion assembly of FIG. 11A after assembly.

FIGS. 11A-11C illustrate how the DTS guide 100 may be coupled with the inserter tool 200 and the intervertebral spacer 400 to form an insertion assembly 1100. Specifically, FIG. 11A is an exploded view of the insertion assembly 1100 prior to assembly; FIG. 11B is a close up view of the distal end of the insertion assembly 1100 as the DTS guide 100 is moved distally to engage the intervertebral spacer 400; and FIG. 11C is a top view of the insertion assembly 1100 after assembly.

In general, the DTS guide shaft lumen 160 is configured to receive the shaft 210 of the inserter tool 200 to slidably couple the DTS guide 100 with the inserter tool 200. The ridges 240 formed on the inserter tool 200 may couple with recesses (not shown) formed within the DTS guide shaft lumen 160 in order to removably couple the DTS guide 100 to the inserter tool 200. As the DTS guide 100 moves distally (e.g., see Arrow 1110 in FIG. 11B) to couple with the inserter tool 200, the first and second DTS guide wings 131, 132 of the DTS guide 100 will engage the intervertebral spacer 400 and impart forces on the intervertebral spacer 400 that will act to correctly orient the DTS guide 100 with respect to the intervertebral spacer 400. In this manner, the first and second DTS guide channels 121, 122 of the DTS guide 100 will assume correct alignment with the first and second fastener channels 431, 432 of the intervertebral spacer 400. More specifically, the first DTS guide wing 131 may be configured to abut against a first surface 1101 of the intervertebral spacer 400, and the second DTS guide wing 132 may be configured to abut against a second surface 1102 of the intervertebral spacer in order to align the first and second DTS guide channels 121, 122 of the DTS guide 100 with the first and second fastener channels 431, 432 of the intervertebral spacer 400. Thus, the first DTS guide channel 121 will be correctly aligned and configured to receive the first fastener or bone screw 801 at the first angle 811 in order to guide the first fastener or bone screw 801 into the first fastener channel 431 of the intervertebral spacer 400, and the second DTS guide channel 122 will be configured to receive the second fastener or bone screw 802 at the second angle 812 in order to guide the second fastener or bone screw 802 into the second fastener channel 432 of the intervertebral spacer 400.

It will be noted that the first and second DTS guide wings 131, 132 are configured to align the first and second DTS guide channels 121, 122 with respect to the first and second fastener channels 431, 432, independently of any additional apertures or recesses formed in the intervertebral spacer 400. It will also be noted that intervertebral spacers of different sizes may be paired with DTS guides that have a corresponding size. Moreover, in at least one embodiment, the insertion assembly 1100 may comprise the intervertebral spacer 400 and the DTS guide 100 preassembled onto the inserter tool 200, which may then be packaged within a sterile container.

Figure 12A:
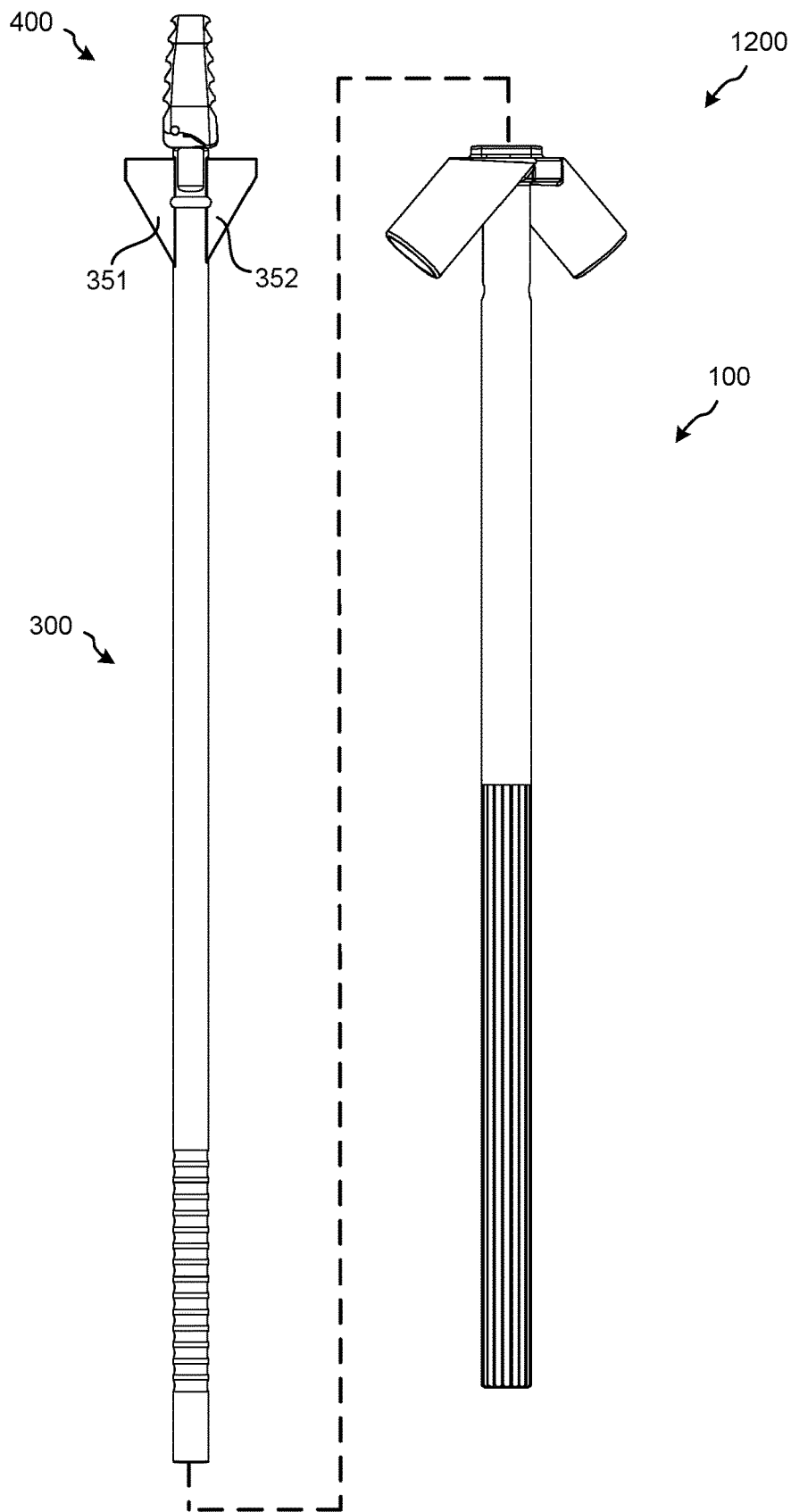
FIG. 12A is an exploded view of an insertion assembly including the inserter tool, the intervertebral spacer, and the DTS guide, prior to assembly.
Figure 12B:
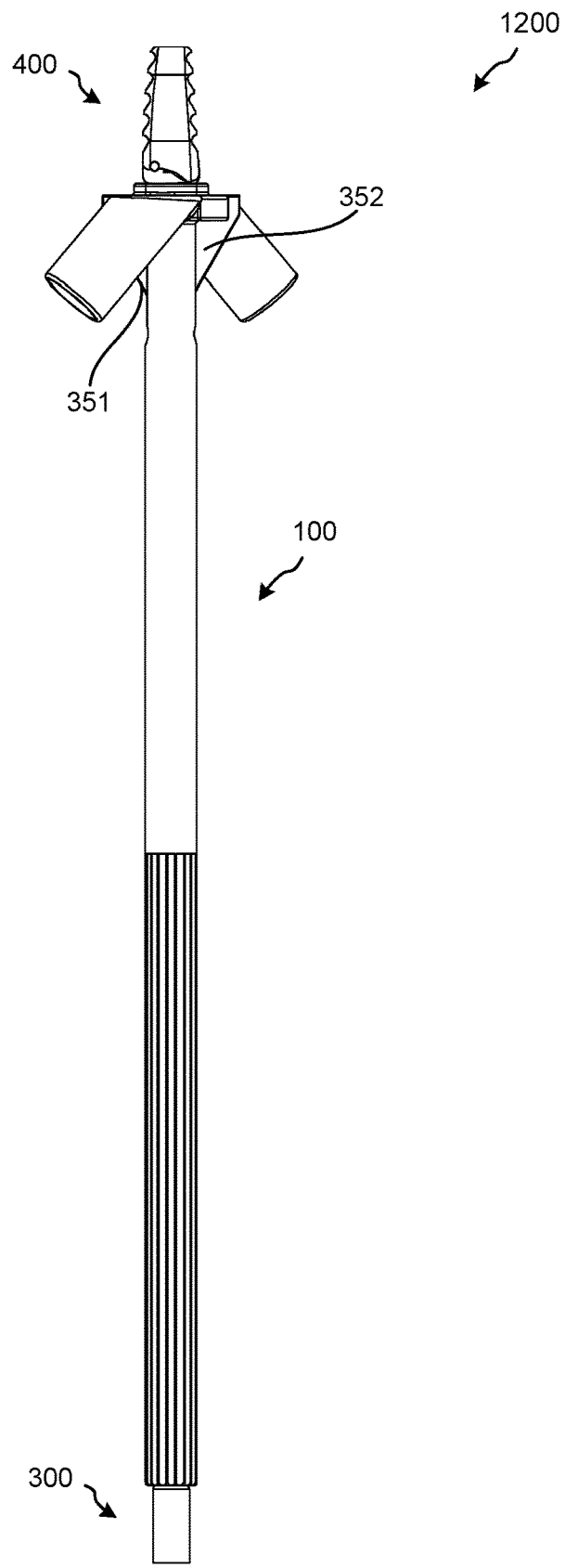
FIG. 12B is a side view of the insertion assembly of FIG. 12A after assembly.

FIGS. 12A and 12B illustrate how the DTS guide 100 may be coupled with the intervertebral spacer 400 and the inserter tool 300 shown in FIGS. 3A-3E in order to form an insertion assembly 1200. Specifically, FIG. 12A is an exploded view of the insertion assembly 1200 prior to assembly and FIG. 12B is a side view of the insertion assembly 1200 after assembly. The assembly operation for the insertion assembly 1200 may be similar to the assembly operation for the insertion assembly 1100 shown in FIGS. 11A-11C. However, the first and second guide fins 351, 352 on the inserter tool 300 may be received within the DTS guide fin slot 150 formed in the DTS guide 100 in order to align the first and second DTS guide channels 121, 122 of the DTS guide 100 with the first and second fastener channels 431, 432 of the intervertebral spacer 400.

Figure 13A:
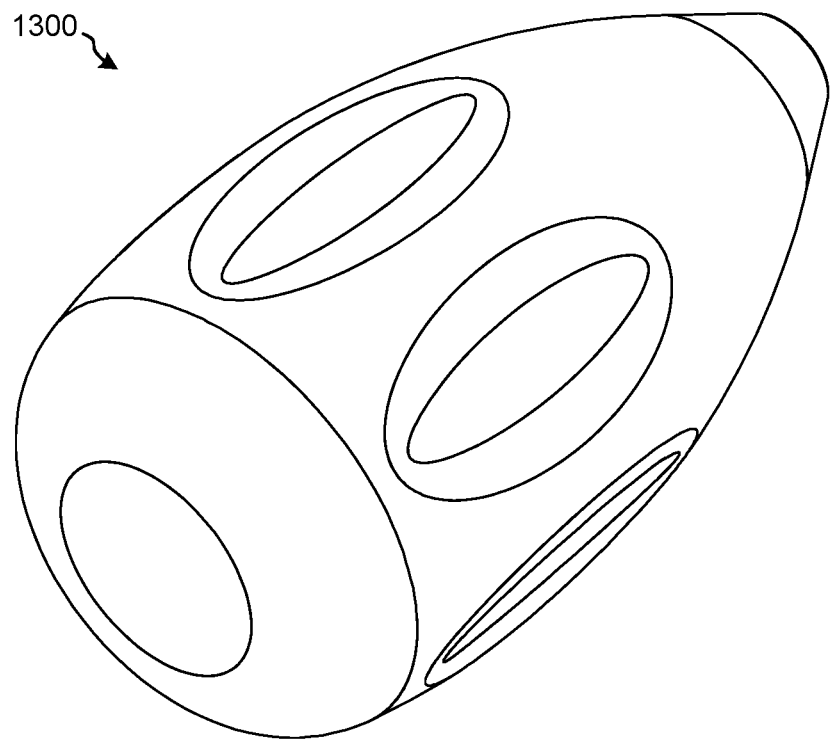
FIG. 13A is a perspective top view of a handle, according to an embodiment of the present disclosure.
Figure 13B:
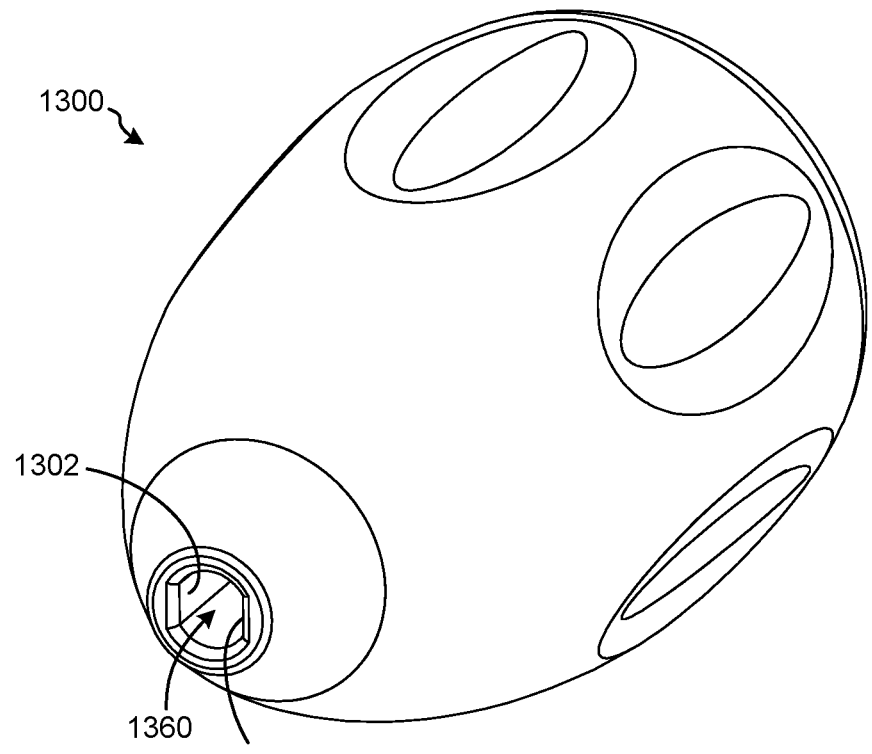
FIG. 13B is a perspective bottom view of the handle of FIG. 13A.

FIGS. 13A and 13B illustrate perspective top and bottom views of a handle 1300 that may be utilized with the insertion assemblies 1100, 1200 of FIGS. 11A-12B. In at least one embodiment, the handle 1300 may have a "double D" shaped lumen 1360 with a first handle engagement surface 1301 and a second handle engagement surface 1302 configured to receive the "double D" shaped shaft 210 of the inserter tool 200, as previously discussed.

Figure 14A:
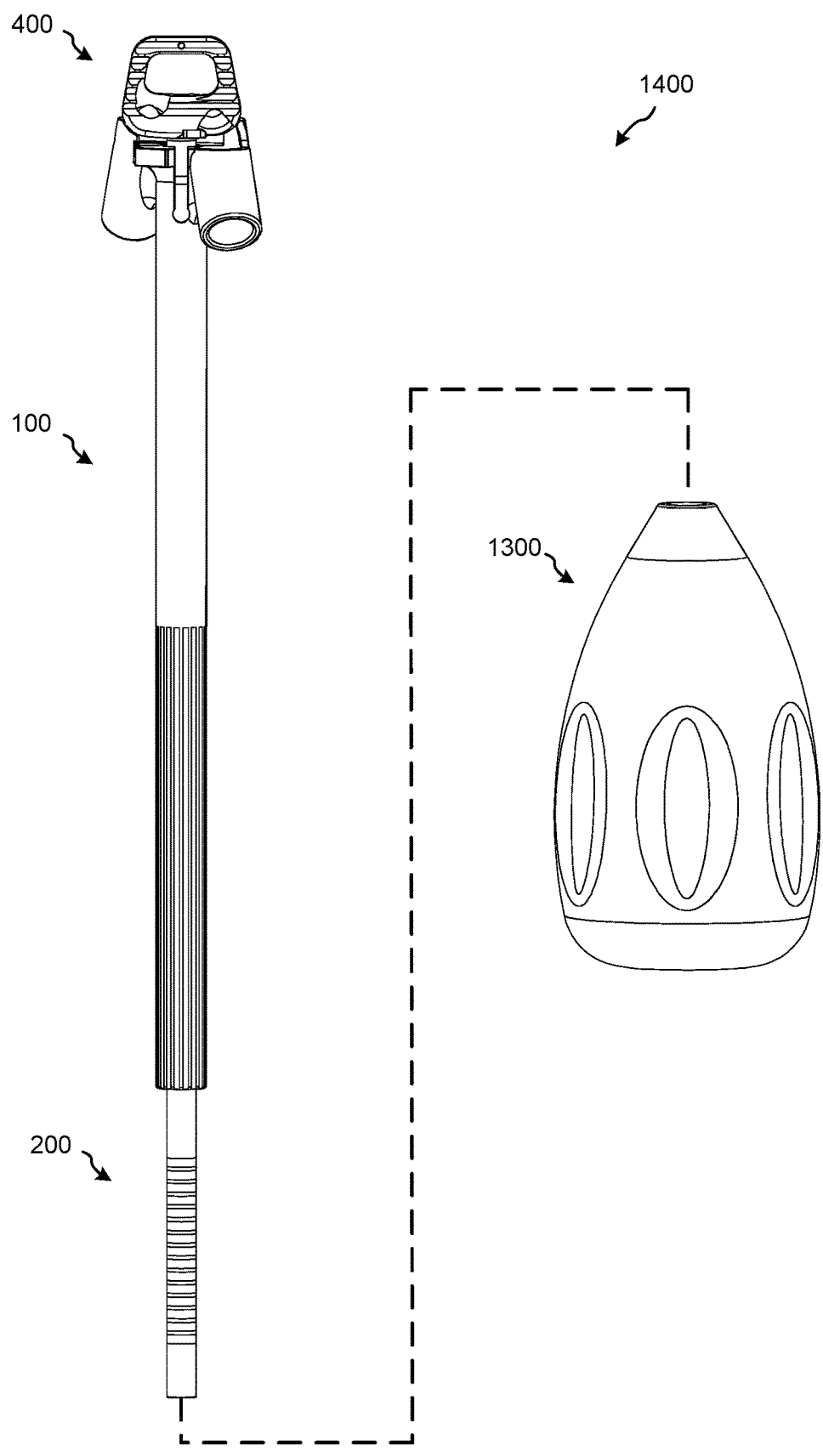
FIG. 14A is an exploded view of an insertion assembly including the inserter tool, the intervertebral spacer, the DTS guide, and the handle, prior to assembly.
Figure 14B:
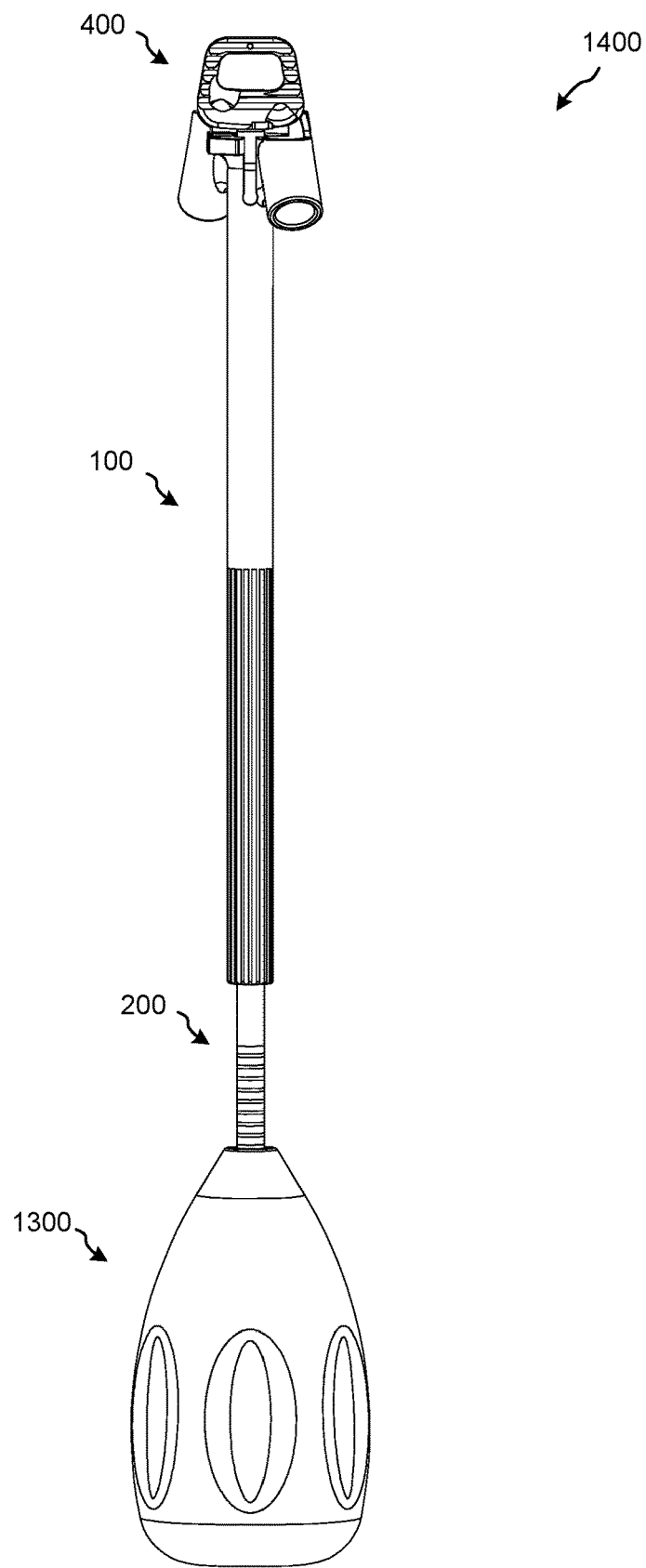
FIG. 14B is a top view of the insertion assembly of FIG. 14A after assembly.

FIGS. 14A and 14B illustrate how the handle 1300 may be coupled with the inserter tool 200, which itself may be coupled with the intervertebral spacer 400 and the DTS guide 100, in order to form an insertion assembly 1400. The surgeon may then utilize the insertion assembly 1400 to insert the intervertebral spacer 400 between two vertebral bodies of a patient by using the handle to manipulate the intervertebral spacer 400 into place. The surgeon may also utilize an impact tool (not shown) to strike the proximal end of the handle 1300 and drive the intervertebral spacer 400 into place. The first and second depth stop surfaces 141, 142 of the DTS guide may help prevent the surgeon from inserting the intervertebral spacer 400 too far into the disc space between the two vertebral bodies. Once the intervertebral spacer 400 has been properly placed between the two vertebral bodies, the surgeon may remove the handle 1300 from the insertion assembly 1400.

Figure 15A:
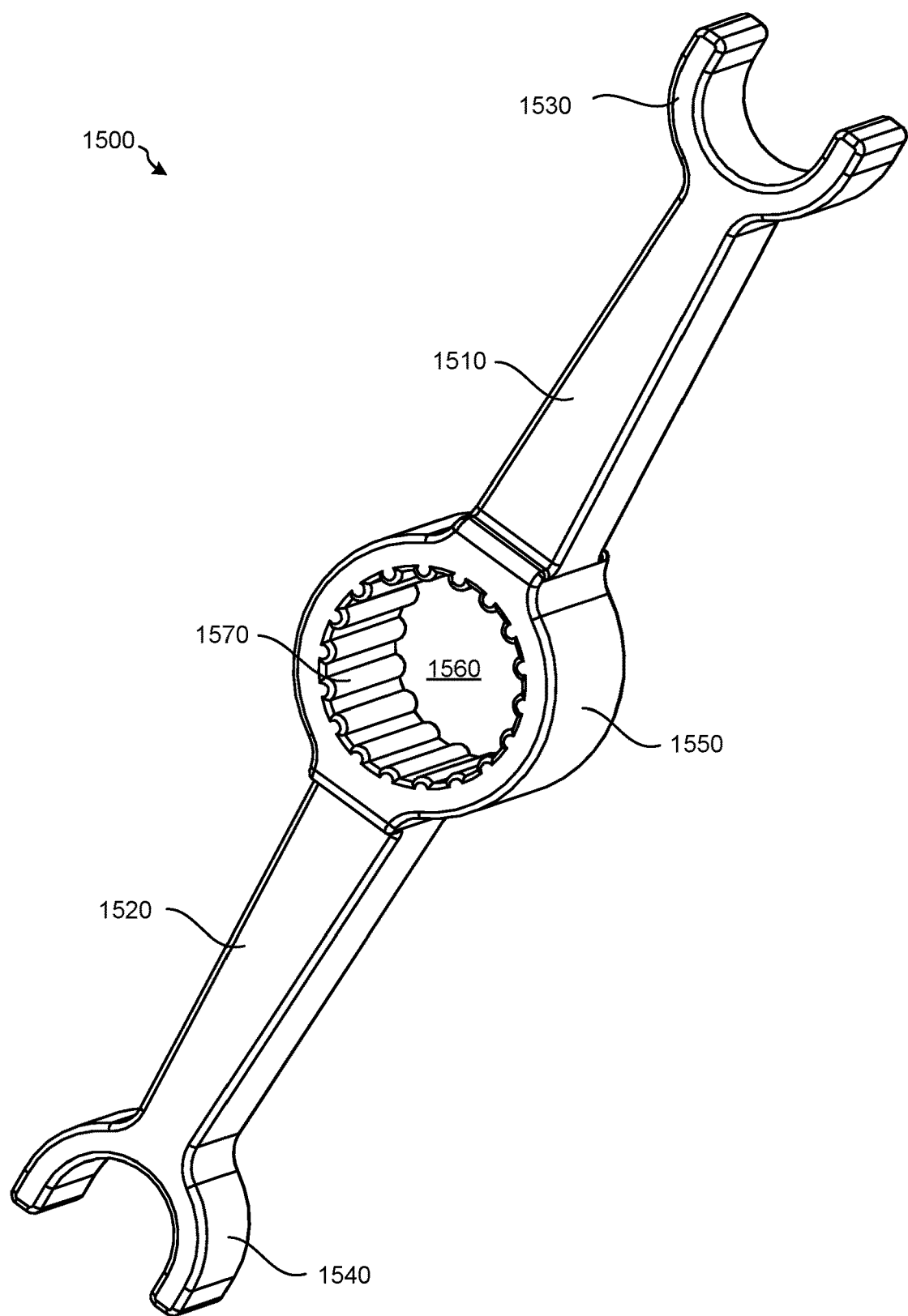
FIG. 15A is a perspective view of a U-support tool, according to an embodiment of the present disclosure.

FIGS. 15A-15D illustrate various views of a U-support tool 1500 that may be utilized with the insertion assembly 1100 of FIG. 11B. Specifically, FIG. 15A is a perspective view of the U-support tool 1500; FIG. 15B is a front side view of the U-support tool 1500; FIG. 15C is a top view of the U-support tool 1500; and FIG. 15D is a left side view of the U-support tool 1500. The U-support tool 1500 may generally include a first arm 1510 having a first U-support 1530, a second arm 1520 having a second U-support 1540, and a ring member 1550 intermediate the first and second arms 1510, 1520 including a ring channel 1560 with one or more ring splines 1570 formed therein.

Figure 16A:
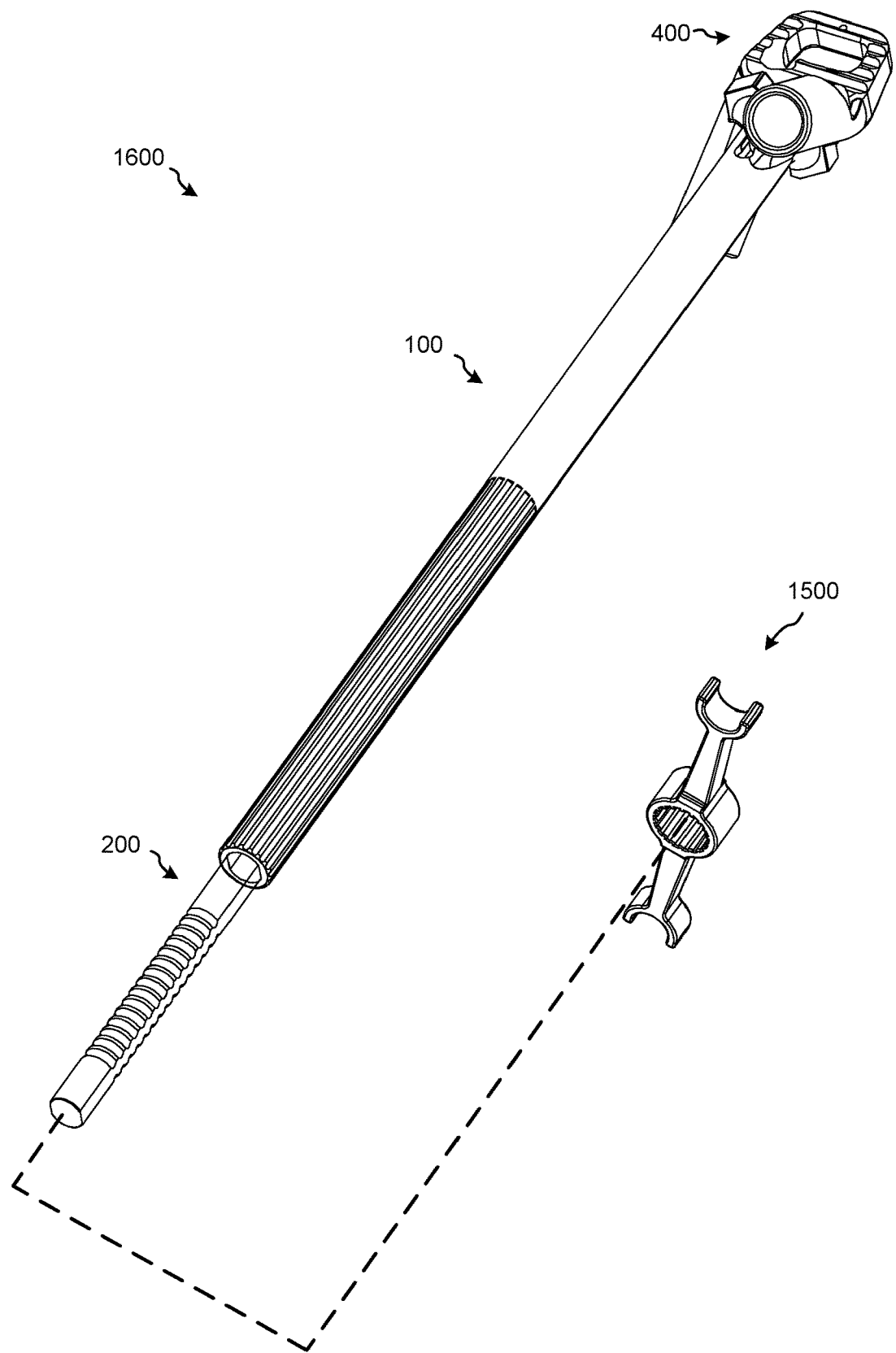
FIG. 16A is an exploded view of an insertion assembly including the inserter tool, the intervertebral spacer, the DTS guide, and the U-support tool, prior to assembly.
Figure 16B:
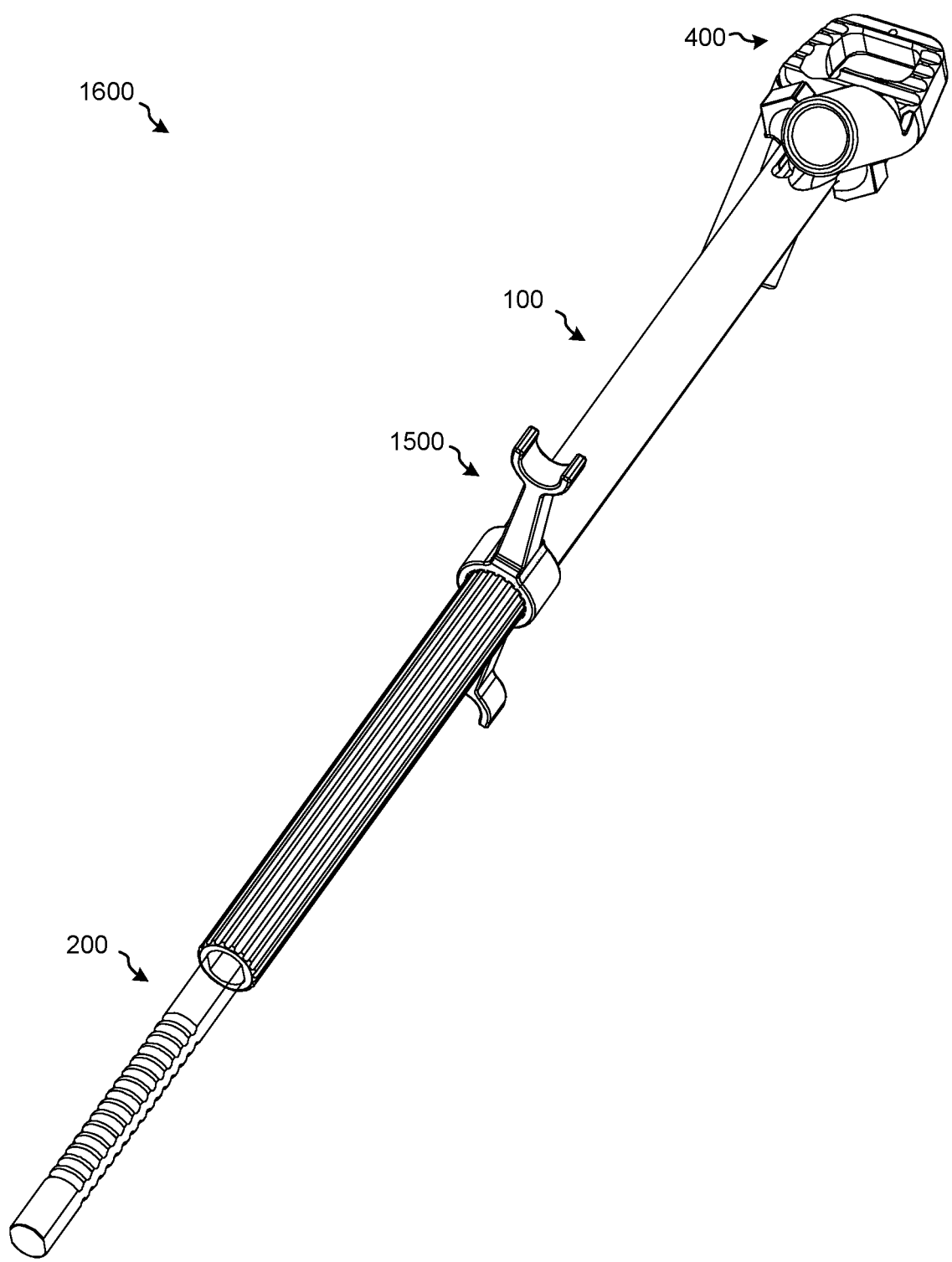
FIG. 16B is a perspective view of the insertion assembly of FIG. 16A after assembly.

FIGS. 16A and 16B illustrate how the U-support tool 1500 may be coupled to the DTS guide 100 (which itself may be coupled to the inserter tool 200 and the intervertebral spacer 400) in order to form an insertion assembly 1600. The one or more ring splines 1570 may be configured to engage the one or more shaft splines 115 formed on the DTS guide 100 in order to couple the U-support tool 1500 to the DTS guide 100 at a selected orientation. Thus, the U-support tool 1500 may be coupled to the DTS guide 100 at one or more discrete orientations or angles by rotating the one or more ring splines 1570 relative to the one or more shaft splines 115 before sliding the U-support tool 1500 onto the DTS guide 100. The one or more ring splines 1570 and the one or more shaft splines 115 may be shaped and spaced apart from each other according to any desired distance in order to achieve a desired set of discrete angles between the U-support tool 1500 and the DTS guide 100. As one non-limiting example, the shape and spacing of the one or more ring splines 1570 and the one or more shaft splines 115 may be chosen to achieve a set of different orientations that are about 15 degrees apart from each other.

Figure 17A:
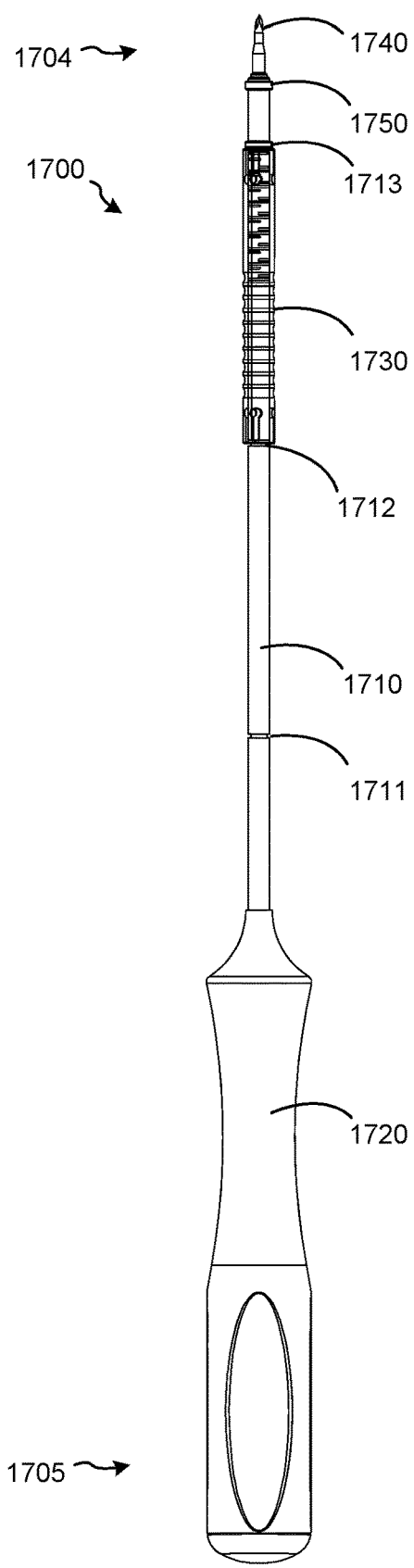
FIG. 17A is a side view of a flexible awl tool, according to an embodiment of the present disclosure.
Figure 17B:
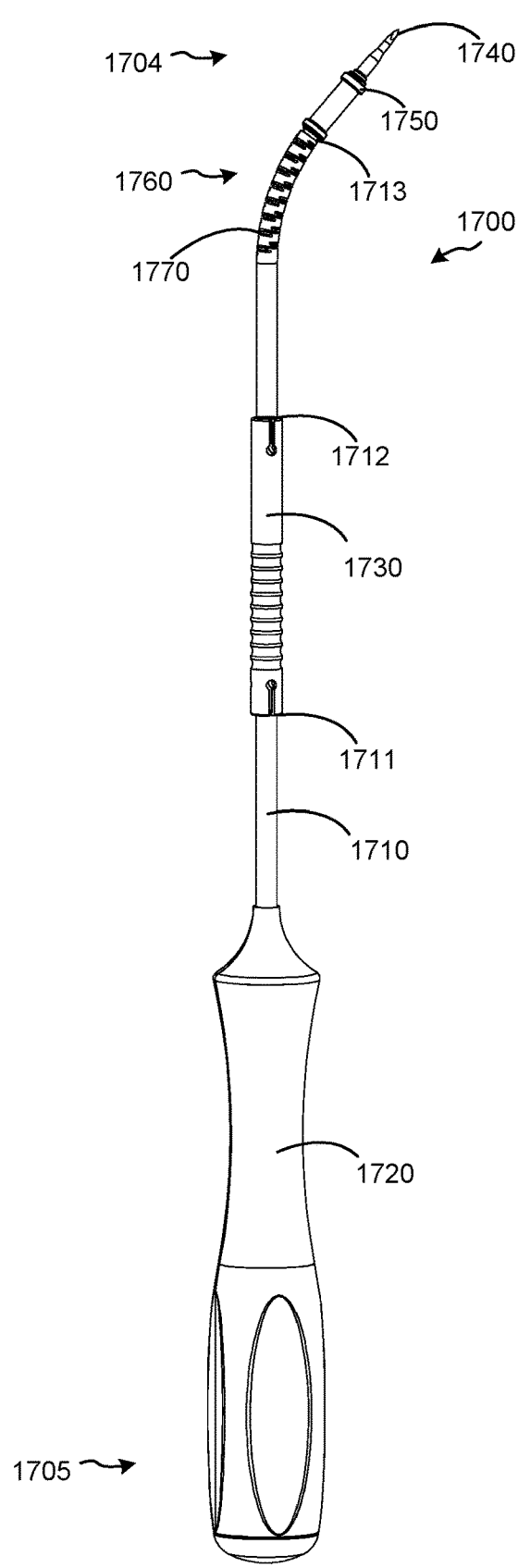
FIG. 17B is a side view of the flexible awl tool of FIG. 17A, with the shaft in flexion.

FIGS. 17A and 17B illustrate two side views of a flexible awl tool 1700, according to an embodiment of the present disclosure. In general, the flexible awl tool 1700 may include a proximal end 1705, a distal end 1704, a shaft 1710, a handle 1720, an awl sleeve 1730, an awl depth stop ring 1750, and a drill tip 1740. The awl sleeve 1730 may translate in the proximal to distal direction along the shaft 1710 in order to selectively prevent or allow the shaft 1710 from bending at the flexible portion 1760 of the shaft 1710. For example, FIG. 17A shows the awl sleeve 1730 translated distally in order to provide rigid support to the shaft 1710 over the flexible portion 1760 of the shaft, and FIG. 17B shows the awl sleeve 1730 translated proximally in order to allow the flexible portion 1760 of the shaft 1710 the freedom to bend and flex. The shaft 1710 may also include a first notch 1711, a second notch 1712, and a third notch 1713 which may interact with corresponding protrusions formed on the proximal and distal ends of the awl sleeve 1730 in order to selectively retain the awl sleeve 1730 in a locked position (e.g., the awl sleeve 1730 is translated to the proximal position) and an unlocked position (e.g., the awl sleeve 1730 is translated to the distal position). A tactile and/or audible "click" may be felt and/or heard by the surgeon when the awl sleeve 1730 reaches the unlocked and/or locked positions. The flexible portion 1760 of the shaft 1710 may include a plurality of slots 1770 that are configured to allow the flexible portion 1760 of the shaft 1710 to bend and flex. However, it will be understood that any suitable structure or arrangement may also be utilized to achieve a flexible shaft.

Figure 18:
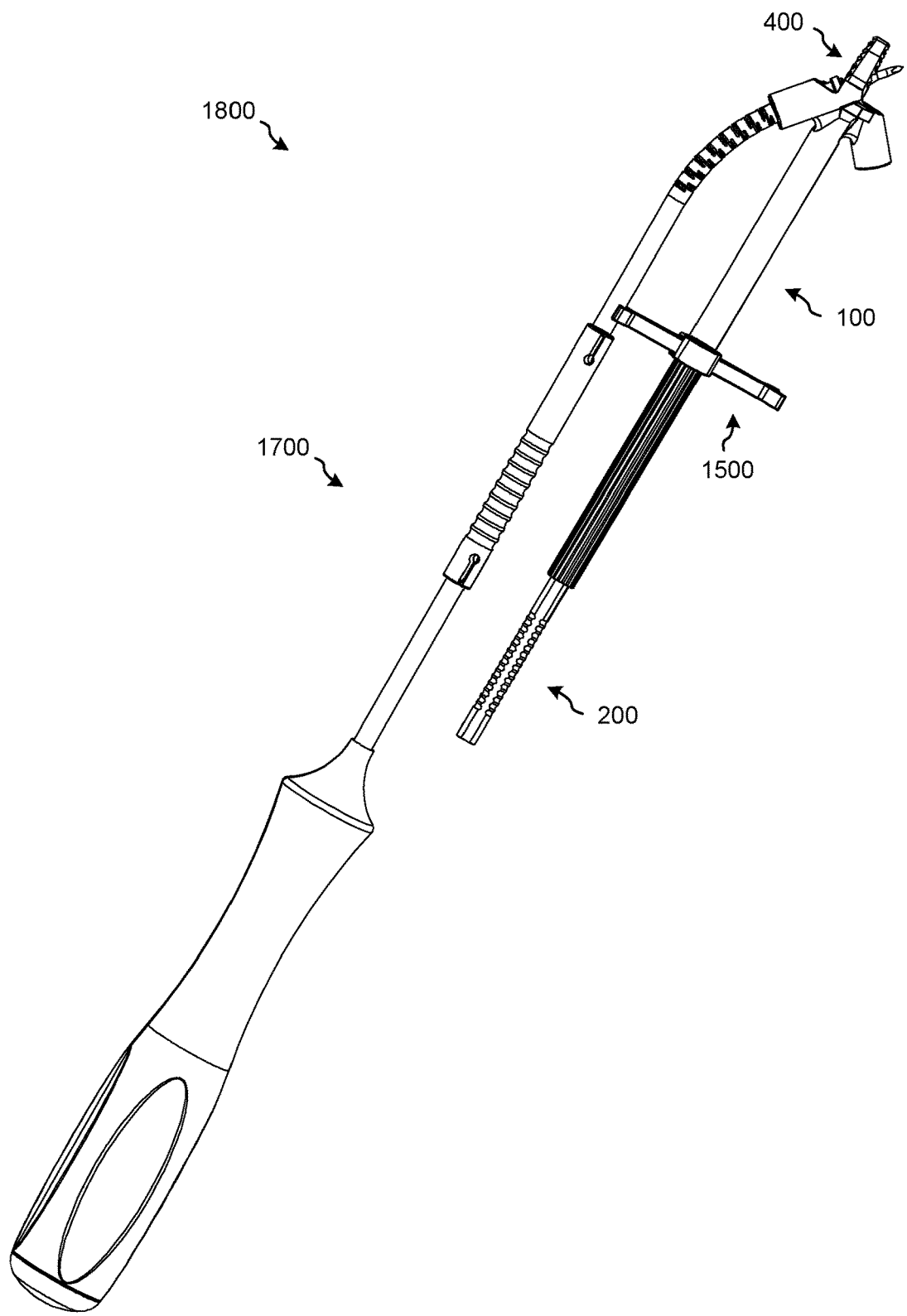
FIG. 18 illustrates an insertion assembly including the inserter tool, the intervertebral spacer, the DTS guide, the U-support tool, and the flexible awl tool assembled together.

FIG. 18 illustrates an insertion assembly 1800 including the inserter tool 200, the intervertebral spacer 400, the DTS guide 100, the U-support tool 1500, and the flexible awl tool 1700 assembled together in order to form bone tunnels within vertebral bodies (not shown) adjacent the intervertebral spacer 400. The drill tip 1740 of the flexible awl tool 1700 can be guided by the DTS guide 100 through the first and second DTS guide channels 121, 122. The awl depth stop ring 1750 may abut the first and second depth stops 433, 434 formed in the intervertebral spacer 400 to control the depth of the drill tip 1740 that may protrude into the vertebral bodies adjacent the intervertebral spacer 400. The surgeon may also utilize the U-support tool 1500 to help guide the shaft 1710 of the flexible awl tool 1700. For example, the surgeon may press the shaft 1710 of the flexible awl tool 1700 against the U-support tool 1500 while he/she rotates the flexible awl tool 1700 to drill bone tunnels into the vertebral bodies adjacent the intervertebral spacer 400. In this manner, a proximal portion the shaft 1710 may remain closer to the shaft 210 of the inserter tool 200 and/or the shaft 110 of the DTS guide 100 and a smaller incision may be utilized during the procedure. In one embodiment, a proximal portion the shaft 1710 may be substantially parallel to the shaft 210 of the inserter tool 200 and/or substantially parallel to the shaft 110 of the DTS guide 100. Once the bone tunnels are formed in the vertebral bodies adjacent the intervertebral spacer 400, the flexible awl tool 1700 may be removed from the patient in preparation for the next step in the procedure.

However, it will also be understood that in an alternative surgical procedure, the U-support tool 1500 and DTS guide 100 may be decoupled and removed from the patient, the awl sleeve 1730 may be moved to the locked position in order to prevent the flexible awl tool 1700 from bending, and a second and third incision may be made in the patient in order to approach the first and second fastener channels 431, 432 of the intervertebral spacer 400 via the second and third incisions with the flexible awl tool 1700 in its straight configuration in order to drill the bone tunnels.

Figure 19A:
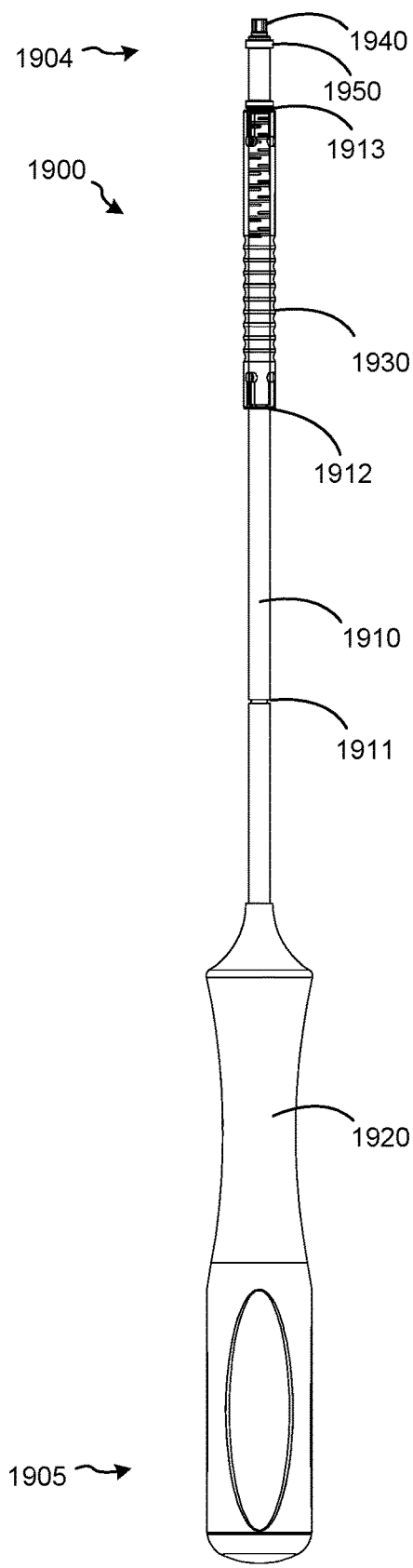
FIG. 19A is a side view of a flexible driver tool, according to an embodiment of the present disclosure.
Figure 19B:
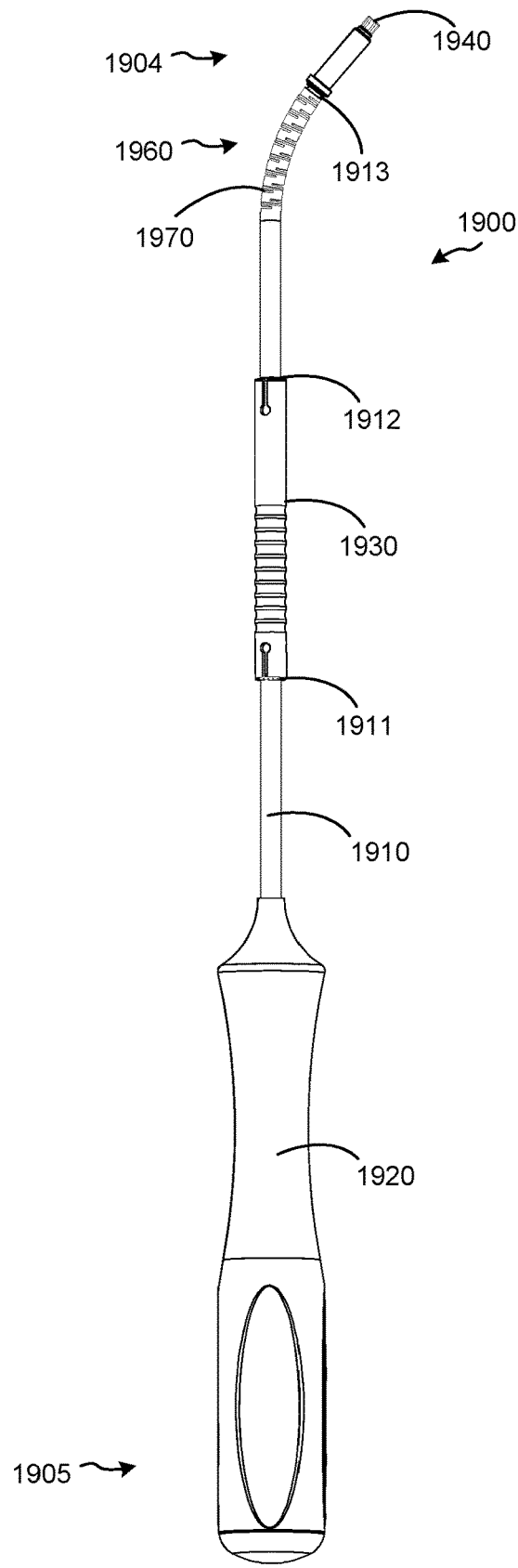
FIG. 19B is a side view of the flexible driver tool of FIG. 19A, with the shaft in flexion.

FIGS. 19A and 19B illustrate two side views of a flexible driver tool 1900, according to an embodiment of the present disclosure. In general, the flexible driver tool 1900 may include a proximal end 1905, a distal end 1904, a shaft 1910, a handle 1920, a driver sleeve 1930, a driver depth stop ring 1950, and a driver engagement feature 1940. The driver sleeve 1930 likewise may translate in the proximal to distal direction along the shaft 1910 in order to selectively prevent or allow the shaft 1910 from bending at the flexible portion 1960 of the shaft 1910. For example, FIG. 19A shows the driver sleeve 1930 translated distally in order to provide rigid support to the shaft 1910 over the flexible portion 1960 of the shaft 1910, and FIG. 19B shows the driver sleeve 1930 translated proximally in order to allow the flexible portion 1960 of the shaft 1910 the freedom to bend and flex. The shaft 1910 may also include a first notch 1911, a second notch 1912, and a third notch 1913 which may interact with corresponding protrusions formed on the proximal and distal ends of the driver sleeve 1930 in order to selectively retain the driver sleeve 1930 in a locked position (e.g., the driver sleeve 1930 is translated to the proximal position) and an unlocked position (e.g., the driver sleeve 1930 is translated to the distal position). The flexible portion 1960 of the shaft 1910 may include a plurality of slots 1970 configured to allow the flexible portion 1960 of the shaft 1910 to bend and flex. However, it will be understood that any suitable structure or arrangement may be utilized to achieve a flexible shaft.

Figure 20:
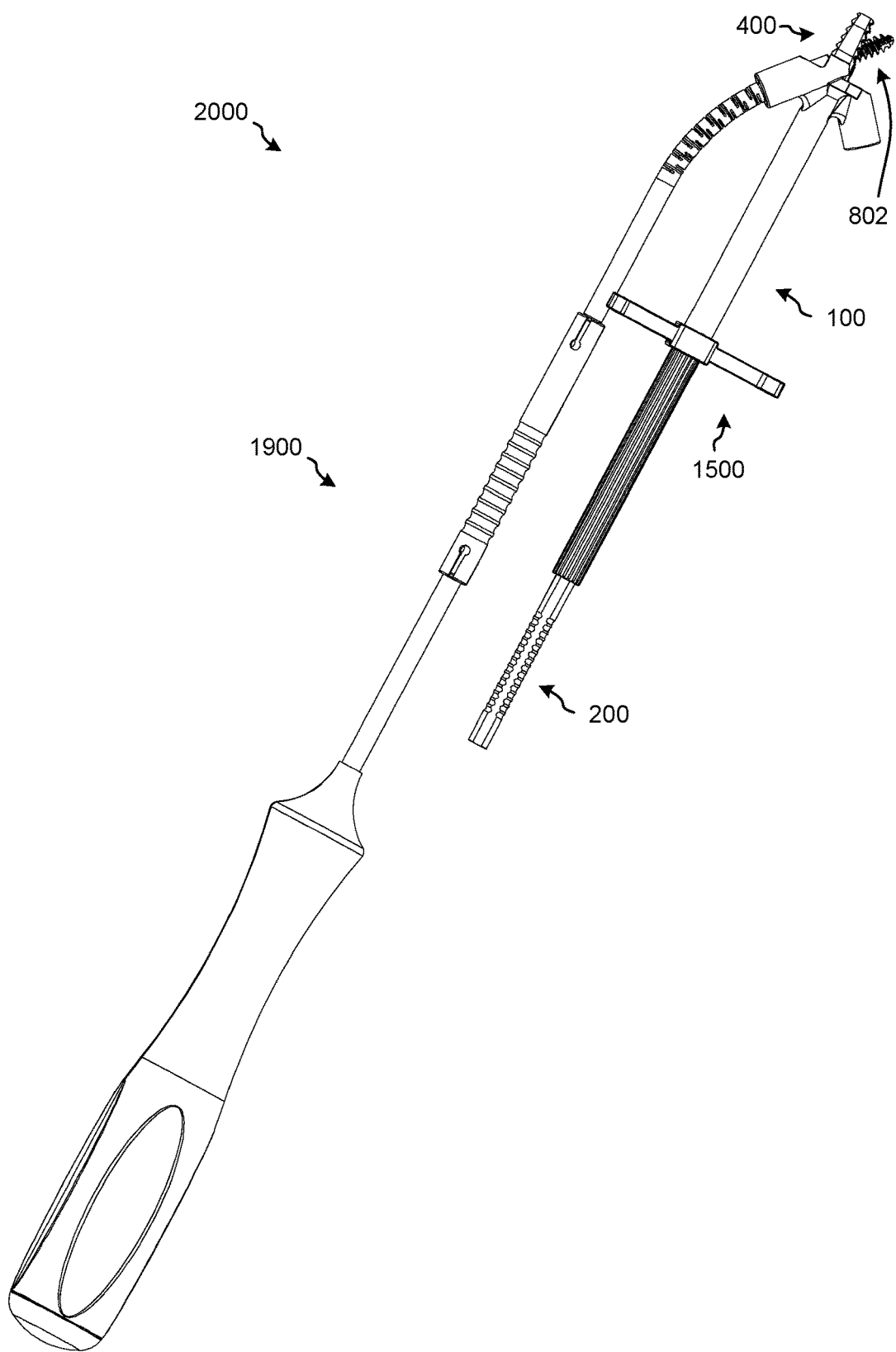
FIG. 20 illustrates an insertion assembly including the inserter tool, the intervertebral spacer, the bone screw, the DTS guide, the U-support tool, and the flexible driver tool assembled together.

FIG. 20 illustrates an insertion assembly 2000 including the inserter tool 200, the intervertebral spacer 400, the DTS guide 100, the U-support tool 1500, and the flexible driver tool 1900 assembled together in order to drive a bone screw 802 into a vertebral body (not shown). The driver engagement feature 1940 of the flexible driver tool 1900 can be any suitable style (e.g., Torx, hex, etc.) and can include the ability to retainably couple with the bone screw 802 (e.g., via a magnetic coupling, via a mechanical coupling such with tapered surfaces, etc.). The driver engagement feature 1940 of the flexible driver tool 1900 can be guided by the DTS guide 100 through the first and second DTS guide channels 121, 122. The driver depth stop ring 1950 may abut the first and second depth stops 433, 434 formed in the intervertebral spacer 400 to control the depth of the bone screw 802 into the vertebral body. The surgeon may also utilize the U-support tool 1500 to help guide the shaft 1910 of the flexible driver tool 1900. For example, the surgeon may press the shaft 1910 of the flexible driver tool 1900 against the U-support tool 1500 while he/she rotates the flexible driver tool 1900 to drive the bone screw 802 into the vertebral body. In this manner, a proximal portion the shaft 1910 may likewise remain closer to the shaft 210 of the inserter tool 200 and/or the shaft 110 of the DTS guide 100 and a smaller incision may be utilized during the procedure. In one embodiment, a proximal portion of the shaft 1910 may be substantially parallel to the shaft 210 of the inserter tool 200 and/or substantially parallel to the shaft 110 of the DTS guide 100. Once the bone screws are driven into the vertebral bodies adjacent the intervertebral spacer 400, the flexible driver tool 1900 may be removed from the patient in preparation for the next step in the procedure.

However, it will also be understood that in an alternative surgical procedure, the U-support tool 1500 and DTS guide 100 may be decoupled and removed from the patient, the driver sleeve 1930 may be moved to the locked position in order to prevent the flexible driver tool 1900 from bending, and a second and third incision may be made in the patient in order to approach the first and second fastener channels 431, 432 of the intervertebral spacer 400 via the second and third incisions with the flexible driver tool 1900 in its straight configuration in order to drive the bone screws into the vertebral bodies.

Once the bone screws have been properly placed into the vertebral bodies adjacent the intervertebral spacer 400, the surgeon may remove all of the tools from the patient in preparation for the next step of the procedure. In this step, the driver sleeve 1930 may be moved distally to prevent the flexible driver tool 1900 from bending.

Figure 21:
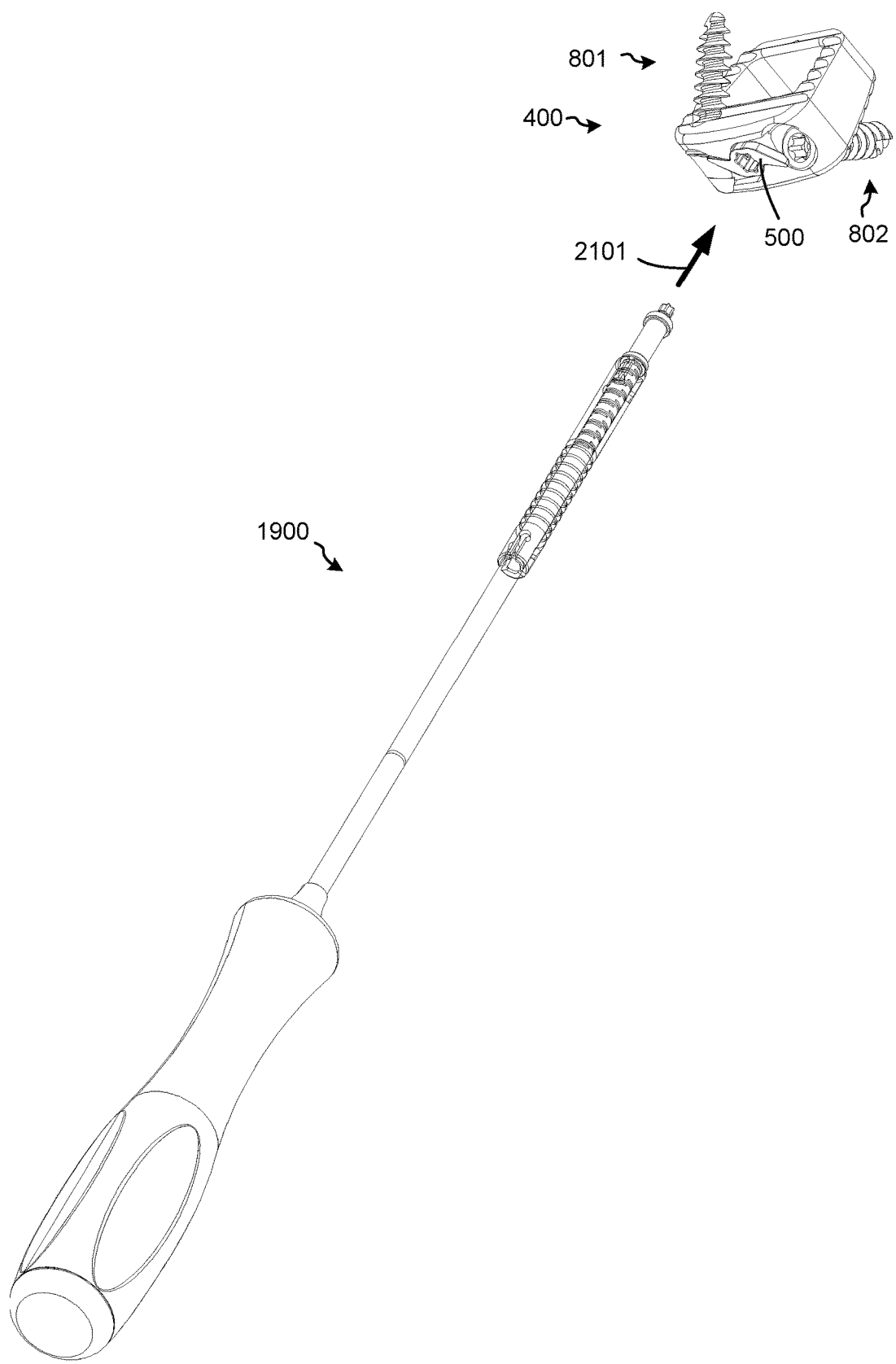
FIG. 21 illustrates the flexible driver tool of FIG. 19A coupling to the locking member in order to rotate the locking member to a locked position and prevent the bone screws from backing out of the intervertebral spacer.

FIG. 21 illustrates how the flexible driver tool 1900 of FIG. 19A may be moved in the direction of arrow 2101 to couple with the locking member 500 and to rotate the locking member 500 from an unlocked position and a locked position in order to prevent the bone screws 801, 802 from backing out of the intervertebral spacer 400. A tactile and/or audible "click" may be felt and/or heard by the surgeon when the locking member 500 reaches the unlocked and/or locked positions.

Figure 22:
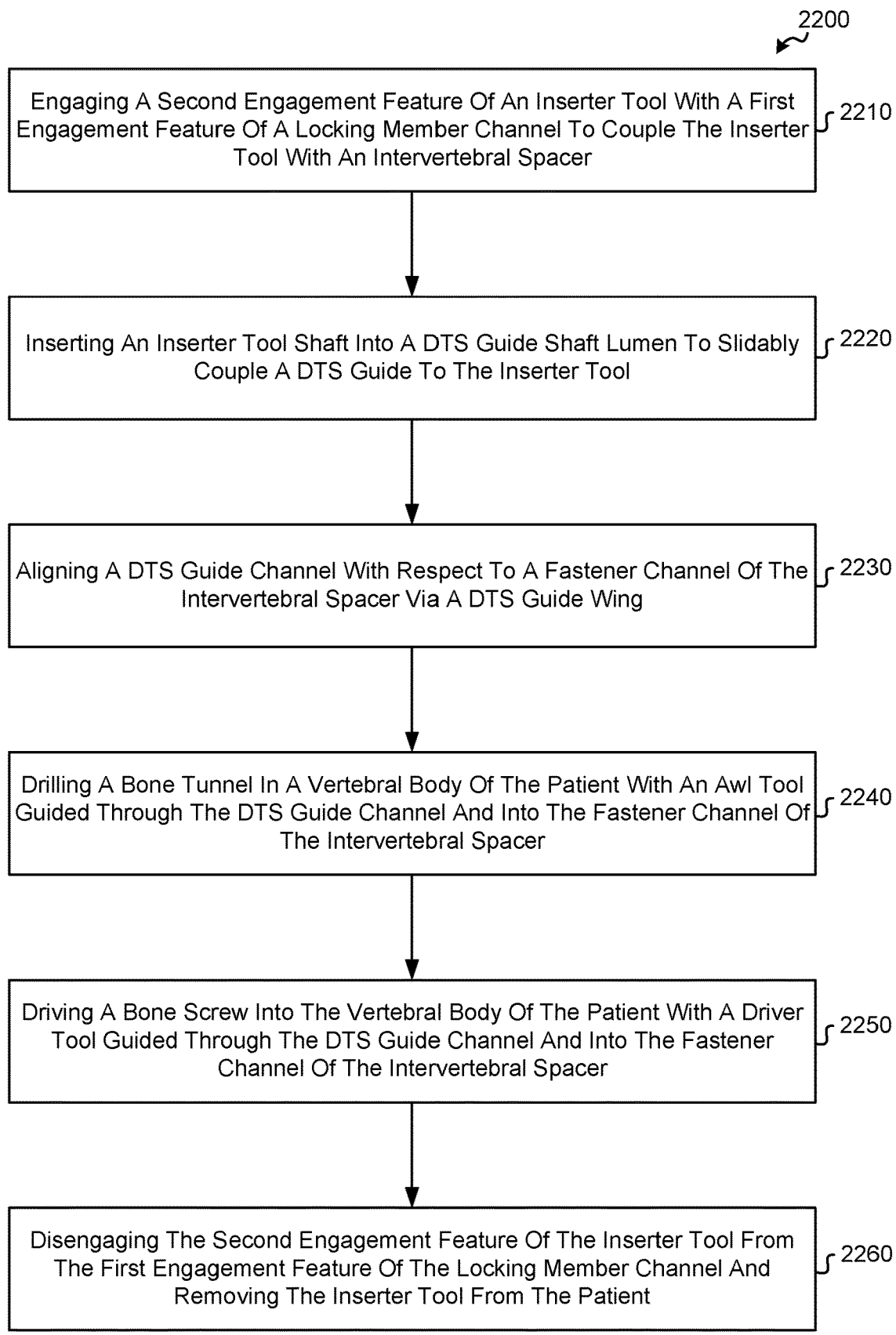
FIG. 22 illustrates a flowchart of a method for assembling an intervertebral spacer and insertion assembly, according to an embodiment of the present disclosure.

FIG. 22 illustrates a flowchart of a method 2200 for assembling an intervertebral spacer and insertion assembly, according to an embodiment of the present disclosure. In general, the method 2200 may include the use of an intervertebral spacer comprising a superior surface configured to engage a superior vertebral body, an inferior surface configured to engage an inferior vertebral body, and a peripheral wall extending from the superior surface to the inferior surface. The peripheral wall may comprise a fastener channel configured to receive a fastener and a locking member channel adjacent the fastener channel comprising a first engagement feature formed therein. The fastener channel may be oriented to pass through the peripheral wall and the superior or inferior surface of the intervertebral spacer.

The method 2200 may begin with a step 2210 in which a second engagement feature of an inserter tool may be engaged with the first engagement feature of the locking member channel in order to couple the inserter tool to the intervertebral spacer. In at least one embodiment, the first and second engagement features may comprise threading.

Once the second engagement feature has been engaged with the first engagement feature and the inserter tool has been coupled to the intervertebral spacer, the method 2200 may proceed to a step 2220 in which a proximal end of an inserter tool shaft may be inserted into a distal opening of a DTS guide shaft lumen of a DTS guide in order to slidably couple the DTS guide to the inserter tool. In at least one embodiment, the inserter tool shaft and the DTS guide shaft lumen may each have complementary "double D" shapes.

Once the DTS guide has been slidably coupled to the inserter tool, the method 2200 may proceed to a step 2230 in which a DTS guide channel of the DTS guide may be aligned with respect to the fastener channel of the intervertebral spacer via a DTS guide wing coupled to the DTS guide. In at least one embodiment, the DTS guide wing may be configured to abut against a surface of the peripheral wall in order to align the DTS guide channel with respect to the fastener channel. In this manner, the aligned DTS guide channel can guide the fastener through the DTS guide channel and into the fastener channel of the intervertebral spacer.

Alternatively, or in addition thereto, the method 2200 may also include any one or more of the following steps, which may be performed in any order: (1) a step 2240 in which an awl tool may be guided through the DTS guide channel and into the fastener channel of the intervertebral spacer, such that a bone tunnel may be drilled into a vertebral body of the patient with the awl tool; (2) a step 2250 in which a fastener may be guided through the DTS guide channel and into the fastener channel of the intervertebral spacer, such that the fastener may be driven into the bone tunnel with the driver tool; and (3) a step 2260 in which the second engagement feature of the inserter tool may be disengaged with the first engagement feature of the locking member channel in order to uncouple the inserter tool from the intervertebral spacer, such that inserter tool may be removed from the patient.

Any methods disclosed herein comprise one or more steps or actions for performing the described method. One or more of the method steps and/or actions may be omitted from and of the methods disclosed herein. Moreover, any of the method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

As defined herein, "substantially equal to" means "equal to," or within about a + or −10% relative variance from one another.

While specific embodiments and applications of the present disclosure have been illustrated and described, it is to be understood that the scope of the appended claims is not limited to the precise configuration and components disclosed herein. Various modifications, changes, and variations which will be apparent to those skilled in the art may be made in the arrangement, operation, and details of the systems, methods, and devices disclosed herein.

What is claimed is:

1. An intervertebral spacer insertion system comprising:
an intervertebral spacer comprising:
a superior surface configured to engage a superior vertebral body;
an inferior surface configured to engage an inferior vertebral body; and
a proximal surface comprising:
a first fastener channel configured to receive a first fastener, the first fastener channel oriented to pass through the proximal and superior surfaces of the intervertebral spacer at a first angle;
a second fastener channel configured to receive a second fastener, the second fastener channel oriented to pass through the proximal and inferior surfaces of the intervertebral spacer at a second angle; and
a locking member channel intermediate the first and second fastener channels, the locking member channel comprising a first engagement feature formed therein; and
an insertion assembly comprising:
an inserter tool comprising:
an inserter tool shaft; and
a second engagement feature formed on a distal end of the inserter tool shaft,
wherein the second engagement feature is configured to engage the first engagement feature in order to removably couple the intervertebral spacer with the inserter tool; and
a DTS guide comprising:
a DTS guide shaft;
a DTS guide shaft lumen passing through the DTS guide shaft, the DTS guide shaft lumen configured to receive the inserter tool shaft therein and slidably couple the DTS guide with the inserter tool;
a first DTS guide member having a first DTS guide channel configured to receive the first fastener at the first angle and guide the first fastener into the first fastener channel of the intervertebral spacer;
a second DTS guide member having a second DTS guide channel configured to receive the second fastener at the second angle and guide the second fastener into the second fastener channel of the intervertebral spacer;
a first DTS guide wing proximate the first DTS guide member, the first DTS guide wing configured to abut against a first surface of the intervertebral spacer; and
a second DTS guide wing proximate the second DTS guide member, the second DTS guide wing configured to abut against a second surface of the intervertebral spacer,
wherein, the first and second DTS guide wings are configured to align the first and second DTS guide channels with respect to the first and second fastener channels, independently of any additional apertures or recesses formed in the intervertebral spacer, in order to respectively guide the first and second fasteners through the first and second DTS guide channels and into the first and second fastener channels of the intervertebral spacer.

2. The intervertebral spacer insertion system of claim 1, wherein the first engagement feature comprises first threading and the second engagement feature comprises second threading.

3. The intervertebral spacer insertion system of claim 1, wherein the inserter tool shaft comprises at least one engagement surface configured to engage at least one complementarily shaped lumen engagement surface formed in the DTS guide shaft lumen in order to orient the DTS guide relative to the inserter tool.

4. The intervertebral spacer insertion system of claim 3, wherein the insertion assembly further comprises a handle that is removably couplable with the inserter tool, the handle comprising at least one handle engagement surface configured to engage the at least one engagement surface of the inserter tool shaft to stabilize the handle relative to the inserter tool.

5. The intervertebral spacer insertion system of claim 1, wherein the inserter tool shaft comprises a ridge configured to couple with a recess formed within the DTS guide shaft lumen to prevent the DTS guide from slidably translating relative to the inserter tool.

6. The intervertebral spacer insertion system of claim 1, wherein:
the inserter tool comprises at least one guide fin; and
the DTS guide shaft comprises a DTS guide fin slot configured to receive the at least one guide fin to orient the DTS guide relative to the inserter tool.

7. The intervertebral spacer insertion system of claim 1, wherein the DTS guide comprises at least one depth stop surface configured to prevent over-insertion of the intervertebral spacer between two vertebral bodies of a patient.

8. An insertion assembly configured to couple an intervertebral spacer comprising a superior surface configured to engage a superior vertebral body, an inferior surface configured to engage an inferior vertebral body, and a peripheral wall extending from the superior surface to the inferior surface, the peripheral wall comprising a fastener channel configured to receive a fastener, the fastener channel oriented to pass through the peripheral wall and the superior or inferior surface of the intervertebral spacer, and a locking member channel adjacent the fastener channel comprising a first engagement feature, the insertion assembly comprising:
an inserter tool comprising:
an inserter tool shaft; and
a second engagement feature formed on a distal end of the inserter tool shaft,
wherein the second engagement feature is configured to engage the first engagement feature of the locking member channel and removably couple the inserter tool to the intervertebral spacer; and
a DTS guide comprising:
a DTS guide shaft;
a DTS guide shaft lumen passing through the DTS guide shaft and configured to receive the inserter tool shaft therein to slidably couple the DTS guide to the inserter tool;
a DTS guide member coupled to a distal end of the DTS guide shaft, the DTS guide member comprising a DTS guide channel formed through the DTS guide member and configured to receive the fastener; and
a DTS guide wing proximate the DTS guide member, the DTS guide wing configured to abut against a surface of the peripheral wall and align the DTS guide channel with respect to the fastener channel in order to guide the fastener through the DTS guide channel and into the fastener channel of the intervertebral spacer.

9. The insertion assembly of claim 8, wherein the first engagement feature comprises first threading and the second engagement feature comprises second threading.

10. The insertion assembly of claim 8, wherein the inserter tool shaft comprises at least one engagement surface configured to engage at least one complementarily shaped lumen engagement surface formed in the DTS guide shaft lumen in order to orient the DTS guide relative to the inserter tool.

11. The insertion assembly of claim 10, wherein the insertion assembly further comprises a handle that is removably couplable with the inserter tool, the handle comprising at least one handle engagement surface configured to engage the at least one engagement surface of the inserter tool shaft to stabilize the handle relative to the inserter tool.

12. The insertion assembly of claim 8, wherein the inserter tool shaft comprises a ridge configured to couple with a recess formed within the DTS guide shaft lumen to prevent the DTS guide from slidably translating relative to the inserter tool.

13. The insertion assembly of claim 8, wherein:
the inserter tool comprises at least one guide fin; and
the DTS guide shaft comprises a DTS guide fin slot configured to receive the at least one guide fin to orient the DTS guide relative to the inserter tool.

14. The insertion assembly of claim 8, wherein the DTS guide wing aligns the DTS guide channel with respect to the fastener channel, independently of any additional apertures or recesses formed in the intervertebral spacer.

15. A method of assembling an insertion assembly and an intervertebral spacer comprising a superior surface configured to engage a superior vertebral body, an inferior surface configured to engage an inferior vertebral body, and a peripheral wall extending from the superior surface to the inferior surface, the peripheral wall comprising a fastener channel configured to receive a fastener, the fastener channel oriented to pass through the peripheral wall and the superior or inferior surface of the intervertebral spacer, and a locking member channel adjacent the fastener channel and comprising a first engagement feature formed therein, the method comprising:

engaging a second engagement feature of an inserter tool with the first engagement feature of the locking member channel to couple the inserter tool to the intervertebral spacer;

inserting a proximal end of an inserter tool shaft into a distal opening of a DTS guide shaft lumen of a DTS guide to slidably couple the DTS guide to the inserter tool; and aligning a DTS guide channel of the DTS guide with respect to the fastener channel of the intervertebral spacer via a DTS guide wing coupled to the DTS guide, the DTS guide wing configured to abut against a surface of the peripheral wall to align the DTS guide channel with respect to the fastener channel in order to guide the fastener through the DTS guide channel and into the fastener channel of the intervertebral spacer.

16. The method of claim 15, further comprising:
inserting a proximal end of the inserter tool shaft into a distal opening of a handle to couple the handle to the inserter tool.

17. The method of claim 16, further comprising:
manipulating the handle coupled to the inserter tool to insert the intervertebral spacer between two vertebral bodies of a patient.

18. The method of claim 17, further comprising:
drilling a bone tunnel in a vertebral body of the patient with an awl tool guided through the DTS guide channel and into the fastener channel of the intervertebral spacer.

19. The method of claim 18, further comprising:
driving a bone screw into the vertebral body of the patient with a driver tool guided through the DTS guide channel and into the fastener channel of the intervertebral spacer.

20. The method of claim 19, further comprising:
disengaging the second engagement feature of the inserter tool from the first engagement feature of the locking member channel to uncouple the inserter tool from the intervertebral spacer; and removing the inserter tool from the patient.

* * * * *